US011371045B2

(12) United States Patent
Vater et al.

(10) Patent No.: US 11,371,045 B2
(45) Date of Patent: Jun. 28, 2022

(54) METHOD OF MODULATING THE NUMBER AND THE DISTRIBUTION OF TUMOR-INFILTRATING LEUKOCYTES IN TUMORS

(71) Applicant: NOXXON PHARMA AG, Berlin (DE)

(72) Inventors: Axel Vater, Berlin (DE); Dirk Zboralski, Berlin (DE)

(73) Assignee: NOXXON Pharma AG, Berlin (DE)

( * ) Notice: Subject to any disclaimer, the term of this patent is extended or adjusted under 35 U.S.C. 154(b) by 0 days.

(21) Appl. No.: 16/093,645

(22) PCT Filed: Apr. 18, 2017

(86) PCT No.: PCT/EP2017/000495
§ 371 (c)(1),
(2) Date: Oct. 14, 2018

(87) PCT Pub. No.: WO2017/178119
PCT Pub. Date: Oct. 19, 2017

(65) Prior Publication Data
US 2020/0071701 A1 Mar. 5, 2020

(30) Foreign Application Priority Data
Apr. 15, 2016 (EP) .................................... 16000861
Oct. 7, 2016 (EP) .................................... 16002168

(51) Int. Cl.
*C12N 15/115* (2010.01)
*A61P 35/00* (2006.01)
*C07K 16/28* (2006.01)
*A61K 45/06* (2006.01)

(52) U.S. Cl.
CPC ............ *C12N 15/115* (2013.01); *A61P 35/00* (2018.01); *C07K 16/2818* (2013.01); *A61K 45/06* (2013.01); *C07K 2317/732* (2013.01); *C12N 2310/16* (2013.01); *C12N 2310/351* (2013.01); *C12N 2320/30* (2013.01)

(58) Field of Classification Search
CPC ... C12N 15/115; C12N 2310/16; A61P 35/00; C07K 2317/732
See application file for complete search history.

(56) References Cited

U.S. PATENT DOCUMENTS

| | | | | |
|---|---|---|---|---|
| 9,387,221 B2 * | 7/2016 | Purschke | ........... | A61K 31/7088 |
| 10,093,934 B2 * | 10/2018 | Purschke | ........... | A61K 31/7088 |
| 2013/0310422 A1 * | 11/2013 | Brown | .............. | A61B 5/04012 514/317 |

OTHER PUBLICATIONS

Hsu et al (Blood 117(5):1605-1613, 2011) (Year: 2011).*
Ferrajoli et al (Blood 114(22): 206, 2009) (Year: 2009).*
Vater et al., "Hematopoietic . . . CXCL12," Nature 94(1)150-157, 2013.
Roccaro et al., "SDF-1 . . . Therapy," Cell Reports 9, 118-128, 2014.
Vater & Klussmann, "Turning . . . Therapeutics," Drug Disc Today 20(1)147-155, 2015.
Feig et al., "Targeting . . . Cancer," PNAS 110(50)20212-20217, 2013.
Zboralski et al., "CXCL12 . . . Spheroids," ESMO Cong, Copenhagen, DK, Abst. 1083P, 2016.
Zboralski et al., "CXCL12 . . . Model," 58th ASH Ann Meeting, San Diego, CA, Abst. 3021, 2016.
Burger et al., "CXCR4 . . . Cancers," Leuk 23, 43-52, 2009.
Hoellenriegel et al., "The Spiegelmer . . . Chemosensitization," Blood, 123(7)1032-1039, 2014.
Hattermann & Mentlein, "An Infernal . . . Biology," Ann Anat 195:103-110, 2013.
Weitzenfedl & Ben-Baruch, "The Chemokine . . . Cancer," Canc Lett 352:36-53, 2014.
Chang et al., "Cell . . . Chemotaxis," PLOS One 10(4)1-24, 2015.

* cited by examiner

*Primary Examiner* — Richard A Schnizer
(74) *Attorney, Agent, or Firm* — MDIP LLC

(57) ABSTRACT

The present invention is related to a molecule capable of inhibiting signaling between SDF-1 and CXCR4 and/or CXCR7, wherein the molecule is for use in a method of modulating the number and/or the spatial distribution of tumor-infiltrating leukocytes in a tumor and/or metastases.

17 Claims, 25 Drawing Sheets

Specification includes a Sequence Listing.

Type A SDF-1 binding nucleic acids

| Name | nt. | Sequence: 5′-3′ | Comp. | SEQ ID NO |
|---|---|---|---|---|
| 192-A10-001 | 38 | GCUGUGAAAGCAACAUGUCAA-UGAAAGGUAGCCGCAGC | | 60 |
| 192-G10 | 38 | GCUGUGAAAGUAACAUGUCAA-UGAAAGGUAACCACAGC | < | 61 |
| 192-F10 | 38 | GCUGUGAAAGUAACACGUCAA-UGAAAGGUAACCGCAGC | < | 62 |
| 192-B11 | 38 | GCUGUGAAAGUAACACGUCAA-UGAAAGGUAACCACAGC | = | 63 |
| 192-C9 | 38 | GCUGUAAAAGUAACAUGUCAA-UGAAAGGUAACUACAGC | < | 64 |
| 192-E10 | 38 | GCUGUAAAAGUAACAAGUCAA-UGAAAGGUAACUACAGC | < | 65 |
| 192-C10 | 38 | GCUGUGAAAGUAACAAGUCAA-UGAAAGGUAACCACAGC | = | 66 |
| 192-D11 | 38 | GCAGUGAAAGUAACAUGUCAA-UGAAAGGUAACCACAGC | < | 67 |
| 192-G11 | 38 | GCUGUGAAAGUAACAUGUCAA-UGAAAGGUAACCACUGC | < | 68 |
| 192-H11 | 38 | GCUAUGAAAGUAACAUGUCAA-UGAAAGGUAACCAUAGC | < | 69 |
| 192-D10 | 38 | GCUGCGAAAGCGACAUGUCAA-UGAAAGGUAGCCGCAGC | << | 70 |
| 192-E9 | 38 | GCUGUGAAAGCAACAUGUCAA-UGAAAGGUAGCCACAGC | << | 71 |
| 192-H9 | 38 | GCUGUGAAAGUAACAUGUCAA-UGAAAGGUAGCCGCAGC | << | 72 |
| 191-A6 | 39 | AGCGUGAAAGUAACACGUAAAAUGAAAGGUAACCACGCU | < | 73 |

terminal nucleotides that may hybridize to each other (bold)

nucleotides which may mainly comprise a SDF-binding motif nt.:= nucleotides [Geben Sie ein Zitat aus dem Dokument oder die Zusammenfassung eines interessanten Punkts ein. Sie können das Textfeld an einer beliebigen Stelle im Dokument positionieren. Verwenden Sie die Registerkarte 'Zeichentools', wenn Sie das Format des Textfelds 'Textzitat' ändern möchten.]

Comp.:= Clones were tested as aptamers in a competition binding assay vs. 192-A10-001

=:= equal binding affinity as 192-A10-001; <:= weaker binding affinity than 192-A1-001

<<:= much weaker binding affinity than 192-A10-001

Fig. 1

Derivatives of Type A SDF Binding Nucleic Acid 192-A10-001

| Name | nt. | Sequence: 5′-3′ | Comp. | PD: $K_D$ [nM] | TAX $IC_{50}$ [nM] | SEQ ID NO: |
|---|---|---|---|---|---|---|
| 192-A10-001 | 38 | **GCUGUG**AAAGCAACAUGUCAAUGAAAGGUAGC**CGCAGC** | | 1.5 | 0.1 - 0.2 | 60 |
| | | | | | | |
| 192-A10-002 | 36 | **CUGUG**AAAGCAACAUGUCAAUGAAAGGUAGC**CGCAG** | = | | = | 78 |
| 192-A10-003 | 34 | **UGUG**AAAGCAACAUGUCAAUGAAAGGUAGC**CGCA** | < | | < | 79 |
| 192-A10-004 | 32 | **GUG**AAAGCAACAUGUCAAUGAAAGGUAGC**CGC** | << | | << | 80 |
| 192-A10-005 | 30 | **UG**AAAGCAACAUGUCAAUGAAAGGUAGC**CG** | << | | << | 81 |
| 192-A10-006 | 28 | **G**AAAGCAACAUGUCAAUGAAAGGUAGC**C** | <<< | | | 82 |
| 192-A10-007 | 26 | AAAGCAACAUGUCAAUGAAAGGUAGC | i.a. | | | 83 |

terminal nucleotides at the 5′- and the 3′-end that may hybridize to each other (bold) nt.:= nucleotides nucleotides which may mainly comprise a SDF-binding motif i.a.:= inactive =:= equal binding affinity as 192-A10-001

</<</<<<:= weaker (<), much weaker (<<) or very much weaker (<<<) binding affinity than 192-A1-001

Comp.:= Clones were tested as aptamers in a competition binding assay vs. 193-A10-001

PD.:= Clones were tested as aptamers in a pull-down binding assay

TAX:= Clones were tested as Spiegelmers in a cell culture *in vitro* chemotaxis assay

Fig. 2A

Derivatives of Type A SDF Binding Nucleic Acid 192-A10-001

| Name | nt. | Sequence: 5′-3′ | Comp. | PD: $K_D$ [nM] | TAX $IC_{50}$ [nM] | SEQ ID NO: |
|---|---|---|---|---|---|---|
| 192-A10-001 | 38 | **GCUGUG**AAAGCAACAUGUCAAUGAAAGGUAGC**CGCAGC** | | 1.5 | 0.1 - 0.2 | 60 |
| 192-A10-002 | 36 | **CUGUG**AAAGCAACAUGUCAAUGAAAGGUAGC**CGCAG** | = | | = | 78 |
| 192-A10-008 | 36 | **GCGUG**AAAGCAACAUGUCAAUGAAAGGUAGC**CGCGC** | = | 1.5 | = | 84 |
| 192-A10-015 | 36 | **GCGCG**AAAGCAACAUGUCAAUGAAAGGUAGC**CGCGC** | < | 4.6 | | 85 |
| 192-A10-014 | 34 | **GCGG**AAAGCAACAUGUCAAUGAAAGGUAGC**CCGC** | < | 8.0 | = | 86 |
| 192-A10-016 | 34 | **CGUG**AAAGCAACAUGUCAAUGAAAGGUAGC**CGCG** | < | | | 87 |
| 192-A10-017 | 34 | **GCGC**AAAGCAACAUGUCAAUGAAAGGUAGC**GUGC** | i.a. | | | 88 |
| 192-A10-018 | 34 | **GUGC**AAAGCAACAUGUCAAUGAAAGGUAGC**GCGC** | <<< | | | 89 |
| 192-A10-019 | 34 | **CGCG**AAAGCAACAUGUCAAUGAAAGGUAGC**CGUG** | << | | | 90 |
| 192-A10-020 | 34 | **GGGC**AAAGCAACAUGUCAAUGAAAGGUAGC**GCCC** | <<* | | | 91 |
| 192-A10-021 | 34 | **GGCC**AAAGCAACAUGUCAAUGAAAGGUAGC**GGCC** | <<* | | | 92 |
| 192-A10-022 | 34 | **GCCC**AAAGCAACAUGUCAAUGAAAGGUAGC**GGGC** | <<* | | | 93 |
| 192-A10-023 | 34 | **CCCC**AAAGCAACAUGUCAAUGAAAGGUAGC**GGGG** | <<* | | | 94 |

terminal nucleotides at the 5′- and the 3′-end that may hybridize to each other (bold) nt.:= nucleotides nucleotides which may mainly comprise a SDF-binding motif (boxed) i.a.:= inactive =:= equal binding affinity as 192-A10-001/ -008

</<</<<<:= weaker (<), much weaker (<<) or very much weaker (<<<) binding affinity than 192-A1-001/ -008

Comp.:= Clones were tested as aptamers in a competition binding assay vs. 192-A10-001 (* = except from 192-A10-020, -021, -022, and –023 which were tested vs. 193-A10-008 that has the identical binding affinity to SDF-1 as 192-A10-001)

PD.:= Clones were tested as aptamers in a pull-down binding assay

TAX:= Clones were tested as Spiegelmers in a cell culture *in vitro* chemotaxis assay

Fig. 2B

Type B SDF-1 binding nucleic acids

| Name | nt. | Sequence: 5′-3′ | C. | SEQ ID NO: |
|---|---|---|---|---|
| 193-C2-001 | 47 | **AGCGUG**GUGUGAUCUAGAUGUAGUGGCUGAUCCUAGUCAGG**UACGCU** | + | 5 |
| 193-G2-001 | 47 | **AGCGUG**GUGUGAUCUAGAUGUAUUGGCUGAUCCUAGUCAGG**UACGCU** | + | 6 |
| 193-F2-001 | 47 | **AGCGUG**GUGUGAUCUAGAUGUAAUGGCUGAUCCUAGUCAGG**UGCGCU** | + | 7 |
| | | | | |
| 193-G1-002 | 45 | **GCGA**G GUGUGAUCUAGAUGUAGUGGCUGAUCCUAGUCAGG **U**G**CGC** | << | 8 |
| 193-D2-002 | 45 | **GCGUG**GUGUGAUCUAGAUGUAGUGGCUGAUCCUAGUCAGG**UGCGC** | < | 9 |
| 193-A1-002 | 45 | **GC**A**UG**GUGUGAUCUAGAUGUAGUGGCUGAUCCUAGUCAGG**UG**CC**C** | <<< | 10 |
| 193-D3-002 | 45 | **GCGUG**GUGUGAUCUAGAUGUAAUGGCUGAUCCUAGUCAGGG**ACGC** | < | 11 |
| 193-B3-002 | 45 | **GCGUG**GUGUGAUCUAGAUGUAGAGGCUGAUCCUAGUCAGG**UACGC** | << | 12 |
| 193-H3-002 | 45 | **GCGUG**GUGUGAUCUAGAUGUAAAGGCUGAUCCUAGUCAGG**UACGC** | < | 13 |
| 193-E3-002 | 45 | **GCGUG**GUGUGAUCUAGAUGUAGUGGCUGUUCCUAGUCAGG**UAUGC** | << | 14 |
| 193-D1-002 | 45 | **GCGUG**GUGUGAUCUAGAUGUAGUGGCUGAUCCUAGUUAGG**UACGC** | <<< | 15 |

terminal nucleotides that may hybridize to each other (bold)

nucleotides which may mainly comprise a SDF-binding motif (boxed) nt.:= nucleotides

C.:= Clones C2, G2, and F2 were tested as aptamers in a competition binding assay vs. 192-A10-001; all other clones were tested as aptamers in a competition binding assay vs. 193-G2-012 that has the identical binding affinity to SDF-1 as 193-G2-001 (see Fig. 4B)

+:= better binding affinity than 192-A10-001

</<</<<<:= weaker (<), much weaker (<<) or very much weaker (<<<) binding affinity than 193-G2-001/ -012

Fig. 3

Derivatives of Type B SDF Binding Nucleic Acids 193-C2/G2-001

| Name | nt. | Sequence: 5'-3' | Comp. | PD $K_D$ [nM] | Biacore $K_D$ [nM] | SEQ ID NO: |
|---|---|---|---|---|---|---|
| 193-G2-001 | 47 | **AGCGUG**GUGUGAUCUAGAUGUAUUGGCUGAUCCUAGUCAGG**UACGCU** | | 0.3 | 0.5 | 6 |
| 193-C2-001 | 47 | **AGCGUG**GUGUGAUCUAGAUGUAGUGGCUGAUCCUAGUCAGG**UACGCU** | = | | 0.6 | 5 |
| | | | | | | |
| 193-C2-002 | 45 | **GCGUG**GUGUGAUCUAGAUGUAGUGGCUGAUCCUAGUCAGG**UACGC** | = | | 0.8 | 16 |
| 193-C2-003 | 43 | **CGUG**GUGUGAUCUAGAUGUAGUGGCUGAUCCUAGUCAGG**UACG** | < | | | 17 |
| 193-C2-004 | 41 | **GUG**GUGUGAUCUAGAUGUAGUGGCUGAUCCUAGUCAGG**UAC** | << | | | 18 |
| 193-C2-005 | 39 | **UG**GUGUGAUCUAGAUGUAGUGGCUGAUCCUAGUCAGG**UA** | <<< | | | 19 |
| 193-C2-006 | 37 | **G**GUGUGAUCUAGAUGUAGUGGCUGAUCCUAGUCAGG**U** | <<< | | | 20 |
| 193-C2-007 | 35 | GUGUGAUCUAGAUGUAGUGGCUGAUCCUAGUCAGG | i.a. | | | 21 |

terminal nucleotides at the 5′- and the 3′-end that may hybridize to each other (bold) nt.:= nucleotides nucleotides which may mainly comprise a SDF-binding motif i.a.:= inactive =:= equal binding affinity as 193-G2-001

</<</<<<:= weaker (<), much weaker (<<) or very much weaker (<<<) binding affinity than 193-G2-001

Comp.:= Clones were tested as aptamers in a competition binding assay vs. 193-G2-001

PD.:= Clones were tested as aptamers in a pull-down binding assay

Fig. 4A

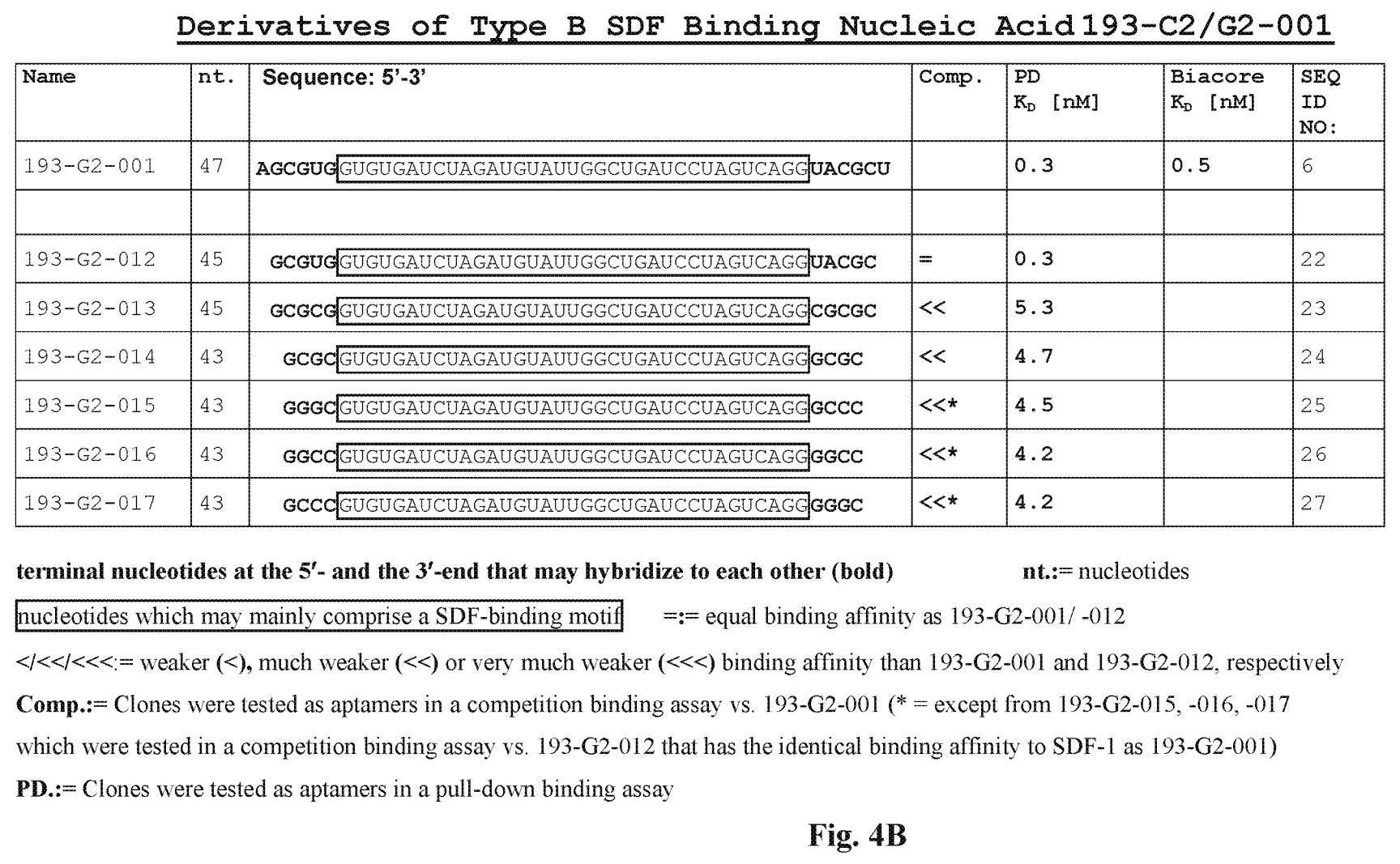

Derivatives of Type B SDF Binding Nucleic Acid 193-C2/G2-001

| Name | nt. | Sequence: 5'-3' | Comp. | PD $K_D$ [nM] | Biacore $K_D$ [nM] | SEQ ID NO: |
|---|---|---|---|---|---|---|
| 193-G2-001 | 47 | **AGCGUG**GUGUGAUCUAGAUGUAUUGGCUGAUCCUAGUCAGG**UACGCU** | | 0.3 | 0.5 | 6 |
| | | | | | | |
| 193-G2-012 | 45 | **GCGUG**GUGUGAUCUAGAUGUAUUGGCUGAUCCUAGUCAGG**UACGC** | = | 0.3 | | 22 |
| 193-G2-013 | 45 | **GCGCG**GUGUGAUCUAGAUGUAUUGGCUGAUCCUAGUCAGG**CGCGC** | << | 5.3 | | 23 |
| 193-G2-014 | 43 | **GCGC**GUGUGAUCUAGAUGUAUUGGCUGAUCCUAGUCAGG**GCGC** | << | 4.7 | | 24 |
| 193-G2-015 | 43 | **GGGC**GUGUGAUCUAGAUGUAUUGGCUGAUCCUAGUCAGG**GCCC** | <<* | 4.5 | | 25 |
| 193-G2-016 | 43 | **GGCC**GUGUGAUCUAGAUGUAUUGGCUGAUCCUAGUCAGG**GGCC** | <<* | 4.2 | | 26 |
| 193-G2-017 | 43 | **GCCC**GUGUGAUCUAGAUGUAUUGGCUGAUCCUAGUCAGG**GGGC** | <<* | 4.2 | | 27 |

terminal nucleotides at the 5'- and the 3'-end that may hybridize to each other (bold) nt.:= nucleotides nucleotides which may mainly comprise a SDF-binding motif (boxed) =:= equal binding affinity as 193-G2-001/ -012

</<</<<<:= weaker (<), much weaker (<<) or very much weaker (<<<) binding affinity than 193-G2-001 and 193-G2-012, respectively

Comp.:= Clones were tested as aptamers in a competition binding assay vs. 193-G2-001 (* = except from 193-G2-015, -016, -017 which were tested in a competition binding assay vs. 193-G2-012 that has the identical binding affinity to SDF-1 as 193-G2-001)

PD.:= Clones were tested as aptamers in a pull-down binding assay

Fig. 4B

Type C SDF-1 binding nucleic acids

| Name | nt. | Sequence: 5'-3' | Comp. | SEQ ID NO: |
|---|---|---|---|---|
| 197-B2 | 39 | GUGCUGCGGGGGUUAGGGCUAGAAGUCGGCCUGCAGCAC | < | 95 |
| 191-D5-001 | 39 | AGCGUGGCGAGGUUAGGGCUAGAAGUCGGUCGACACGCU | < | 96 |
| 197-H1 | 39 | GUGUUGCGGAGGUUAGGGCUAGAAGUCGGUCAGCAGCAC | < | 97 |
| 190-D3 | 48 | CGUGCGGCCUAAGAGGUUAGGGCUUAAAGUCGGUCUUUGGCCAACACG | << | 98 |
| 190-A3-001 | 48 | CGUGCGCUUGAGAUAGGGGUUAGGGCUUAAAGUCGGCUGAUUCUCACG | < | 99 |
| 190-A3-001* | 48 | CGUGCGCUUGAGAUAGGGGUUAGGGCUUAAAGUCGGCUGAUUCUCACG | < | 99 |
| 190-A2 | 48 | CGUGAUUGGUGAGGGGUUAGGGCUUGAAGUCGGCCUUGUCCAGUCACG | << | 100 |
| 191-A5 | 39 | AGCGUGAAGGGGUUAGGGCUCGAAGUCGGCUGACACGCU | << | 101 |
| 197-H3 | 39 | GUGCUGCGGGGGUUAGGGCUCGAAGUCGGCCCGCAGCAC | < | 102 |
| 197-B1 | 39 | GUGUUCCCGGGGUUAGGGCUUGAAGUCGGCCGGCAGCAC | << | 103 |
| 197-E3 | 39 | GUGUUGCAGGGGUUAGGGCUUGAAGUCGGCCUGCAGCAC | < | 104 |
| 197-H2 | 39 | GUGCUGCGGGGGUUAGGGCUCAAAGUCGGCCUGCAGCAC | << | 105 |
| 197-D1 | 38 | GUGCUGCCGGGGUUAGGGCUAA-AGUCGGCCGACAGCAC | << | 106 |
| 197-D2 | 39 | GUGCUGUGGGGGUCAGGGCUAGAAGUCGGCCUGCAGCAC | << | 107 |

terminal nucleotides that may hybridize to each other (bold)

nucleotides which may mainly comprise a SDF-binding motif nt.:= nucleotides Comp.:= Clones were tested as aptamers in a competition binding assay vs. 192-A10-001

=:= equal binding affinity as 192-A10; <:= weaker binding affinity than 192-A10 <<:= much weaker binding affinity than 192-A10

*:= alternative hybridization

Fig. 5

Derivatives of Type C SDF Binding Nucleic Acid 190-A3-001

| Name | nt. | Sequence: 5'-3' | Comp. | SEQ ID NO: |
|---|---|---|---|---|
| 190-A3-001 | 48 | **CGUG**CGCUUGAGAUAGG GGUUAGGGCUUAAAGUCGG CUGAUUCU**CACG** | | 99 |
| 190-A3-001* | 48 | CGUGCGCU**UGAGA**UA**GG** GGUUAGGGCUUAAAGUCGG **CU**GAU**UCUCA**CG | | 99 |
| | | | | |
| 190-A3-003 | 38 | **UGAGA**UA**GG** GGUUAGGGCUUAAAGUCGG CUGAU**UCUCA** | = | 112 |
| 190-A3-004 | 36 | **GAGA**UA**GG** GGUUAGGGCUUAAAGUCGG **CU**GAU**UCUC** | = | 113 |
| 190-A3-007 | 29 | **GG** GGUUAGGGCUUAAAGUCGG **CU**GAUUCU | <<< | 114 |

terminal nucleotides at the 5'- and the 3'-end that may hybridize to each other (bold) nt.:= nucleotides nucleotides which may mainly comprise a SDF-binding motif (boxed) =:= equal binding affinity as 190-A3-001

</<</<<<:= weaker (<), much weaker (<<) or very much weaker (<<<) binding affinity than 190-A3-001

Comp.:= Clones were tested as aptamers in a competition binding assay vs. 190-A3-001

*:= alternative hybridization of the terminal nucleotides

Fig. 6

Derivatives of Type C SDF Binding Nucleic Acid 191-D5-001

| Name | nt. | Sequence: 5′-3′ | Comp. vs. 191-D5-001 | Comp. vs. 191-D5-007 | Biacore $K_D$ [nM] | SEQ ID NO : |
|---|---|---|---|---|---|---|
| 191-D5-001 | 39 | AGCGUGGCGAGGUUAGGGCUAGAAGUCGGUCGACACGCU | | < | 0.73 | 96 |
| | | | | | | |
| 191-D5-002 | 37 | GCGUGGCGAGGUUAGGGCUAGAAGUCGGUCGACACGC | = | | | 115 |
| 191-D5-003 | 35 | CGUGGCGAGGUUAGGGCUAGAAGUCGGUCGACACG | = | | | 116 |
| 191-D5-004 | 33 | CG-GGCGAGGUUAGGGCUAGAAGUCGGUCGAC-CG | < | | | 117 |
| 191-D5-005 | 33 | CG-GGCGAGGUUAGGGCUAGAAGUCGGUCGCC-CG | = | | | 118 |
| 191-D5-006 | 31 | CG--GCGAGGUUAGGGCUAGAAGUCGGUCGC--CG | = | | | 119 |
| 191-D5-007 | 29 | CG--G-GAGGUUAGGGCUAGAAGUCGGUC-C--CG | + | | 0.75 | 120 |
| 191-D5-010 | 27 | G--G-GAGGUUAGGGCUAGAAGUCGGUC-C--C | | < | | 121 |

terminal nucleotides at the 5′- and the 3′-end that may hybridize to each other (bold) nt.:= nucleotides nucleotides which may mainly comprise a SDF-binding motif (boxed) =:= equal binding affinity as 191-D5-001/ -007

</<</<<<:= weaker (<), much weaker (<<) or very much weaker (<<<) binding affinity than 191-D5-001/ -007

Comp.:= Clones were tested as aptamers in a competition binding assay vs. 191-D5-001 or 191-D5-007 whereas both clones have the identical binding affinity to SDF-1 as 191-D5-001

Fig. 7A

Derivatives of Type C SDF Binding Nucleic Acid 191-D5-001

| Name | nt. | Sequence: 5′-3′ | Comp. vs. 191-D5-007 | SEQ ID NO : |
|---|---|---|---|---|
| 191-D5-007 | 29 | **CG--G-GA**GGUUAGGGCUAGAAGUCGG**UC-C--CG** | | 120 |
| 191-D5-010 | 27 | **G--G-GA**GGUUAGGGCUAGAAGUCGG**UC-C--C** | < | 121 |
| | | | | |
| 191-D5-017 | 27 | **CCGC**GGUUAGGGCUAGAAGUCGG**GCGG** | < | 122 |
| 191-D5-029 | 27 | **CCCG**GGUUAGGGCUAGAAGUCGG**CGGG** | < | 123 |
| 191-D5-024 | 27 | **GGCG**GGUUAGGGCUAGAAGUCGG**CGCC** | < | 124 |
| 191-D5-017-29a | 29 | **CCCGC**GGUUAGGGCUAGAAGUCGG**GCGGG** | < | 125 |
| 191-D5-017-29b | 29 | **GCCGC**GGUUAGGGCUAGAAGUCGG**GCGGC** | < | 126 |
| 191-D5-019-29a | 29 | **CCCCG**GGUUAGGGCUAGAAGUCGG**CGGGG** | < | 127 |
| 191-D5-024-29a | 29 | **CGGCG**GGUUAGGGCUAGAAGUCGG**CGCCG** | = | 128 |
| 191-D5-024-29b | 29 | **GGGCG**GGUUAGGGCUAGAAGUCGG**CGCCC** | = | 129 |

terminal nucleotides at the 5′- and the 3′-end that may hybridize to each other (bold) nt.:= nucleotides nucleotides which may mainly comprise a SDF-binding motif =:= equal binding affinity as 191-D5-007

</<</<<<:= weaker (<), much weaker (<<) or very much weaker (<<<) binding affinity than 191-D5-007

Comp.:= Clones were tested as aptamers in a competition binding assay vs. 191-D5-007

Fig. 7B

Derivatives of Type C SDF Binding Nucleic Acid 197-B2

| Name | nt. | Sequence: 5′-3′ | Comp.vs. 197-B2 | Comp. vs. 191-D5-007 | TAX $IC_{50}$ [nM] | SEQ ID NO: |
|---|---|---|---|---|---|---|
| 197-B2 | 39 | **GUGCUGCGGG**GGUUAGGGCUAGAAGUCGG**CCUGCAGCAC** | | = | 0.1-0.2 | 95 |
| 197-B2-001 | 37 | **UGCUGCGGG**GGUUAGGGCUAGAAGUCGG**CCUGCAGCA** | = | | | 130 |
| 197-B2-002 | 35 | **GCUGCGGG**GGUUAGGGCUAGAAGUCGG**CCUGCAGC** | = | | | 131 |
| 197-B2-003 | 33 | **CUGCGGG**GGUUAGGGCUAGAAGUCGG**CCUGCAG** | = | | | 132 |
| 197-B2-004 | 31 | **UGCGGG**GGUUAGGGCUAGAAGUCGG**CCUGCA** | = | | | 133 |
| 197-B2-005 | 29 | **GCGGG**GGUUAGGGCUAGAAGUCGG**CCUGC** | = | | | 134 |
| 197-B2-006 | 29 | **GCCGG**GGUUAGGGCUAGAAGUCGG**CCGGC** | = | = | 0.1-0.2 | 135 |
| 197-B2-006-31a | 31 | **GGCCGG**GGUUAGGGCUAGAAGUCGG**CCGGCC** | | = | | 136 |
| 197-B2-006-31b | 31 | **CGCCGG**GGUUAGGGCUAGAAGUCGG**CCGGCG** | | = | | 137 |

terminal nucleotides at the 5′- and the 3′-end that may hybridize to each other (bold) nt.:= nucleotides nucleotides which may mainly comprise a SDF-binding motif i.a.:= inactive =:= equal binding affinity as 197-B2 or 191-D5-007

</<</<<<:= weaker (<), much weaker (<<) or very much weaker (<<<) binding affinity than as 197-B2 or 191-D5-007

Comp.:= Clones were tested as aptamers in a competition binding assay vs. 197-B2 or 191-D5-007 whereas both clones have the identical binding affinity to SDF-1

TAX:= Clones were tested as Spiegelmers in a cell culture *in vitro* chemotaxis assay

Fig. 8

Other SDF-1 Binding Nucleic Acids (Type D SDF-1 Binding Nucleic Acids)

| Name | nt. | Sequence: 5'-3' | PD $K_D$ [nM] | SEQ ID NO: |
|---|---|---|---|---|
| 194-A2-001 | 48 | **CGUGG**UCCGUUGUGUCAGGUCUAUUCGCCCCGGUGCAGGGCAU**CCGCG** | 12.0 | 142 |
| 196-B12-003 | 49 | GCAGUGUGACGCGGACGUGAUAGGACAGAGCUGAUCCCGCUCAGGUGAG | 7.6 | 143 |
| 196-B12-004 | 49 | CAACAGCAGUGUGACGCGGACGUGAUAGGACAGAGCUGAUCCCGCUCAG | 5.3 | 144 |

terminal nucleotides at the 5'- and the 3'-end that may hybridize to each other (bold) nt.:= nucleotides

PD.:= Clones were tested as aptamers in a pull-down binding assay

Fig. 9

A
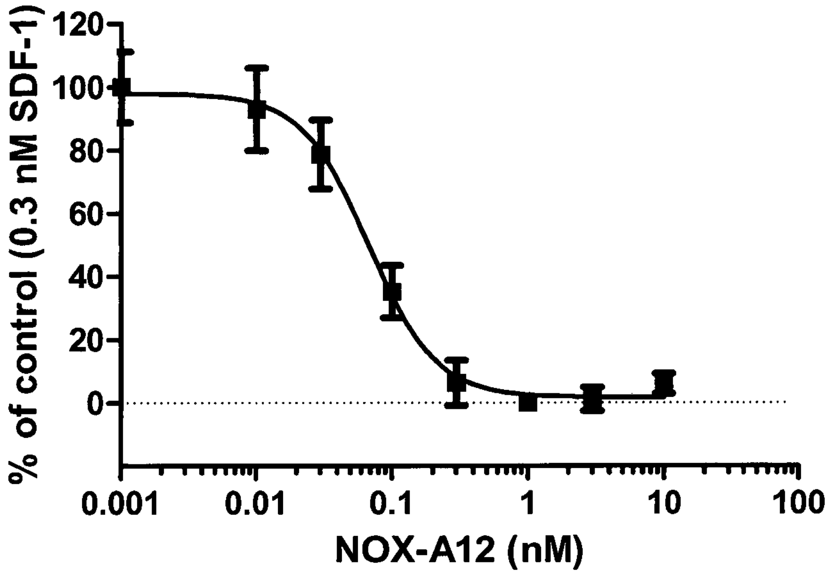
B
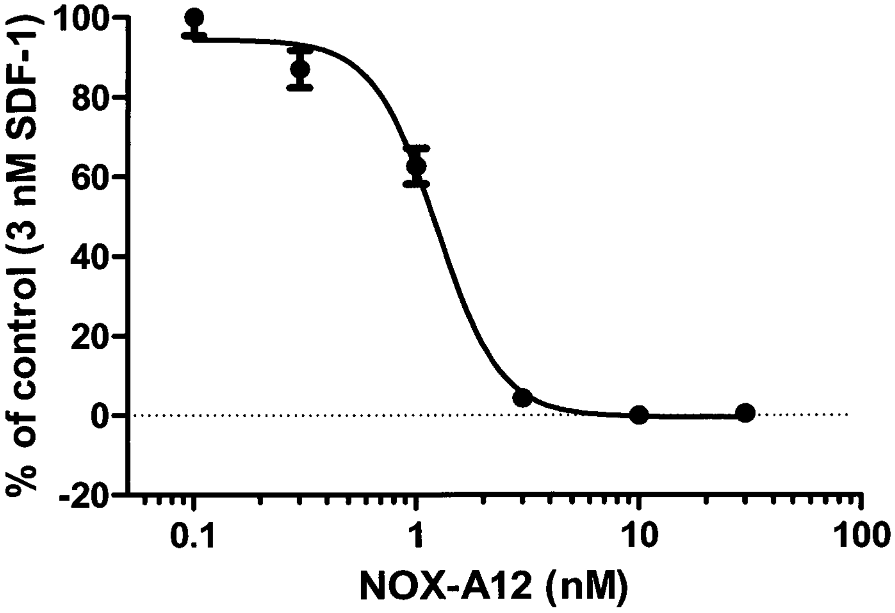
Fig. 11

SEQUENCE LISTING

<160> NUMBER OF SEQ ID NOS: 225

<210> SEQ ID NO 1
<211> LENGTH: 68
<212> TYPE: PRT
<213> ORGANISM: Homo sapiens
<220> FEATURE:
<221> NAME/KEY: misc_feature
<223> OTHER INFORMATION: L-peptide

<400> SEQUENCE: 1

```
Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65
```

<210> SEQ ID NO 2
<211> LENGTH: 72
<212> TYPE: PRT
<213> ORGANISM: Homo sapiens
<220> FEATURE:
<221> NAME/KEY: misc_feature
<223> OTHER INFORMATION: L-peptide

<400> SEQUENCE: 2

```
Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Phe Lys Met
65                  70
```

<210> SEQ ID NO 3
<211> LENGTH: 68
<212> TYPE: PRT
<213> ORGANISM: Mus musculus
<220> FEATURE:
<221> NAME/KEY: misc_feature
<223> OTHER INFORMATION: L-peptide

<400> SEQUENCE: 3

```
Lys Pro Val Ser Leu Ser Tyr Arg Cys Pro Cys Arg Phe Phe Glu Ser
1               5                   10                  15

His Ile Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65
```

<210> SEQ ID NO 4
<211> LENGTH: 71
<212> TYPE: PRT
<213> ORGANISM: Homo sapiens
<220> FEATURE:
<221> NAME/KEY: misc_feature
<223> OTHER INFORMATION: D-peptide
<220> FEATURE:
<221> NAME/KEY: misc_feature
<223> OTHER INFORMATION: biotinylated at C-terminus

<400> SEQUENCE: 4

```
Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Phe Lys
65                  70
```

<210> SEQ ID NO 5
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 5
agcguggugu gaucuagaug uaguggcuga uccuagucag guacgcu 47

<210> SEQ ID NO 6
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 6
agcguggugu gaucuagaug uauuggcuga uccuagucag guacgcu 47

<210> SEQ ID NO 7
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 7
agcguggugu gaucuagaug uaauggcuga uccuagucag gugcgcu 47

<210> SEQ ID NO 8
<211> LENGTH: 45
<212> TYPE: DNA

<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 8
gcgaggugug aucuagaugu aguggcugau ccuagucagg ugcgc 45

<210> SEQ ID NO 9
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 9
gcguggugug aucuagaugu aguggcugau ccuagucagg ugcgc 45

<210> SEQ ID NO 10
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 10
gcauggugug aucuagaugu aguggcugau ccuagucagg ugccc 45

<210> SEQ ID NO 11
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 11
gcguggugug aucuagaugu aauggcugau ccuagucagg gacgc 45

<210> SEQ ID NO 12
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 12
gcguggugug aucuagaugu agaggcugau ccuagucagg uacgc 45

<210> SEQ ID NO 13
<211> LENGTH: 45
<212> TYPE: DNA
<213> ORGANISM: artificial
<220> FEATURE:
<223> OTHER INFORMATION: synthetic
<220> FEATURE:

<221> NAME/KEY: misc_feature
<223> OTHER INFORMATION: L-RNA

<400> SEQUENCE: 13
gcguggugug aucuagaugu aaaggcugau ccuagucagg uacgc 45

<210> SEQ ID NO 14
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 14
gcguggugug aucuagaugu aguggcuguu ccuagucagg uaugc 45

<210> SEQ ID NO 15
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 15
gcguggugug aucuagaugu aguggcugau ccuaguuagg uacgc 45

<210> SEQ ID NO 16
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 16
gcguggugug aucuagaugu aguggcugau ccuagucagg uacgc 45

<210> SEQ ID NO 17
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 17
cgugguguga ucuagaugua guggcugauc cuagucaggu acg 43

<210> SEQ ID NO 18
<211> LENGTH: 41
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 18
guggugugau cuagauguag uggcugaucc uagucaggua c 41

<210> SEQ ID NO 19
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 19
uggugugauc uagauguagu ggcugauccu agucaggua 39

<210> SEQ ID NO 20
<211> LENGTH: 37
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 20
ggugugaucu agauguagug gcugauccua gucaggu 37

<210> SEQ ID NO 21
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 21
gugugaucua gauguagugg cugauccuag ucagg 35

<210> SEQ ID NO 22
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 22
gcguggugug aucuagaugu auuggcugau ccuagucagg uacgc 45

<210> SEQ ID NO 23
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 23
gcgcggugug aucuagaugu auuggcugau ccuagucagg cgcgc 45

<210> SEQ ID NO 24
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 24
gcgcguguga ucuagaugua uuggcugauc cuagucaggg cgc 43

<210> SEQ ID NO 25
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 25
gggcguguga ucuagaugua uuggcugauc cuagucaggg ccc 43

<210> SEQ ID NO 26
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 26
ggccguguga ucuagaugua uuggcugauc cuagucaggg gcc 43

<210> SEQ ID NO 27
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 27
gcccguguga ucuagaugua uuggcugauc cuagucaggg ggc 43

<210> SEQ ID NO 28
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (1)..(1)
<223> OTHER INFORMATION: 40 kDa-PEG-moiety attached to 5'-end

<400> SEQUENCE: 28
gcguggugug aucuagaugu auuggcugau ccuagucagg uacgc 45

<210> SEQ ID NO 29
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 29
agcguggugu gaucuagaug uaguggcuga uccuagucag guacgcu 47

<210> SEQ ID NO 30
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 30
agcguggugu gaucuagaug uauuggcuga uccuagucag guacgcu 47

<210> SEQ ID NO 31
<211> LENGTH: 47
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 31
agcguggugu gaucuagaug uaauggcuga uccuagucag gugcgcu 47

<210> SEQ ID NO 32
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 32
gcgaggugug aucuagaugu aguggcugau ccuagucagg ugcgc 45

<210> SEQ ID NO 33
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 33
gcguggugug aucuagaugu aguggcugau ccuagucagg ugcgc 45

<210> SEQ ID NO 34
<211> LENGTH: 45
<212> TYPE: DNA
<213> ORGANISM: artificial

<220> FEATURE:
<223> OTHER INFORMATION: synthetic
<220> FEATURE:
<221> NAME/KEY: misc_feature
<223> OTHER INFORMATION: D-RNA

<400> SEQUENCE: 34
gcauggugug aucuagaugu aguggcugau ccuagucagg ugccc 45

<210> SEQ ID NO 35
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 35
gcguggugug aucuagaugu aauggcugau ccuagucagg gacgc 45

<210> SEQ ID NO 36
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 36
gcguggugug aucuagaugu agaggcugau ccuagucagg uacgc 45

<210> SEQ ID NO 37
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 37
gcguggugug aucuagaugu aaaggcugau ccuagucagg uacgc 45

<210> SEQ ID NO 38
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 38
gcguggugug aucuagaugu aguggcuguu ccuagucagg uaugc 45

<210> SEQ ID NO 39
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature

<223> OTHER INFORMATION: D-RNA

<400> SEQUENCE: 39
gcguggugug aucuagaugu aguggcugau ccuaguuagg uacgc 45

<210> SEQ ID NO 40
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 40
gcguggugug aucuagaugu aguggcugau ccuagucagg uacgc 45

<210> SEQ ID NO 41
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 41 cguggguga ucuagaugua guggcugauc cuagucaggu acg 43

<210> SEQ ID NO 42
<211> LENGTH: 41
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 42
guggugugau cuagauguag uggcugaucc uagucaggua c 41

<210> SEQ ID NO 43
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 43
uggugugauc uagauguagu ggcugauccu agucaggua 39

<210> SEQ ID NO 44
<211> LENGTH: 37
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 44
ggugugaucu agauguagug gcugauccua gucaggu 37

<210> SEQ ID NO 45
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 45
gugugaucua gauguagugg cugauccuag ucagg 35

<210> SEQ ID NO 46
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 46
gcguggugug aucuagaugu auuggcugau ccuagucagg uacgc 45

<210> SEQ ID NO 47
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 47
gcgcggugug aucuagaugu auuggcugau ccuagucagg cgcgc 45

<210> SEQ ID NO 48
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 48
gcgcguguga ucuagaugua uuggcugauc cuagucaggg cgc 43

<210> SEQ ID NO 49
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 49
gggcguguga ucuagaugua uuggcugauc cuagucaggg ccc 43

<210> SEQ ID NO 50

<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 50
ggccguguga ucuagaugua uuggcugauc cuagucaggg gcc 43

<210> SEQ ID NO 51
<211> LENGTH: 43
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 51
gcccguguga ucuagaugua uuggcugauc cuagucaggg ggc 43

<210> SEQ ID NO 52
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 52
gugugaucua gauguadwgg cugwuccuag uyagg 35

<210> SEQ ID NO 53
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 53
gugugaucua gauguadugg cugauccuag ucagg 35

<210> SEQ ID NO 54
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 54
aaaguaacac guaaaaugaa agguaac 27

<210> SEQ ID NO 55
<211> LENGTH: 26
<212> TYPE: DNA
<213> ORGANISM: artificial
<220> FEATURE:

-continued

<223> OTHER INFORMATION: synthetic
<220> FEATURE:
<221> NAME/KEY: misc_feature
<223> OTHER INFORMATION: L-RNA

<400> SEQUENCE: 55
aaagcaacau gucaaugaaa gguagc 26

<210> SEQ ID NO 56
<211> LENGTH: 18
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 56
gguuagggcu aaagucgg 18

<210> SEQ ID NO 57
<211> LENGTH: 19
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 57
gguuagggcu agaagucgg 19

<210> SEQ ID NO 58
<211> LENGTH: 19
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 58
gguuagggcu cgaagucgg 19

<210> SEQ ID NO 59
<211> LENGTH: 19
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 59
gguuagggcu ugaagucgg 19

<210> SEQ ID NO 60
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 60
gcugugaaag caacauguca augaaaggua gccgcagc 38

<210> SEQ ID NO 61
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 61
gcugugaaag uaacauguca augaaaggua accacagc 38

<210> SEQ ID NO 62
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 62
gcugugaaag uaacacguca augaaaggua accgcagc 38

<210> SEQ ID NO 63
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 63
gcugugaaag uaacacguca augaaaggua accacagc 38

<210> SEQ ID NO 64
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 64
gcuguaaaag uaacauguca augaaaggua acuacagc 38

<210> SEQ ID NO 65
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 65
gcuguaaaag uaacaaguca augaaaggua acuacagc 38

<210> SEQ ID NO 66
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 66
gcugugaaag uaacaaguca augaaaggua accacagc 38

<210> SEQ ID NO 67
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 67
gcagugaaag uaacauguca augaaaggua accacagc 38

<210> SEQ ID NO 68
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 68
gcugugaaag uaacauguca augaaaggua accacugc 38

<210> SEQ ID NO 69
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 69
gcuaugaaag uaacauguca augaaaggua accauagc 38

<210> SEQ ID NO 70
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 70
gcugcgaaag cgacauguca augaaaggua gccgcagc 38

<210> SEQ ID NO 71
<211> LENGTH: 38

<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 71
gcugugaaag caacauguca augaaaggua gccacagc 38

<210> SEQ ID NO 72
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 72
gcugugaaag uaacauguca augaaaggua gccgcagc 38

<210> SEQ ID NO 73
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 73
agcgugaaag uaacacguaa aaugaaaggu aaccacgcu 39

<210> SEQ ID NO 74
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (16)..(16)
<223> OTHER INFORMATION: a or absent

<400> SEQUENCE: 74
aaagyracah gumaaaugaa agguarc 27

<210> SEQ ID NO 75
<211> LENGTH: 26
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 75
aaagyracah gumaaugaaa gguarc 26

<210> SEQ ID NO 76
<211> LENGTH: 27

<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 76
aaagyracah gumaaaugaa agguarc 27

<210> SEQ ID NO 77
<211> LENGTH: 26
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 77
aaagyaacah gucaaugaaa gguarc 26

<210> SEQ ID NO 78
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 78
cugugaaagc aacaugucaa ugaaagguag ccgcag 36

<210> SEQ ID NO 79
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 79
ugugaaagca acaugucaau gaaagguagc cgca 34

<210> SEQ ID NO 80
<211> LENGTH: 32
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 80
gugaaagcaa caugucaaug aaagguagcc gc 32

<210> SEQ ID NO 81
<211> LENGTH: 30
<212> TYPE: DNA
<213> ORGANISM: artificial
<220> FEATURE:
<223> OTHER INFORMATION: synthetic -continued
<220> FEATURE:
<221> NAME/KEY: misc_feature
<223> OTHER INFORMATION: L-RNA

<400> SEQUENCE: 81
ugaaagcaac augucaauga aagguagccg 30

<210> SEQ ID NO 82
<211> LENGTH: 28
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 82
gaaagcaaca ugucaaugaa agguagcc 28

<210> SEQ ID NO 83
<211> LENGTH: 26
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 83
aaagcaacau gucaaugaaa gguagc 26

<210> SEQ ID NO 84
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 84
gcgugaaagc aacaugucaa ugaaagguag ccgcgc 36

<210> SEQ ID NO 85
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 85
gcgcgaaagc aacaugucaa ugaaagguag ccgcgc 36

<210> SEQ ID NO 86
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 86
gcggaaagca acaugucaau gaaagguagc ccgc 34

<210> SEQ ID NO 87
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 87
cgugaaagca acaugucaau gaaagguagc cgcg 34

<210> SEQ ID NO 88
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 88
gcgcaaagca acaugucaau gaaagguagc gugc 34

<210> SEQ ID NO 89
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 89
gugcaaagca acaugucaau gaaagguagc gcgc 34

<210> SEQ ID NO 90
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 90
cgcgaaagca acaugucaau gaaagguagc cgug 34

<210> SEQ ID NO 91
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 91
gggcaaagca acaugucaau gaaagguagc gccc 34

<210> SEQ ID NO 92
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 92
ggccaaagca acaugucaau gaaagguagc ggcc 34

<210> SEQ ID NO 93
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 93
gcccaaagca acaugucaau gaaagguagc gggc 34

<210> SEQ ID NO 94
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 94
ccccaaagca acaugucaau gaaagguagc gggg 34

<210> SEQ ID NO 95
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 95
gugcugcggg gguuagggcu agaagucggc cugcagcac 39

<210> SEQ ID NO 96
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 96
agcguggcga gguuagggcu agaagucggu cgacacgcu 39

<210> SEQ ID NO 97
<211> LENGTH: 39
<212> TYPE: DNA

<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 97
guguugcgga gguuagggcu agaagucggu cagcagcac                39

<210> SEQ ID NO 98
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 98
cgugcggccu aagagguuag ggcuuaaagu cggucuuugg ccaacacg     48

<210> SEQ ID NO 99
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 99
cgugcgcuug agauaggggu uagggcuuaa agucggcuga uucucacg     48

<210> SEQ ID NO 100
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 100
cgugauuggu gagggguuag ggcuugaagu cggccuuguc cagucacg     48

<210> SEQ ID NO 101
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 101
agcgugaagg gguuagggcu cgaagucggc ugacacgcu              39

<210> SEQ ID NO 102
<211> LENGTH: 39
<212> TYPE: DNA
<213> ORGANISM: artificial
<220> FEATURE:
<223> OTHER INFORMATION: synthetic
<220> FEATURE:

<221> NAME/KEY: misc_feature
<223> OTHER INFORMATION: L-RNA

<400> SEQUENCE: 102
gugcugcggg gguuagggcu cgaagucggc ccgcagcac 39

<210> SEQ ID NO 103
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 103
guguucccgg gguuagggcu ugaagucggc cggcagcac 39

<210> SEQ ID NO 104
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 104
guguugcagg gguuagggcu ugaagucggc cugcagcac 39

<210> SEQ ID NO 105
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 105
gugcugcggg gguuagggcu caaagucggc cugcagcac 39

<210> SEQ ID NO 106
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 106
gugcugccgg gguuagggcu aaagucggcc gacagcac 38

<210> SEQ ID NO 107
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 107
gugcuguggg ggucagggcu agaagucggc cugcagcac 39

<210> SEQ ID NO 108
<211> LENGTH: 19
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (13)..(13)
<223> OTHER INFORMATION: A or absent

<400> SEQUENCE: 108
gguyagggcu hraagucgg 19

<210> SEQ ID NO 109
<211> LENGTH: 19
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 109
gguyagggcu hraagucgg 19

<210> SEQ ID NO 110
<211> LENGTH: 18
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 110
gguyagggcu hragucgg 18

<210> SEQ ID NO 111
<211> LENGTH: 19
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 111
gguuagggcu hgaagucgg 19

<210> SEQ ID NO 112
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 112
ugagauaggg guuagggcuu aaagucggcu gauucuca 38

<210> SEQ ID NO 113
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 113
gagauagggg uuagggcuua aagucggcug auucuc 36

<210> SEQ ID NO 114
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 114
gggguuaggg cuuaaagucg gcugauucu 29

<210> SEQ ID NO 115
<211> LENGTH: 37
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 115
gcguggcgag guuagggcua gaagucgguc gacacgc 37

<210> SEQ ID NO 116
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 116
cguggcgagg uuagggcuag aagucggucg acacg 35

<210> SEQ ID NO 117
<211> LENGTH: 33
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 117
cgggcgaggu uagggcuaga agucggucga ccg 33

<210> SEQ ID NO 118
<211> LENGTH: 33
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 118
cgggcgaggu uagggcuaga agucggucgc ccg 33

<210> SEQ ID NO 119
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 119
cggcgagguu agggcuagaa gucggucgcc g 31

<210> SEQ ID NO 120
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 120
cgggagguua gggcuagaag ucggucccg 29

<210> SEQ ID NO 121
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 121
gggagguuag ggcuagaagu cgguccc 27

<210> SEQ ID NO 122
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 122
ccgcgguuag ggcuagaagu cgggcgg 27

<210> SEQ ID NO 123
<211> LENGTH: 27
<212> TYPE: DNA
<213> ORGANISM: artificial

-continued

<220> FEATURE:
<223> OTHER INFORMATION: synthetic
<220> FEATURE:
<221> NAME/KEY: misc_feature
<223> OTHER INFORMATION: L-RNA

<400> SEQUENCE: 123
cccggguuag ggcuagaagu cggcggg 27

<210> SEQ ID NO 124
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 124
ggcggguuag ggcuagaagu cggcgcc 27

<210> SEQ ID NO 125
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 125
cccgcgguua gggcuagaag ucgggcggg 29

<210> SEQ ID NO 126
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 126
gccgcgguua gggcuagaag ucgggcggc 29

<210> SEQ ID NO 127
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 127
ccccggguua gggcuagaag ucggcgggg 29

<210> SEQ ID NO 128
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature

<223> OTHER INFORMATION: L-RNA

<400> SEQUENCE: 128
cggcggguua gggcuagaag ucggcgccg 29

<210> SEQ ID NO 129
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 129
gggcggguua gggcuagaag ucggcgccc 29

<210> SEQ ID NO 130
<211> LENGTH: 37
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 130
ugcugcgggg guuagggcua gaagucggcc ugcagca 37

<210> SEQ ID NO 131
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 131
gcugcggggg uuagggcuag aagucggccu gcagc 35

<210> SEQ ID NO 132
<211> LENGTH: 33
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 132
cugcgggggu uagggcuaga agucggccug cag 33

<210> SEQ ID NO 133
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 133 ugcgggggsuu agggcuagaa gucggccugc a                                      31

<210> SEQ ID NO 134
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 134
gcggggguua gggcuagaag ucggccugc                                          29

<210> SEQ ID NO 135
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 135 gccggguua gggcuagaag ucggccggc                                           29

<210> SEQ ID NO 136
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 136
ggccgggguu agggcuagaa gucggccggc c                                       31

<210> SEQ ID NO 137
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 137
cgccgggguu agggcuagaa gucggccggc g                                       31

<210> SEQ ID NO 138
<211> LENGTH: 10
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (7)..(7)
<223> OTHER INFORMATION: n is a, c, g, t or u

<400> SEQUENCE: 138 rksbusnvgr 10

<210> SEQ ID NO 139
<211> LENGTH: 10
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (3)..(3)
<223> OTHER INFORMATION: n is a, c, g, t or u

<400> SEQUENCE: 139 yynrcassmy 10

<210> SEQ ID NO 140
<211> LENGTH: 10
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 140 rksbugsvgr 10

<210> SEQ ID NO 141
<211> LENGTH: 10
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (3)..(3)
<223> OTHER INFORMATION: n is a, c, g, t or u

<400> SEQUENCE: 141 ycnrcassmy 10

<210> SEQ ID NO 142
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 142
cgugguccgu ugugucaggu cuauucgccc cggugcaggg cauccgcg 48

<210> SEQ ID NO 143
<211> LENGTH: 49
<212> TYPE: DNA
<213> ORGANISM: artificial
<220> FEATURE:
<223> OTHER INFORMATION: synthetic
<220> FEATURE:
<221> NAME/KEY: misc_feature

<223> OTHER INFORMATION: L-RNA

<400> SEQUENCE: 143
gcagugugac gcggacguga uaggacagag cugaucccgc ucaggugag 49

<210> SEQ ID NO 144
<211> LENGTH: 49
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 144
caacagcagu gugacgcgga cgugauagga cagagcugau cccgcucag 49

<210> SEQ ID NO 145
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (1)..(1)
<223> OTHER INFORMATION: 40 kDa-PEG-moiety attached to 5'-end

<400> SEQUENCE: 145
gcgugaaagc aacaugucaa ugaaagguag ccgcgc 36

<210> SEQ ID NO 146
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 146
gcugugaaag caacauguca augaaaggua gccgcagc 38

<210> SEQ ID NO 147
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 147
gcugugaaag uaacauguca augaaaggua accacagc 38

<210> SEQ ID NO 148
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature -continued

<223> OTHER INFORMATION: D-RNA

<400> SEQUENCE: 148
gcugugaaag uaacacguca augaaaggua accgcagc 38

<210> SEQ ID NO 149
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 149
gcugugaaag uaacacguca augaaaggua accacagc 38

<210> SEQ ID NO 150
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 150
gcuguaaaag uaacauguca augaaaggua acuacagc 38

<210> SEQ ID NO 151
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 151
gcuguaaaag uaacaaguca augaaaggua acuacagc 38

<210> SEQ ID NO 152
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 152
gcugugaaag uaacaaguca augaaaggua accacagc 38

<210> SEQ ID NO 153
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 153
gcagugaaag uaacauguca augaaaggua accacagc 38

<210> SEQ ID NO 154
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 154
gcugugaaag uaacauguca augaaaggua accacugc 38

<210> SEQ ID NO 155
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 155
gcuaugaaag uaacauguca augaaaggua accauagc 38

<210> SEQ ID NO 156
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 156
gcugcgaaag cgacauguca augaaaggua gccgcagc 38

<210> SEQ ID NO 157
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 157
gcugugaaag caacauguca augaaaggua gccacagc 38

<210> SEQ ID NO 158
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 158
gcugugaaag uaacauguca augaaaggua gccgcagc 38

<210> SEQ ID NO 159

<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 159
agcgugaaag uaacacguaa aaugaaaggu aaccacgcu 39

<210> SEQ ID NO 160
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 160
cugugaaagc aacaugucaa ugaaagguag ccgcag 36

<210> SEQ ID NO 161
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 161
ugugaaagca acaugucaau gaaagguagc cgca 34

<210> SEQ ID NO 162
<211> LENGTH: 32
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 162
gugaaagcaa caugucaaug aaagguagcc gc 32

<210> SEQ ID NO 163
<211> LENGTH: 30
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 163
ugaaagcaac augucaauga aagguagccg 30

<210> SEQ ID NO 164
<211> LENGTH: 28
<212> TYPE: DNA
<213> ORGANISM: artificial
<220> FEATURE:

-continued

<223> OTHER INFORMATION: synthetic
<220> FEATURE:
<221> NAME/KEY: misc_feature
<223> OTHER INFORMATION: D-RNA

<400> SEQUENCE: 164
gaaagcaaca ugucaaugaa agguagcc 28

<210> SEQ ID NO 165
<211> LENGTH: 26
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 165
aaagcaacau gucaaugaaa gguagc 26

<210> SEQ ID NO 166
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 166
gcgugaaagc aacaugucaa ugaaagguag ccgcgc 36

<210> SEQ ID NO 167
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 167
gcgcgaaagc aacaugucaa ugaaagguag ccgcgc 36

<210> SEQ ID NO 168
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 168
gcggaaagca acaugucaau gaaagguagc ccgc 34

<210> SEQ ID NO 169
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA -continued

<400> SEQUENCE: 169
cgugaaagca acaugucaau gaaagguagc cgcg 34

<210> SEQ ID NO 170
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 170
gcgcaaagca acaugucaau gaaagguagc gugc 34

<210> SEQ ID NO 171
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 171
gugcaaagca acaugucaau gaaagguagc gcgc 34

<210> SEQ ID NO 172
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 172
cgcgaaagca acaugucaau gaaagguagc cgug 34

<210> SEQ ID NO 173
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 173
gggcaaagca acaugucaau gaaagguagc gccc 34

<210> SEQ ID NO 174
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 174
ggccaaagca acaugucaau gaaagguagc ggcc 34

<210> SEQ ID NO 175
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 175
gcccaaagca acaugucaau gaaagguagc gggc 34

<210> SEQ ID NO 176
<211> LENGTH: 34
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 176
ccccaaagca acaugucaau gaaagguagc gggg 34

<210> SEQ ID NO 177
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 177
gugcugcggg gguuagggcu agaagucggc cugcagcac 39

<210> SEQ ID NO 178
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 178
agcguggcga gguuagggcu agaagucggu cgacacgcu 39

<210> SEQ ID NO 179
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 179
guguugcgga gguuagggcu agaagucggu cagcagcac 39

<210> SEQ ID NO 180
<211> LENGTH: 48

<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 180
cgugcggccu aagagguuag ggcuuaaagu cggucuuugg ccaacacg 48

<210> SEQ ID NO 181
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 181
cgugcgcuug agauaggggu uagggcuuaa agucggcuga uucucacg 48

<210> SEQ ID NO 182
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 182
cgugauuggu gagggguuag ggcuugaagu cggccuuguc cagucacg 48

<210> SEQ ID NO 183
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 183
agcgugaagg gguuagggcu cgaagucggc ugacacgcu 39

<210> SEQ ID NO 184
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 184
gugcugcggg gguuagggcu cgaagucggc ccgcagcac 39

<210> SEQ ID NO 185
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 185
guguucccgg gguuagggcu ugaagucggc cggcagcac 39

<210> SEQ ID NO 186
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 186
guguugcagg gguuagggcu ugaagucggc cugcagcac 39

<210> SEQ ID NO 187
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 187
gugcugcggg gguuagggcu caaagucggc cugcagcac 39

<210> SEQ ID NO 188
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 188
gugcugccgg gguuagggcu aaagucggcc gacagcac 38

<210> SEQ ID NO 189
<211> LENGTH: 39
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 189
gugcuguggg ggucagggcu agaagucggc cugcagcac 39

<210> SEQ ID NO 190
<211> LENGTH: 38
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 190
ugagauaggg guuagggcuu aaagucggcu gauucuca 38

<210> SEQ ID NO 191
<211> LENGTH: 36
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 191
gagauagggg uuagggcuua aagucggcug auucuc 36

<210> SEQ ID NO 192
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 192 ggggguuaggg cuuaaagucg gcugauucu 29

<210> SEQ ID NO 193
<211> LENGTH: 37
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 193
gcguggcgag guuagggcua gaagucgguc gacacgc 37

<210> SEQ ID NO 194
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 194
cguggcgagg uuagggcuag aagucggucg acacg 35

<210> SEQ ID NO 195
<211> LENGTH: 33
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 195
cgggcgaggu uagggcuaga agucggucga ccg 33

<210> SEQ ID NO 196
<211> LENGTH: 33
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 196
cgggcgaggu uagggcuaga agucggucgc ccg 33

<210> SEQ ID NO 197
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 197
cggcgagguu agggcuagaa gucggucgcc g 31

<210> SEQ ID NO 198
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 198
cgggagguua gggcuagaag ucggucccg 29

<210> SEQ ID NO 199
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 199
gggagguuag ggcuagaagu cgguccc 27

<210> SEQ ID NO 200
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 200
ccgcgguuag ggcuagaagu cgggcgg 27

<210> SEQ ID NO 201
<211> LENGTH: 27
<212> TYPE: DNA

<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 201
cccggguuag ggcuagaagu cggcggg 27

<210> SEQ ID NO 202
<211> LENGTH: 27
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 202
ggcggguuag ggcuagaagu cggcgcc 27

<210> SEQ ID NO 203
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 203
cccgcgguua gggcuagaag ucgggcggg 29

<210> SEQ ID NO 204
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 204
gccgcgguua gggcuagaag ucgggcggc 29

<210> SEQ ID NO 205
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 205
ccccggguua gggcuagaag ucggcgggg 29

<210> SEQ ID NO 206
<211> LENGTH: 29
<212> TYPE: DNA
<213> ORGANISM: artificial
<220> FEATURE:
<223> OTHER INFORMATION: synthetic
<220> FEATURE:

<221> NAME/KEY: misc_feature
<223> OTHER INFORMATION: D-RNA

<400> SEQUENCE: 206
cggcggguua gggcuagaag ucggcgccg 29

<210> SEQ ID NO 207
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 207 gggcgggua gggcuagaag ucggcgccc 29

<210> SEQ ID NO 208
<211> LENGTH: 37
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 208
ugcugcgggg guuagggcua gaagucggcc ugcagca 37

<210> SEQ ID NO 209
<211> LENGTH: 35
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 209
gcugcggggg uuagggcuag aagucggccu gcagc 35

<210> SEQ ID NO 210
<211> LENGTH: 33
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 210
cugcgggggu uagggcuaga agucggccug cag 33

<210> SEQ ID NO 211
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 211
ugcggggguu agggcuagaa gucggccugc a						31

<210> SEQ ID NO 212
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 212
gcggggguua gggcuagaag ucggccugc						29

<210> SEQ ID NO 213
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 213
gccgggguua gggcuagaag ucggccggc						29

<210> SEQ ID NO 214
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 214
ggccgggguu agggcuagaa gucggccggc c						31

<210> SEQ ID NO 215
<211> LENGTH: 31
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 215
cgccgggguu agggcuagaa gucggccggc g						31

<210> SEQ ID NO 216
<211> LENGTH: 48
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 216
cgugguccgu ugugucaggu cuauucgccc cggugcaggg cauccgcg						48

<210> SEQ ID NO 217
<211> LENGTH: 49
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 217
gcagugugac gcggacguga uaggacagag cugaucccgc ucaggugag 49

<210> SEQ ID NO 218
<211> LENGTH: 49
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: D-RNA

<400> SEQUENCE: 218
caacagcagu gugacgcgga cgugauagga cagagcugau cccgcucag 49

<210> SEQ ID NO 219
<211> LENGTH: 40
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (1)..(1)
<223> OTHER INFORMATION: 40 kDa-PEG-moiety attached to 5'-end

<400> SEQUENCE: 219
uaaggaaacu cggucugaug cgguagcgcu gugcagagcu 40

<210> SEQ ID NO 220
<211> LENGTH: 17
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 220
cgugcgcuug agauagg 17

<210> SEQ ID NO 221
<211> LENGTH: 12
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 221
cugauucuca cg 12

-continued

```
<210> SEQ ID NO 222
<211> LENGTH: 10
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA

<400> SEQUENCE: 222

cugauucuca                                                            10


<210> SEQ ID NO 223
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (1)..(1)
<223> OTHER INFORMATION: 40 kDa-PEG-moiety attached to 5'-end

<400> SEQUENCE: 223

gccggggwuua gggcuagaag ucggccggc                                      29


<210> SEQ ID NO 224
<211> LENGTH: 29
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (1)..(1)
<223> OTHER INFORMATION: 40 kDa-PEG-moiety attached to 5'-end

<400> SEQUENCE: 224

cgggagguua gggcuagaag ucggucccg                                       29


<210> SEQ ID NO 225
<211> LENGTH: 45
<212> TYPE: DNA
<213> ORGANISM: artificial
<220> FEATURE:
<223> OTHER INFORMATION: synthetic
<220> FEATURE:
<221> NAME/KEY: misc_feature
<223> OTHER INFORMATION: L-RNA
<220> FEATURE:
<221> NAME/KEY: misc_feature
<222> LOCATION: (1)..(1)
<223> OTHER INFORMATION: 40 kDa-PEG-moiety attached to 5'-end

<400> SEQUENCE: 225

cgcauggacu gauccuaguc gguuauguag aucuagugug gugcg                     45
```

METHOD OF MODULATING THE NUMBER AND THE DISTRIBUTION OF TUMOR-INFILTRATING LEUKOCYTES IN TUMORS

The present invention is related to molecules binding to the CXC chemokine stromal cell-derived factor-1 (SDF-1) thereby modulating the number and the distribution of tumor-infiltrating leukocytes in tumors, to molecules capable of inhibiting signaling between SDF-1 and CXCR4 and/or CXCR7 for use in a method for the treatment of a disease, preferably a tumor and/or metastases, wherein in such method said molecules modulate the number and/or the spatial distribution of tumor-infiltrating leukocytes in and/or around the tumor and/or metastases, establish an SDF-1 gradient, induce leukocyte mediated immune response against the tumor and/or the metastases, and/or promote lymphocyte activity in the tumor and/or metastases; a pharmaceutical composition comprising such molecules, and the use of such pharmaceutical composition in the treatment of a disease, preferably a tumor and/or metastases, wherein the treatment of the disease involves modulating the number and/or the spatial distribution of tumor-infiltrating leukocytes in and/or around the tumor and/or metastases, establishing an SDF-1 gradient, inducing leukocyte mediated immune response against the tumor and/or the metastases, and/or promoting lymphocyte activity in the tumor and/or metastases, each caused by or involving such molecules; a medicament comprising such molecules, and the use of such medicament in the treatment of a disease, preferably a tumor and/or metastases, wherein the treatment of the disease involves modulating the number and/or the spatial distribution of tumor-infiltrating leukocytes in and/or around the tumor and/or metastases, establishing an SDF-1 gradient, inducing leukocyte mediated immune response against the tumor and/or the metastases, and/or promoting lymphocyte activity in the tumor and/or metastases, each caused by or involving such molecules; methods for the treatment of tumors and metastases using such molecules, wherein treatment involves modulating the number and/or the spatial distribution of tumor-infiltrating leukocytes in and/or around the tumor and/or metastases, establishing an SDF-1 gradient, inducing leukocyte mediated immune response against the tumor and/or the metastases, and/or promoting lymphocyte activity in the tumor and/or metastases, each caused by or involving such molecules; and their use in the manufacture of a medicament.

Stromal-cell derived factor 1 (abbr.: SDF-1; synonyms, CXCL12; PBSF [pre-B-cell growth-stimulating factor]; TPAR-1 [TPA repressed gene 1]; SCYB12; TLSF [thymic lymphoma cell stimulating factor]; hIRH [human intercrine reduced in hepatomas]) is an angiogenic CXC-motif chemokine that does not contain the ELR motif typical of the IL-8-like chemokines (Salcedo, Wasserman et al. 1999; Salcedo and Oppenheim 2003) but binds and activates the G-protein coupled receptor CXCR4. As a result of alternative splicing, there are further forms of SDF-1, such as SDF-1α (68 amino acids, SEQ ID NO: 1) and SDF-1β (SEQ ID NO: 2), which, compared to SDF-1α carries five additional amino acids at the C-terminus (Shirozu, Nakano et al. 1995).

The amino acid sequence conservation between SDF-1 from different species is remarkable: Human SDF-1α (SEQ.ID. 1) and murine SDF-1α (SEQ ID NO: 3) are virtually identical. There is only a single conservative change of V to I at position 18 (Shirozu, Nakano et al. 1995).

Since the SDF-1 receptor CXCR4 is widely expressed on leukocytes, mature dendritic cells, endothelial cells, brain cells, and megakaryocytes, the activities of SDF-1 are pleiotropic. This chemokine, more than any other identified thus far, exhibits the widest range of biological functions. The most significant functional effects of SDF-1 are:

- Homing and attachment of epithelial cells to neovascular sites in the choroid portion of the retina;
- SDF-1 is required to maintain stem cells and progenitor cells, e.g. hematopoietic progenitor (usually $CD34^+$) cells in the bone marrow of the adult;
- SDF-1 supports proliferation of pre-B cells and augments the growth of bone marrow B cell progenitors and it induces specific migration of pre- and pro-B cells, while not acting as a significant chemoattractant for mature B cells;
- SDF-1 is one of the most efficacious T cell chemoattractants; and
- SDF-1 and its receptor CXCR4 are essential for embryonic development.

Altered expression levels of SDF-1 or its receptor CXCR4 or altered responses towards those molecules are said to be associated with many human diseases, such as retinopathy (Brooks, Caballero et al. 2004; Butler, Guthrie et al. 2005; Meleth, Agron et al. 2005); cancer of breast (Muller, Homey et al. 2001; Cabioglu, Sahin et al. 2005), ovaries (Scotton, Wilson et al. 2002), pancreas (Koshiba, Hosotani et al. 2000), thyroid (Hwang, Chung et al. 2003) andnasopharynx (Wang, Wu et al. 2005); glioma (Zhou, Larsen et al. 2002); neuroblastoma (Geminder, Sagi-Assif et al. 2001); B cell chronic lymphocytic leukemia (Burger, Tsukada et al. 2000); WHIM syndrome (WHIM is an abbreviation for Warts, Hypogammaglobulinemia, Infections, Myelokathexis syndrome) (Gulino, Moratto et al. 2004; Balabanian, Lagane et al. 2005b; Kawai, Choi et al. 2005); immunologic deficiency syndromes (Arya, Ginsberg et al. 1999; Marechal, Arenzana-Seisdedos et al. 1999; Soriano, Martinez et al. 2002); pathologic neovascularization (Salvucci, Yao et al. 2002; Yamaguchi, Kusano et al. 2003; Grunewald, Avraham et al. 2006); inflammation (Murdoch 2000; Fedyk, Jones et al. 2001; Wang, Guan et al. 2001); multiple sclerosis (Krumbholz, Theil et al. 2006); rheumatoid arthritis/osteoarthritis (Buckley, Amft et al. 2000; Kanbe, Takagishi et al. 2002; Grassi, Cristino et al. 2004).

Tumors (including solid and hematological neoplasias and malignancies) are not just masses of cancer cells: infiltration of tumors with immune-cells is a characteristic of cancer. Many human cancers have a complex chemokine network that influences the extent and phenotype of this infiltrate, as well as tumor growth, survival, migration, and angiogenesis. Most solid tumors contain many non-malignant stromal cells. Indeed, stromal cells sometimes outnumber cancer cells. The predominant stromal cells that are found in cancers are macrophages, lymphocytes, endothelial cells and fibroblasts.

Cells from different cancer types have different profiles of chemokine-receptor expression, but the SDF-1 receptor CXCR4 is most commonly found in tumor cells of mouse and man: tumor cells from at least 23 different types of human cancers of epithelial, mesenchymal, and haematopoietic origin express CXCR4 (Balkwill 2004) with SDF-1 being the only known ligand for CXCR4. Apart from the bone marrow and secondary lymphoid tissue, where it is constitutively expressed, SDF-1 is found in primary tumor sites in lymphoma (Corcione, Ottonello et al. 2000) and brain tumors of both neuronal and astrocytic lineage. Furthermore, it is present at high levels in ovarian (Scotton, Wilson et al. 2002) and pancreatic cancer (Koshiba, Hosotani et al. 2000) as well as at sites of metastasis in breast (Muller, Homey et al. 2001) and thyroid cancer (Hwang, Chung et al. 2003), neuroblastoma and haematological malignancies (Geminder, Sagi-Assif et al. 2001).

Besides CXCR4 another SDF-1 receptor was identified: RDC1/CXCR7 (Balabanian, Lagane et al. 2005a, Burns, Summers et al. 2006). In vitro and in vivo studies with prostate cancer cell lines suggest that alterations in CXCR7/RDC1 expression are associated with enhanced adhesive and invasive activities in addition to a survival advantage. In vitro and in vivo studies have shown that both receptors for SDF-1, namely CXCR4 and the CXCR7 promote tumor growth, metastatic potential and resistance to (chemotherapy induced) apoptosis in a number of tumors, e.g breast cancer, glioblastomas, ovarian cancer, neuroblastoma, lung cancer colorectal and prostate cancer (Burns et al, 2006; Li et al, 2008; Scotton et al, 2002; Yang et al, 2008; Zagzag et al, 2008).

CXCR4 and CXCR7 expression thus seems to be a general characteristic of several tumours.

Recent developments in cancer therapy include immunotherapy. Immunotherapy is a form of cancer treatment that uses a patient's own immune system to destroy cancer cells. The intention behind immunotherapy is to harness or further enhance the power of the body's own immune system to fight tumor cells. There are different immunotherapy approaches, including:

- cellular therapies involving an approach where a patient's own T-cells are transformed to produce chimeric antigen receptors ("Chimeric antigen receptor T cell (CAR-T) approach"),
- NK cell therapy using expanded autologous or allogeneic NK cells,
- immune checkpoint inhibitors,
- immunomodulators,
- T-cell and NK-cell engagers, (e.g. bispecific antibodies), and
- cancer vaccines.

Immune checkpoint inhibitors have been described as a radical disruptive change in cancer therapy due to the fact that the goal of checkpoint therapy is not to directly kill or damage cancers, or to activate the immune system to attack particular targets on tumor cells, but rather to remove inhibitory pathways that block effective anti-tumor T-cell responses (Sharma and Allison 2015). This approach has been described, using an analogy to automobiles, as "removing the brakes from the immune system".

The general excitement for immunotherapy to fight cancer relates to achievements in proof-of-concept and results showing significant, durable responses in multiple types of cancer, meaning unprecedented percentages of patients, approximately 20%, that are still alive after multiple years (Sharma and Allison 2015). However, while showing promising results for an unprecedented number of patients, the fact remains that currently only a relatively small percentage of patients with certain cancers, such as melanoma and lung cancer, obtain long-term benefits from immune checkpoint inhibitors (Sharma and Allison 2015). There are large groups of patients with these cancer types, for which immune checkpoint inhibitors are already approved, who do not achieve long-term benefits from immune checkpoint inhibitors. In addition, it seems that for some cancer types, such as pancreatic and colorectal cancer, immune checkpoint inhibitors alone cannot achieve meaningful response rates (Brahmer, Tykodi et al. 2012, Sunshine and Taube 2015)).

A prerequisite for all of these therapies is that the immune cells, mainly cytotoxic T cells and NK cells, but also pro-inflammatory macrophages, need access to the tumor in order to get into contact with the tumor cells that shall be attacked and/or removed by them. At the same time it is desirable that immune cells that dampen the attack, e.g. regulatory T cells (Treg), myeloid-derived suppressor cells (MDSC) or macrophages of the M2 type, are attracted at a lower rate than the mentioned cell types or be kept away. This would shift the balance towards a tumor-killing microenvironment. There are several examples in the literature showing a correlation between the infiltration of a tumor with pro-inflammatory cells and prognosis for the patient—especially when immune checkpoint inhibitors are used as part of the therapeutic regimen (Fridman, Pages et al. 2012).

CXC-motif chemokine 12 (CXCL12), also known as stromal cell-derived factor 1 (SDF-1) is a key chemokine that is responsible for the attraction of many types of leukocytes by signaling through the receptor CXC-motif chemokine receptor 4 (CXCR4) and potentially through its alternative receptor CXCR7.

Effective cell based immunotherapy requires physical contact or interaction between the cells used for immunotherapy of malignant cells.

The problem underlying the present invention is to provide a means which specifically interacts with SDF-1 and modulates physical contact or interaction between the cells used for immunotherapy and malignant cells, whereby the means are suitable for the prevention and/or treatment of cancer.

These and other problems underlying the present invention are solved by the subject matter of the attached independent claims. Preferred embodiments may be taken from the dependent claims.

More specifically, the problem underlying the present invention is solved by the subject matter of the following embodiments.

Embodiment 1: A molecule capable of inhibiting signaling between SDF-1 and CXCR4 and/or CXCR7, wherein the molecule is for use in a method of modulating the number and/or the spatial distribution of tumor-infiltrating leukocytes in a tumor and/or metastases.

Embodiment 2: A molecule capable of inhibiting signaling between SDF-1 and CXCR4 and/or CXCR7, wherein the molecule is for use in a method for treatment of a disease, wherein the method comprises modulating the number and/or the spatial distribution of tumor-infiltrating leukocytes in a tumor and/or metastases.

Embodiment 3: The molecule for use according to any one of embodiments 1 to 2, wherein the method comprises inducing leukocyte mediated immune response against the tumor and/or the metastases, wherein preferably leukocyte-mediated immune response comprises direct leukocyte-mediated cytotoxicity and leukocyte-mediated antibody-dependent cellular cytotoxicity.

Embodiment 4: The molecule for use according to any one of embodiments 1 to 3, wherein the method comprises establishing an SDF-1 gradient a) in and/or around the tumor;

b) in and/or around the metastases;

c) around the vasculature of the tumor; and/or d) around the vasculature of the metastases.

Embodiment 5: A molecule capable of inhibiting signaling between SDF-1 and CXCR4 and/or CXCR7, wherein the molecule is for use in a method of establishing an SDF-1 gradient a) in and/or around a tumor;

b) in and/or around metastases;

c) around the vasculature of a tumor; and/or d) around vasculature of metastases.

Embodiment 6: A molecule capable of inhibiting signaling between SDF-1 and CXCR4 and/or CXCR7, wherein the molecule is for use in a method for treatment and/or prevention of a disease, wherein the method comprises establishing an SDF-1 gradient a) in and/or around a tumor;

b) in and/or around metastases;

c) around the vasculature of a tumor; and/or d) around the vasculature of metastases.

Embodiment 7: The molecule for use according to any one of embodiments 6 to 7, wherein the method comprises modulating the number and/or the spatial distribution of tumor-infiltrating leukocytes in and/or around the tumor and/or metastates, wherein, preferably, such modulation of the number and/or the spatial distribution results from the SDF-1 gradient.

Embodiment 8: The molecule for use according to any one of embodiments 6 to 8, wherein the method comprises inducing leukocyte mediated immune response against the tumor and/or the metastases, wherein preferably leukocyte-mediated immune response comprises direct leukocyte-mediated cytotoxicity and leukocyte-mediated antibody-dependent cellular cytotoxicity.

Embodiment 9: A molecule capable of inhibiting signaling between SDF-1 and CXCR4 and/or CXCR7, wherein the molecule is for use in a method of inducing leukocyte mediated immunue response against a tumor and/or metastases, wherein preferably leukocyte-mediated immune response comprises direct leukocyte-mediated cytotoxicity and leukocyte-mediated antibody-dependent cellular cytotoxicity.

Embodiment 10: A molecule capable of inhibiting signaling between SDF-1 and CXCR4 and/or CXCR7, wherein the molecule is for use in a method for treatment of a disease, wherein the method comprises inducing leukocyte mediated immunue response against a tumor and/or metastases, wherein preferably leukocyte-mediated immune response comprises direct leukocyte-mediated cytotoxicity and leukocyte-mediated antibody-dependent cellular cytotoxicity.

Embodiment 11: The molecule for use according to any one of embodiments 9 to 10, wherein the method comprises modulating the number and/or the spatial distribution of tumor-infiltrating leukocytes in and/or around the tumor and/or the metastases.

Embodiment 12: The molecule for use according to any one of embodiment 9 to 11, wherein the method comprises establishing an SDF-1 gradient a) in and/or around the tumor;

b) in and/or around the metastases;

c) around the vasculature of the tumor; and/or d) around the vasculature of the metastases.

Embodiment 13: The molecule for use according to any one of embodiments 1 to 12, wherein the method comprises administering to a patient a therapeutically effective amount of the molecule.

Embodiment 14: The molecule for use according to any one of embodiments 1 to 13, wherein the leukocytes are lymphocytes, wherein preferably the lymphocytes are selected from the group comprising NK cells, T cells and B cells.

Embodiment 15: The molecule for use according to any one of embodiments 1 to 14, wherein the molecule a) increases the number of NK cells in a tumor and/or metastases, and/or b) leads to a more homogeneous spatial distribution of NK cells in a tumor and/or metastases as compared to not using the method according to any of embodiments 1 to 14, and/or c) leads to a spatial distribution of NK cells to more compartments in a tumor and/or metastases as compared to not using the method according to any of embodiments 1 to 14, wherein preferably the NK cell mediated immunue response against a tumor and/or metastases is enhanced, and/or the NK cell mediated antibody-dependent cellular cytotoxicity is enhanced, more preferably the NK cell mediated immunue response against a tumor and/or metastases is enhanced, and/or the NK cell mediated antibody-dependent cellular cytotoxicity is enhanced which is achieved because of the effect of a), b) and/or c).

Embodiment 16: The molecule for use according to any one of embodiments 1 to 14, wherein the molecule increases the number of T cells in a tumor and/or metastases, wherein preferably the T cells are CD3+ T cells.

Embodiment 17: The molecule for use according to embodiment 16, wherein the T cells are cytotoxic T cells, wherein preferably the cytotoxic T cells are CD3+CD8+ cytotoxic T cells.

Embodiment 18: The molecule according to embodiment 16, wherein the T cells are T helper cells, wherein preferably the T helper cells are CD3+CD4+ T helper cells.

Embodiment 19: The molecule for use according to any one of embodiments 16 to 18, wherein the molecule increases the number of regulatory T cells in a tumor and/or metastases to a lesser extent than the cytotoxic T cells and/or T helper cells, wherein preferably the regulatory T cells are CD3+CD4+CD25+CD127-regulatory T cells.

Embodiment 20: The molecule for use according to any one of embodiments 1 to 14, wherein the molecule increases the number of B cells in in a tumor and/or metastases, wherein preferably the B cells are CD19+ B cells.

Embodiment 21: The molecule for use according to any one of embodiments 1 to 20, wherein the molecule does not increase the number of monocytes and/or macrophages in the tumor and/or metastases, wherein preferably the monocytes are CD14+monocytes and the macrophages are CD14+macrophages.

Embodiment 22: A molecule capable of inhibiting signaling between SDF-1 and CXCR4 and/or CXCR7, wherein the molecule is for use in a method for promoting lymphocyte activity in a tumor and/or metastases, wherein preferably the lymphocytes are selected from the group comprising NK cells, T cells and B cells.

Embodiment 23: A molecule capable of inhibiting signaling between SDF-1 and CXCR4 and/or CXCR7, wherein the molecule is for use in a method for the treatment of a disease, wherein the method comprises promoting lymphocyte activity in a tumor and/or metastases, wherein preferably the lymphocytes are selected from the group comprising NK cells, T cells and B cells.

Embodiment 24: The molecule for use according to any one of embodiments 22 to 23, wherein the method comprises modulating the number and/or spatial distributing of lymphocytes, preferably tumor-infiltrating lymphocytes, in and/or around the tumor and/or the metastases.

Embodiment 25: The molecule for use according to any one of embodiments 22 to 24, wherein the method comprises establishing an SDF-1 gradient a) in and/or around the tumor;

b) in and/or around the metastases;

c) around the vasculature of the tumor; and/or d) around the vasculature of the metastases.

Embodiment 26: The molecule for use according to any one of embodiments 22 to 25, wherein the method comprises administering to a patient a therapeutically effective amount of the molecule.

Embodiment 27: The molecule for use according to any one of embodiment 22 to 26, wherein the molecule brings NK cells in contact with the cancer cells of a tumor and/or metastases.

Embodiment 28: The molecule for use according to any one of embodiment 22 to 26, wherein the molecule brings the T cells in contact with the cancer cells of a tumor and/or metastases, wherein preferably the T cells are CD3+ T cells.

Embodiment 29: The molecule for use according to embodiment 28, wherein the molecule brings the T cells in contact with the cancer cells of the tumor and/or metastases by increasing the number of T cells in the tumor and/or metastases.

Embodiment 30: The molecule for use according to any one of embodiments 28 to 29, wherein the T cells are cytotoxic T cells, wherein preferably the cytotoxic T cells are CD3+CD8+ cytotoxic T cells.

Embodiment 31: The molecule for use according to any one of embodiments 28 to 29, wherein the T cells are T helper cells, wherein preferably the T helper cells are CD3+CD4+ T helper cells.

Embodiment 32: The molecule for use according to any one of embodiments 28 to 31, wherein the molecule increases the number of regulatory T cells in a tumor and/or metastases to a lesser extent than the cytotoxic T cells and/or T helper cells, wherein preferably the regulatory T cells are CD3+CD4+CD25+CD127− regulatory T cells.

Embodiment 33: The molecule for use according to embodiment 27, wherein the molecule brings the NK cells in contact with the cancer cells of the tumor and/or metastases by a) increasing the number of the NK cells in the tumor and/or metastases, and/or b) inducing a more homogeneous spatial distribution of NK cells in a tumor and/or metastases as compared to not using the method according to any of embodiments 22 to 33, and/or c) inducing a spatial distribution of NK cells to more compartments in a tumor and/or metastases as compared to not using the method according to any of embodiments 22 to 33, wherein preferably thereby the NK cell mediated immunue response against a tumor and/or metastases is enhanced, and/or the NK cell mediated antibody-dependent cellular cytotoxicity is enhanced.

Embodiment 34: The molecule for use according to any one of embodiments 22 to 26, wherein the molecule brings the B cells in contact with the cancer cells of the tumor and/or metastases, wherein preferably the B cells are CD19+ B cells.

Embodiment 35: The molecule for use according to embodiment 34, wherein the molecule brings the B cells in contact with the cancer cells of the tumor and/or metastases by increasing the number of B cells in the tumor and/or metastases.

Embodiment 36: The molecule for use according to any one of embodiments 22 to 35, wherein the molecule does not increase the number of monocytes and/or macrophages in a tumor and/or metastases, wherein preferably the monocytes are CD14+ monocytes and the macrophages are CD14+ macrophages.

Embodiment 37: The molecule for use according to any one of embodiments 1 to 36, wherein the molecule is an antagonist of a) SDF-1;

b) CXCR4;

c) CXCR7; or d) CXCR4 and CXCR7.

Embodiment 38: The molecule for use according to any one of embodiments 1 to 37, wherein the molecule is an antagonist of SDF-1 that is capable of extravasation in a tumor and/or metastases.

Embodiment 39: The molecule for use according to any one of embodiments 1 to 38, wherein the SDF-1 gradient is an SDF-1 microgradient, preferably an SDF-1 microgradient around the vasculature into the tumor and/or metastases, wherein more preferably the SDF-1 microgradient leads to migration of lymphocytes into the and, respectively, in a tumor and/or metastases.

Embodiment 40: The molecule for use according to any one of embodiments 1 to 39, wherein the method comprises administering to a and/or the subject to be treated at least one checkpoint inhibitor, an antibody being capable of binding to a tumor cell and/or metastases and being capable of inducing antibody-dependent cellular cytotoxicity (ADCC) and/or a T cell- or NK cell engager.

Embodiment 41: The molecule for use according to any one of embodiments 1 to 40, wherein the tumor and/or metastases are individually and independently selected from the group comprising solid tumors, lymphoma, myeloma and precursor thereof.

Embodiment 42: The molecule for use according to embodiment 41, wherein the myeloma is multiple myeloma.

Embodiment 43: The molecule for use according to embodiment 41, wherein the solid tumors are selected from the group comprising glioblastoma, colorectal cancer, breast cancer, lymphoma, prostate cancer, pancreatic cancer, renal cancer, ovarian cancer and lung cancer.

Embodiment 44: The molecule for use according to any one of embodiments 1 to 43, wherein the molecule is a nucleic acid molecule that is capable of binding to SDF-1 and an SDF-1 receptor, preferably the SDF-1 receptor is CXCR4 or CXCR7.

Embodiment 45: The nucleic acid molecule for use according to embodiment 44, wherein the nucleic acid molecule is selected from the group comprising an SDF-1 binding nucleic acid molecule of type B, an SDF-1 binding nucleic acid molecule of type C, an SDF-1 binding nucleic acid molecule of type A and an SDF-1 binding nucleic acid molecule of type D.

Embodiment 46: The nucleic acid molecule for use according to embodiment 45, wherein the SDF-1 binding nucleic acid molecule of type B comprises a central stretch of nucleotides, whereby the central stretch of nucleotides comprises the following nucleotide sequence:

(SEQ ID NO: 52)
5' GUGUGAUCUAGAUGUADWGGCUGWUCCUAGUYAGG 3'.

Embodiment 47: The nucleic acid molecule for use according to embodiment 46, wherein the central stretch of nucleotides comprises the following nucleotide sequence:

(SEQ ID NO: 53)
5' GUGUGAUCUAGAUGUADUGGCUGAUCCUAGUCAGG 3'.

Embodiment 48: The nucleic acid molecule for use according to any one of embodiments 46 to 47, wherein the SDF-1 binding nucleic acid molecule of type B comprises in 5'→3' direction a first terminal stretch of nucleotides, the central stretch of nucleotides, and a second terminal stretch of nucleotides.

Embodiment 49: The nucleic acid molecule for use according to any one of embodiments 46 to 47, wherein the SDF-1 binding nucleic acid molecule of type B comprises in 5'→3' direction a second terminal stretch of nucleotides, the central stretch of nucleotides, and a first terminal stretch of nucleotides.

Embodiment 50: The nucleic acid molecule for use according to any one of embodiments 48 to 49, wherein the first terminal stretch of nucleotides comprises a nucleotide sequence of 5' X1X2SVNS 3' and the second terminal stretch of nucleotides comprises a nucleotide sequence of 5' BVBSX3X4 3', whereby X1 is either absent or is A, X2 is G, X3 is C and X4 is either absent or is U;

or

X1 is absent, X2 is either absent or is G, X3 is either absent or is C and X4 is absent.

Embodiment 51: The nucleic acid molecule for use according to any one of embodiments 48 to 50, preferably embodiment 50, wherein the first terminal stretch of nucleotides comprises a nucleotide sequence of 5' X1X2CRWG 3' and the second terminal stretch of nucleotides comprises a nucleotide sequence of 5' KRYSX3X4 3', whereby X1 is either absent or A, X2 is G, X3 is C and X4 is either absent or U.

Embodiment 52: The nucleic acid molecule for use according to any one of embodiments 48 to 51, preferably embodiment 50 or 51, wherein the first terminal stretch of nucleotides comprises a nucleotide sequence of 5' X1X2CGUG 3' and the second terminal stretch of nucleotides comprises a nucleotide sequence of 5' UACGX3X4 3', whereby X1 is either absent or A, X2 is G, X3 is C, and X4 is either absent or U, preferably the first terminal stretch of nucleotides comprises a nucleotide sequence of 5' AGCGUG 3' and the second terminal stretch of nucleotides comprises a nucleotide sequence of 5' UACGCU 3'.

Embodiment 53: The nucleic acid molecule for use according to any one of embodiments 48 to 50, preferably embodiment 50, wherein the first terminal stretch of nucleotides comprises a nucleotide sequence of 5' X1X2SSBS 3' and the second terminal stretch of nucleotides comprises a nucleotide sequence of 5' BVSSX3X4 3', whereby X1 is absent, X2 is either absent or G, X3 is either absent or C, and X4 is absent, preferably the first terminal stretch of nucleotides comprises a nucleotide sequence of 5' GCGUG 3' and the second terminal stretch of nucleotides comprises a nucleotide sequence of 5' UACGC 3'.

Embodiment 54: The nucleic acid molecule for use according to any one of embodiments 45 to 53, wherein the SDF-1 binding nucleic acid molecule of type B comprises a nucleotide sequence according to any one of SEQ ID NO: 5 to SEQ ID NO: 20 and SEQ ID NO: 22 to SEQ ID NO: 28, preferably any one of SEQ ID NO: 5 to SEQ ID NO: 7, SEQ ID NO: 16, SEQ ID NO: 22 and SEQ ID NO: 28, more preferably any one of SEQ ID NO: 22 and SEQ ID NO: 28.

Embodiment 55: The nucleic acid molecule for use according to embodiment 45, wherein the SDF-1 binding nucleic acid molecule of type C comprises a central stretch of nucleotides, whereby the central stretch of nucleotides comprises a nucleotide sequence of GGUYAGGGCUHRXAAGUCGG (SEQ ID NO: 108), whereby XA is either absent or is A.

Embodiment 56: The nucleic acid molecule for use according to embodiment 55, wherein the central stretch of nucleotides comprises a nucleotide sequence of 5' GGUYAGGGCUHRAAGUCGG 3' (SEQ ID NO: 109), 5' GGUYAGGGCUHRAGUCGG 3' (SEQ ID NO: 110) or 5' GGUUAGGGCUHGAAGUCGG 3' (SEQ ID NO: 111), preferably 5' GGUUAGGGCUHGAAGUCGG 3' (SEQ ID NO: 111).

Embodiment 57: The nucleic acid molecule for use according to any one of embodiments 55 to 56, wherein the SDF-1 binding nucleic acid molecule of type C comprises in 5'→3' direction a first terminal stretch of nucleotides, the central stretch of nucleotides, and a second terminal stretch of nucleotides.

Embodiment 58: The nucleic acid molecule for use according to any one of embodiments 55 to 56, wherein the SDF-1 binding nucleic acid molecule of type C comprises in 5'→3' direction a second terminal stretch of nucleotides, the central stretch of nucleotides, and a first terminal stretch of nucleotides.

Embodiment 59: The nucleic acid molecule for use according to any one of embodiments 57 to 58, wherein the first terminal stretch of nucleotides comprises a nucleotide sequence of 5' RKSBUSNVGR 3' (SEQ ID NO: 138) and the second stretch of nucleotides comprises a nucleotide sequence of 5' YYNRCASSMY 3' (SEQ ID NO: 139), preferably the first terminal stretch of nucleotides comprises a nucleotide sequence of 5' RKSBUGSVGR 3 '(SEQ ID NO: 140) and the second terminal stretch of nucleotides comprises a nucleotide sequence of 5' YCNRCASSMY 3' (SEQ ID NO: 141).

Embodiment 60: The nucleic acid molecule for use according to any one of embodiments 57 to 58, wherein the first terminal stretch of nucleotides comprises a nucleotide sequence of 5' XSSSSV 3' and the second terminal stretch of nucleotides comprises a nucleotide sequence of 5' BSSSXS 3', whereby Xs is either absent or is S, preferably the first terminal stretch of nucleotides comprises a nucleotide sequence of 5' SGGSR 3' and the second terminal stretch of nucleotides comprises a nucleotide sequence of 5' YSCCS 3'.

Embodiment 61: The nucleic acid molecule for use according to any one of embodiments 57 to 58, wherein a) the first terminal stretch of nucleotides comprises a nucleotide sequence of 5' GCCGG 3' and the second terminal stretch of nucleotides comprises a nucleotide sequence of 5' CCGGC 3'; or b) the first terminal stretch of nucleotides comprises a nucleotide sequence of 5' CGUGCGCUUGAGAUAGG 3 '(SEQ ID NO: 220) and the second terminal stretch of nucleotides comprises a nucleotide sequence of 5' CUGAUUCUCACG 3' (SEQ ID NO: 221); or c) the first terminal stretch of nucleotides comprises a nucleotide sequence of 5' UGAGAUAGG 3' and the second terminal stretch of nucleotides comprises a nucleotide sequence of 5' CUGAUUCUCA 3' (SEQ ID NO: 222); or d) the first terminal stretch of nucleotides comprises a nucleotide sequence of 5' GAGAUAGG 3' and the second terminal stretch of nucleotides comprises a nucleotide sequence of 5' CUGAUUCUC 3'.

Embodiment 62: The nucleic acid molecule for use according to any of embodiments 55 to 61, wherein the type C SDF-1 binding nucleic acid molecule comprises a nucleotide sequence according to any one of SEQ ID NO: 95 to SEQ ID NO: 107, SEQ ID NO: 112 to SEQ ID NO: 137, SEQ ID NO: 223 and SEQ ID NO: 224, preferably any one of SEQ ID NO: 120, SEQ ID NO: 128, SEQ ID NO: 129, SEQ ID NO:134, SEQ ID NO: 135, SEQ ID NO: 223 and SEQ ID NO: 224.

Embodiment 63: The nucleic acid molecule for use according to embodiment 45, wherein the SDF-1 binding nucleic acid molecule of type A comprises a central stretch of nucleotides, whereby the central stretch of nucleotides comprises a nucleotide sequence of 5' AAAGYRACAHGUMAAXAUGAAAGGUARC 3' (SEQ ID NO: 74), whereby XA is either absent or is A.

Embodiment 64: The nucleic acid molecule for use according to embodiment 63, wherein the central stretch of nucleotides comprises a nucleotide sequence of 5'AAAGYRACAHGUMAAUGAAAGGUARC 3' (SEQ ID NO: 75), or 5' AAAGYRACAHGUMAAAUGAAAGGUARC 3' (SEQ ID NO: 76), or 5' AAAGYAACAHGUCAAUGAAAGGUARC 3' (SEQ ID NO: 77), preferably the central stretch of nucleotides comprises a nucleotide sequence of 5' AAAGYAACAHGUCAAUGAAAGGUARC 3' (SEQ ID NO: 77).

Embodiment 65: The nucleic acid molecule for use according to any one of embodiments 63 to 64, wherein the SDF-1 binding nucleic acid molecule of type A comprises in 5'→3' direction a first terminal stretch of nucleotides, the central stretch of nucleotides, and a second terminal stretch of nucleotides.

Embodiment 66: The nucleic acid molecule for use according to any one of embodiments 63 to 64, wherein the SDF-1 binding nucleic acid molecule of type A comprises in 5'→3' direction a second terminal stretch of nucleotides, the central stretch of nucleotides, and a first terminal stretch of nucleotides.

Embodiment 67: The nucleic acid molecule for use according to any one of embodiments 65 to 66, wherein the first terminal stretch of nucleotides comprises a nucleotide sequence of 5' X1X2NNBV 3' and the second terminal stretch of nucleotides comprises a nucleotide sequence of 5' BNBNX3X4 3' whereby X1 is either absent or R, X2 is S, X3 is S and X4 is either absent or Y;

or

X1 is absent, X2 is either absent or S, X3 is either absent or S and X4 is absent.

Embodiment 68: The nucleic acid molecule for use according to any one of embodiments 65 to 67, preferably 67, wherein the first terminal stretch of nucleotides comprises a nucleotide sequence of 5' RSHRYR 3' and the second terminal stretch of nucleotides comprises a nucleotide sequence of 5' YRYDSY 3', preferably the first terminal stretch of nucleotides comprises a nucleotide sequence of 5' GCUGUG 3' and the second terminal stretch of nucleotides comprises a nucleotide sequence of 5' CGCAGC 3'.

Embodiment 69: The nucleic acid molecule for use according to any one of embodiments 65 to 67, preferably '67, wherein the first terminal stretch of nucleotides comprises a nucleotide sequence of 5' X2BBBS 3' and the second terminal stretch of nucleotides comprises a nucleotide sequence of 5' SBBVX3 3', whereby X2 is either absent or is S and X3 is either absent or is S;

preferably the first terminal stretch of nucleotides comprises a nucleotide sequence of 5' CUGUG 3' and the second terminal stretch of nucleotides comprises a nucleotide sequence of 5' CGCAG 3';

or the first terminal stretch of nucleotides comprises a nucleotide sequence of 5' GCGUG 3' and the second terminal stretch of nucleotides comprises a nucleotide sequence of 5' CGCGC 3'.

Embodiment 70: The nucleic acid molecule for use according to any one of embodiments 63 to 69, wherein the SDF-1 binding nucleic acid molecule of type A comprises a nucleotide sequence according to any one of SEQ ID NO: 60 to SEQ ID NO: 73, SEQ ID NO: 78 to SEQ ID NO: 82, SEQ ID NO: 84 to SEQ ID NO: 87, SEQ ID NO: 89 to SEQ ID NO: 94, and SEQ ID NO: 145, preferably any one of SEQ ID NO: 60, SEQ ID NO: 63, SEQ ID NO: 66, SEQ ID NO: 78, SEQ ID NO: 84, and SEQ ID NO: 146, more preferably any one of SEQ ID NO: 84 and SEQ ID NO: 146.

Embodiment 71: The nucleic acid molecule for use according to embodiment 45, wherein the SDF-1 binding nucleic acid molecule of type D comprises a nucleotide sequence according to any one of SEQ ID NO: 142 to SEQ ID NO: 144.

Embodiment 72: The nucleic acid molecule for use according to any one of embodiments 1 to 71, wherein the SDF-1 is human SDF-1, whereby preferably the human SDF-1 is human SDF-1 alpha or human SDF-1 beta, more preferably the human SDF-1 is human SDF-1 alpha.

Embodiment 73: The nucleic acid molecule for use according to any one of embodiments 1 to 72, wherein the nucleic acid molecule comprises a modification, whereby the modification is preferably a high molecular weight moiety and/or whereby the modification preferably allows to modify the characteristics of the nucleic acid molecule in terms of residence time in the animal or human body, preferably the human body.

Embodiment 74: The nucleic acid molecule for use according to embodiment 73, wherein the modification is selected from the group comprising a HES moiety, a PEG moiety, biodegradable modifications and combinations thereof.

Embodiment 75: The nucleic acid molecule for use according to embodiment 74, wherein the modification is a PEG moiety consisting of a straight PEG or branched PEG, whereby preferably the molecular weight of the straight or branched PEG is from about 20,000 to 120,000 Da, more preferably from about 30,000 to 80,000 Da and most preferably about 40,000 Da.

Embodiment 76: The nucleic acid molecule for use according to embodiment 74, wherein the modification is a HES moiety, whereby preferably the molecular weight of the HES moiety is from about 10,000 to 200,000 Da, more preferably from about 30,000 to 170.000 Da and most preferably about 150,000 Da.

Embodiment 77: The nucleic acid molecule for use according to any one of embodiments of 73 to 76, wherein the modification is attached to the nucleic acid molecule via a linker, wherein preferably the linker is a biostable or biodegradable linker.

Embodiment 78: The nucleic acid molecule for use according to any one of embodiments of 73 to 77, wherein the modification is attached to the nucleic acid molecule at the 5'-terminal nucleotide of the nucleic acid molecule and/or the 3'-terminal nucleotide of the nucleic acid molecule and/or to a nucleotide of the nucleic acid molecule between the 5'-terminal nucleotide of the nucleic acid molecule and the 3'-terminal nucleotide of the nucleic acid molecule Embodiment 79: The nucleic acid molecule for use according to any one of embodiments 44 to 78, wherein the nucleotides of the nucleic acid molecule or the nucleotides forming the nucleic acid molecule are L-nucleotides.

Embodiment 80: The nucleic acid molecule for use according to any one of embodiments 44 to 80, whereby the nucleic acid molecule is an L-nucleic acid molecule.

Embodiment 81: A pharmaceutical composition comprising as a first pharmaceutically active agent a molecule according to any one of embodiments 1 to 80 and at least a further constituent and at least one further pharmaceutically active agent, whereby the further constituent is selected from the group comprising a pharmaceutically acceptable excipient and a pharmaceutically acceptable carrier, and whereby, preferably, the pharmaceutical composition is for use in a method for the treatment and/or prevention of a tumor and/or metastases, and, preferably, the at least one further pharmaceutically active agent is a check-point inhibitor, an antibody being capable of binding to a tumor cell and/or metastases and being capable of inducing antibody-dependent cellular cytotoxicity (ADCC) and/or a T cell engager or NK cell engager.

Embodiment 82: The pharmaceutical composition for use according to embodiment 81, wherein the method for the treatment of a tumor and/or metastases comprises administering a or the further pharmaceutically active agent and/or irradiating the subject suffering from the tumor and/or metastases and/or surgery and/or cellular therapy and/or immunotherapy.

Embodiment 83: The pharmaceutical composition according to any one of embodiments 81 to 82, wherein the at lease one further pharmaceutically active agent is a pharmaceutically active agent selected from the group comprising an antibody, an alkylating agent, an anti-metabolite, a plant alkaloid, preferably vincristine, a plant terpenoid, a topoisomerase inhibitor, Leucovorin, Methotrexate, Tamoxifen, Sorafenib, Lenalidomide, Bortezomib, Dexamethasone, Flurouracil, Prednisone, a chemotherapeutic agent, a cancer vaccine, a checkpoint inhibitor, an antibody being capable of binding to a tumor cell and/or metastases and being capable of inducing antibody-dependent cellular cytotoxicity (ADCC), and a T cell- or NK cell engager.

Embodiment 84: The pharmaceutical composition according to any one of embodiments 81 to 83, wherein the tumor and/or metastases are each individually and independently selected from the group comprising a solid tumor, lymphoma, myeloma and a precursor thereof.

Embodiment 85: The pharmaceutical composition according to embodiment 84, wherein the myeloma is multiple myeloma.

Embodiment 86: The pharmaceutical composition according to embodiment 84, wherein the solid tumor is selected from the group comprising glioblastoma, colorectal cancer, breast cancer, lymphoma, prostate cancer, pancreatic cancer, renal cancer, ovarian cancer and lung cancer.

Embodiment 87: A medicament comprising one or several dosage units of at least a first pharmaceutically active agent, wherein the first pharmaceutically active agent is a molecule as defined in any one of embodiments 1 to 80, whereby the medicament is for use in a method for the treatment and/or prevention of a tumor and/or metastases.

Embodiment 88: The medicament for use according to embodiment 87, wherein the method for the treatment of a tumor and/or metastases comprises administering a further pharmaceutically active agent and/or irradiating the subject suffering from the tumor and/or metastases and/or surgery and/or cellular therapy and/or immunotherapy.

Embodiment 89: The medicament according to any one of embodiments 87 to 88, wherein the medicament comprises a further pharmaceutically active agent, preferably one or several dosage units of a further pharmaceutically active agent, whereby the further pharmaceutically active agent is selected from the group comprising an antibody, an alkylating agent, an anti-metabolite, a plant alkaloid, preferably vincristine, a plant terpenoid, a topoisomerase inhibitor, Leucovorin, Methotrexate, Tamoxifen, Sorafenib, Lenalidomide, Bortezomib, Dexamethasone, Flurouracil, a chemotherapeutic agent, a cancer vaccine, a checkpoint inhibitor, an antibody being capable of binding to a tumor cell and/or metastases and being capable of inducing antibody-dependent cellular cytotoxicity (ADCC), and a T cell- or NK cell engager.

Embodiment 90: The medicament according to any one of embodiments 87 to 89, wherein the tumor and/or metastases are each individually and independently selected from the group comprising a solid tumor, lymphoma, myeloma and a precursor thereof.

Embodiment 91: The medicament according to embodiment 90, wherein the myeloma is multiple myeloma.

Embodiment 92: The medicament according to embodiment 90, wherein the solid tumor is selected from the group comprising glioblastoma, colorectal cancer, breast cancer, lymphoma, prostate cancer, pancreatic cancer, renal cancer, ovarian cancer and lung cancer.

Embodiment 93: Use of a nucleic acid molecule as defined in any one of embodiments 1 to 80, for the manufacture of a medicament for the treatment of a tumor and/or metastases.

Embodiment 94: Use according to embodiment 93, wherein the treatment of a tumor and/or metastases comprises administering a further pharmaceutically active agent and/or irradiating the subject to be treated and/or surgery and/or cellular therapy and/or immunotherapy.

Embodiment 95: Use according to any one of embodiments 93 to 94, wherein the medicament is used in or is to be used in combination with a further pharmaceutically active agent, whereby the further pharmaceutically active agent is a pharmaceutically active agent selected from the group comprising an antibody, an alkylating agent, an anti-metabolite, a plant alkaloid, preferably vincristine, a plant terpenoid, a topoisomerase inhibitor, Leucovorin, Methotrexate, Tamoxifen, Sorafenib, Lenalidomide, Bortezomib, Dexamethasone, Flurouracil, Prednisone, a chemotherapeutic agent, a cancer vaccine, a checkpoint inhibitor, an antibody being capable of binding to a tumor cell and/or metastases and being capable of inducing antibody-dependent cellular cytotoxicity (ADCC), and a T cell- or NK cell engager.

Embodiment 96: Use according to embodiment 94, wherein the further pharmaceutically active agent is a pharmaceutically active agent selected from the group comprising an antibody, an alkylating agent, an anti-metabolite, a plant alkaloid, preferably vincristine, a plant terpenoid, a topoisomerase inhibitor, Leucovorin, Methotrexate, Tamoxifen, Sorafenib, Lenalidomide, Bortezomib, Dexamethasone, Flurouracil, Prednisone, a chemotherapeutic agent, a cancer vaccine, a checkpoint inhibitor, an antibody being capable of binding to a tumor cell and/or metastases and being capable of inducing antibody-dependent cellular cytotoxicity (ADCC), and a T cell- or NK cell engager.

Embodiment 97: Use according to any one of embodiments 93 to 96, wherein the tumor and/or metastases are selected from the group comprising a solid tumor, lymphoma, myeloma and a precursor thereof.

Embodiment 98: Use according to embodiment 97, wherein the myeloma is multiple myeloma.

Embodiment 99: Use according to embodiment 97, wherein the solid tumor is selected from the group comprising glioblastoma, colorectal cancer, breast cancer, lymphoma, prostate cancer, pancreatic cancer, renal cancer, ovarian cancer and lung cancer.

Embodiment 100: A method for the treatment of a subject suffering from a tumor and/or metastases, wherein the method comprises a step a) of administering to the subject a pharmaceutically effective amount of a molecule capable of binding to SDF-1 as defined in any one of embodiments 1 to 80.

Embodiment 101: The method according to embodiment 100, whereby the method comprises a step b) of irradiating the subject and/or subjecting the subject to surgery and/or cellular therapy and/or administering a pharmaceutically effective amount of a further pharmaceutically active agent to the subject, wherein the further pharmaceutically active agent is a pharmaceutically active agent selected from the group comprising an antibody, an alkylating agent, an anti-metabolite, a plant alkaloid, preferably vincristine, a plant terpenoid, a topoisomerase inhibitor, Leucovorin, Methotrexate, Tamoxifen, Sorafenib, Lenalidomide, Bortezomib, Dexamethasone, Flurouracil, Prednisone, a chemotherapeutic agent, a cancer vaccine, a checkpoint inhibitor, an antibody being capable of binding to a tumor cell and/or metastases and being capable of inducing antibody-dependent cellular cytotoxicity (ADCC), and a T cell- or NK cell engager.

Embodiment 102: A method of modulating the number and the spatial distribution of tumor-infiltrating leukocytes in a tumor and/or metastases, wherein the method comprises administering to a subject bearing the tumor and/or metastases a pharmaceutically effective amount of the molecule according to embodiments 1 to 80.

Embodiment 103: A method for promoting lymphocyte activity in a tumor and/or metastases, wherein the method comprises administering to a subject bearing the tumor and/or metastases a therapeutically effective amount of the molecule according to embodiments 1 to 80, wherein preferably the lymphocytes are selected from the group comprising NK cells, T cells and B cells.

Embodiment 104: The method according to any one of embodiments 100 to 103, wherein the tumor and/or metastases are selected from the group comprising a solid tumor, lymphoma, myeloma and a precursor thereof.

Embodiment 105: The method according to embodiment 104, wherein the myeloma is multiple myeloma.

Embodiment 106: The method according to embodiment 104, wherein the solid tumor is selected from the group comprising glioblastoma, colorectal cancer, breast cancer, lymphoma, prostate cancer, pancreatic cancer, renal cancer, ovarian cancer and lung cancer.

Embodiment 107: The molecule for use according to embodiment 40, wherein a) the checkpoint inhibitor is a PD-1 signaling inhibitor, a CTLA-4 antagonist, a TIM-3 antagonist, or, a LAG3 antagonist, wherein preferably the PD-1 signaling inhibitor is a PD-1 inhibitor or a PDL-1 inhibitor, wherein more preferably the PD-1 inhibitor is an anti-PD-1 antibody and the PDL-1 inhibitor is an anti-PDL-1 antibody, and b) the antibody being capable of binding to a tumor cell and/or metastases and being capable of inducing antibody-dependent cellular cytotoxicity (ADCC) is selected from the group comprising antibodies binding to α-CD52, α-EGFR, α-CD38, SLAMF7 (CS1/CD319/CRACC), CD20, HER2 (ERBB2/neu), and HER2, preferably selected from the group comprising rituximab, alemtuzumab, cetuximab, daratumumab, elotuzumab, ofatumumab, pertuzumab and trastuzumab.

Embodiment 108: The pharmaceutical composition according to embodiment 81, wherein a) the checkpoint inhibitor is a PD-1 signaling inhibitor, a CTLA-4 antagonist, a TIM-3 antagonist, or a LAG3 antagonist, wherein preferably the PD-1 signaling inhibitor is a PD-1 inhibitor or a PDL-1 inhibitor, wherein more preferably the PD-1 inhibitor is an anti-PD-1 antibody and the PDL-1 inhibitor is an anti-PDL-1 antibody, and b) the antibody being capable of binding to a tumor cell and/or metastases and being capable of inducing antibody-dependent cellular cytotoxicity (ADCC) is selected from the group comprising antibodies binding to α-CD52, α-EGFR, α-CD38, SLAMF7 (CS1/CD319/CRACC), CD20, HER2 (ERBB2/neu), and HER2, preferably selected from the group comprising rituximab, alemtuzumab, cetuximab, daratumumab, elotuzumab, ofatumumab, pertuzumab and trastuzumab.

Embodiment 109: The medicament for use according to embodiment 87, whereby a) the checkpoint inhibitor is a PD-1 signaling inhibitor, a CTLA-4 antagonist, a TIM-3 antagonist, or a LAG3 antagonist, wherein preferably the PD-1 signaling inhibitor is a PD-1 inhibitor or a PDL-1 inhibitor, wherein more preferably the PD-1 inhibitor is an anti-PD-1 antibody and the PDL-1 inhibitor is an anti-PDL-1 antibody, and b) the antibody being capable of binding to a tumor cell and/or metastases and being capable of inducing antibody-dependent cellular cytotoxicity (ADCC) is selected from the group comprising antibodies binding to α-CD52, α-EGFR, α-CD38, SLAMF7 (CS1/CD319/CRACC), CD20, HER2 (ERBB2/neu), and HER2, preferably selected from the group comprising rituximab, alemtuzumab, cetuximab, daratumumab, elotuzumab, ofatumumab, pertuzumab and trastuzumab.

Embodiment 110: Use according to any one of embodiments 95 and 96, wherein a) the checkpoint inhibitor is a PD-1 signaling inhibitor, a CTLA-4 antagonist, a TIM-3 antagonist, or a LAG3 antagonist, wherein preferably the PD-1 signaling inhibitor is a PD-1 inhibitor or a PDL-1 inhibitor, wherein more preferably the PD-1 inhibitor is an anti-PD-1 antibody and the PDL-1 inhibitor is an anti-PDL-1 antibody, and b) the antibody being capable of binding to a tumor cell and/or metastases and being capable of inducing antibody-dependent cellular cytotoxicity (ADCC) is selected from the group comprising antibodies binding to α-CD52, α-EGFR, α-CD38, SLAMF7 (CS1/CD319/CRACC), CD20, HER2 (ERBB2/neu), and HER2, preferably selected from the group comprising rituximab, alemtuzumab, cetuximab, daratumumab, elotuzumab, ofatumumab, pertuzumab and trastuzumab.

Embodiment 111: The molecule for use according to any one of embodiments 1 to 80, wherein the molecule redistributes lymphocytes from bone marrow and/or lymphoid tissues into a tumor and/or metastases, wherein preferably lymphocytes are selected from the group comprising T cells, NK cells and B cells.

Physiologically, CXCL12 is mainly expressed by mesenchymal stromal cells in various organs, such as the liver, lungs and bone marrow (BM) (Guo, Wang et al. 2015). Many tumors have also been found to overexpress CXCL12, probably driven by the hypoxic state and the fact that CXCL12 is a hypoxia-inducible factor 1α (HIF-1α) target gene, i.e. HIF-1α overexpression leads to more CXCL12. Using a 3-dimensional in vitro model of a tumor and its microenvironment (tumor/stroma spheroids), the inventors have found that CXCL12 expression induces a limited infiltration of the "tumor" by human NK cells, T cells and B cells. When adding an inhibitor of CXCL12 (such as the Spiegelmer NOX-A12) to the microtissue during the incubation phase with NK cells, T cells or peripheral blood mononuclear cells (PBMC) the inventors have surprisingly found a dose-dependent increase in lymphocyte infiltration with an optimal NOX-A12 concentration around 10 nM. In greater detail the infiltration of T cells in general, and more specifically of cytotoxic T cells and T helper cells was enhanced; regulatory T cell (Treg) infiltration was enhanced to a lesser extent thereby shifting the balance more to the pro-inflammatory type of an immune reaction; NK cell infiltration and B cell infiltration was enhanced, whereas monocyte/macrophage infiltration remained low and unaffected. Thus, SDF-1 inhibition in general and NOX-A12 treatment in particular is expected to modulate the cancer infiltration of these cells in vivo.

The inventors developed the above mentioned 3-dimensional tumor stroma microtissue by seeding a mixture of a human cancer cells with stroma cells (here CXCL12-expressing murine bone marrow stromal cells, MS5). Tumor/stroma spheroids formed spontaneously during the cultivation period of three days in ultra-low attachment plates. PBMC from human donors, T cells or NK cells that had both been purified from PBMC were added overnight in the presence of various concentrations in the range of 0-100 nM of the CXCL12 inhibitor NOX-A12.

Tumor cells used were representative at least for a variety of solid tumors:

PSN-1 pancreatic ductal adenocarcinoma,
HT-29 colorectal cancer,
H1299 Non-small cell lung cancer, and
U251MG glioblastoma.

T cell infiltration into the spheroids was then either assessed by immunohistochemistry (staining of $CD3^+$ cells) from central spheroid sections and quantified by counting, or it was measured by flow cytometry analysis after dissociation of the spheroids with Accumax and incubation with cell type-specific antibodies that were directly labeled or that were detected by labeled secondary antibodies. Each cell type is known to possess certain surface antigens (so-called cluster of differentiation molecules, CD). The following cell (sub-)types were only quantified by flow cytometry:

- T cells, here quantified by $CD3^+$,
- cytotoxic T cells, specifically quantified by means of $CD3^+CD8^{+\prime}$
- helper T cells, specifically quantified by means of $CD3^+$ $CD4^+$
- regulatory T cells (Treg), specifically quantified by means of $CD4^+$, $CD25^+$, $CD127^-$,
- Natural killer cells (NK cells), specifically quantified by means of $CD3^-CD94^+$, or by means of $CD3^-CD45^+$ when working with purified NK cells,
- B cells, specifically quantified by means of $CD19^+$, and
- Monocytes/macrophages, specifically quantified by means of $CD14^+$.

The tumor cells and the stromal cells generally formed spheroids with a homogeneous appearance under the light microscope. Using immunohistochemistry on central tissue sections that had been prepared from formalin-fixed paraffin-embedded tissue blocks of PSN-1/MS5 spheroids, the inventors have surprisingly found that

- the spheroids were compact without holes (as determined by hematoxylin and eosins staining ((H&E)),
- CXCL12 was evenly distributed throughout the majority of the spheroid (as determined by staining with α-CXCL12 antibody); whereby staining in the central region was not successful or CXCL12 was not present in the center,
- tumor cells were present also in a majority of the spheroids (as determined by staining with α-pan cytokeratin that is only expressed by cells of epithelial origin i. e., cancer cells; but not by the stromal cell, and
- cells were vital (as determined by staining for the proliferation marker Ki-67), and no particular proliferative activity was observed in the zone where lymphocytes invaded (see below).

The respective experiments are described and shown in Example 7 and FIG. 14 respectively.

After overnight incubation of the PSN-1/MS5 spheroids with NK cells that were purified from PBMC from two human donors in the presence of various concentrations of NOX-A12, the inventors have surprisingly found that NK cell infiltration was enhanced by NOX-A12 in a dose-dependent manner (flow cytometry after spheroid dissociation, as shown in Example 8, FIGS. 16 and 21). This could be corroborated when PBMC were used. Moreover, in the latter experiment, B cell infiltration was also surprisingly found to be increased. Furthermore, T cell infiltration was increased. Monocytes/macrophages were hardly found and NOX-A12 did not increase them to a meaningful extent (see, Example 9, FIG. 17 A).

When analyzing T cell infiltration in greater detail, the inventors have found that Treg were increased only to a lower extent as compared to cytotoxic T cells and helper T cells (Example 9, FIG. 17 B). Immunohistochemistry also showed enhanced T cell infiltration. In the HT-29 spheroids this was only seen in the bottom hemisphere, as only this hemisphere had contact with the T cells. PSN-1 spheroids where repeatedly shaken during the incubation with T cells and showed therefore a more even T cell distribution (see, Example 7, FIG. 15). Of note: The T cell population of the donor that was used for the PSN-1 experiment showed a generalized lower motility than earlier and later T cell preparations.

Higher T cell numbers are unlikely to be due to a possible cell division of the lymphocytes after entering the spheroid; they are rather a consequence of a a more intense infiltration because cell division would have to be reflected in an intensive Ki-67 staining in the area of cell infiltration. However this was not observed (data not shown). Furthermore, overnight incubation is considered not sufficient for the increase to be due to proliferation.

All of the above suggests that enhanced tumor cell killing upon NOX-A12 treatment may be achievable—especially when downregulation of cellular attack by anti-inflammatory, "immune response dampening" molecules or molecular pathways, like PD-1/PD-L1, CTLA-4, LAG-3 or IDO are inhibited with corresponding drugs and/or the lymphocytes are armed with anti-tumor T-cell receptors (e.g. CAR-T cells), through tumor vaccination, through the use of T cell- or NK cell engaging agents, such as bispecific antibodies and/or the use of anti-tumor antibodies capable of inducing antibody-dependent cellular cytoroxicity which is generally mediated by NK cells.

Direct cytotoxicity is defined as as the cytotoxic effect exerted by a leukocyte or a subclass of leukocytes on another cell by means of a direct interaction as opposed to interactions that are mediated by a bridging molecule, e.g. an antibody, that binds to cellular eptiopes on both cells.

The general scheme of enhanced lymphocyte infiltration was confirmed by measuring T cell infiltration not only in PSN-1/MS5 tumor/stroma spheroids, but also in three further tumor/stroma spheroids as stated above (see, Example 10, FIG. 18). The use of higher NOX-A12 concentrations (up to 100 nM instead of up to 40 nM) revealed that there is an optimal NOX-A12 concentration. The inventors have found that a certain amount of CXCL12 still needs to be free in order to promote chemotaxis.

As a further model, the inventors established a 3D lymphoid microtissue model mimicking the stroma-rich and CXCL12-abundant tumor microenvironment of lymphoid malignancies in vitro. For this, pre-B cell lymphoma cells (Raji cells) were co-cultivated with CXCL12-expressing murine stromal cells (MS5 cells) in ultra-low attachment plates. Using this model, the inventors studied NK cell infiltration as well as antibody-dependent cellular cytotoxicity (ADCC) in the presence of anti-CD20 antibodies and NOX-A12. The inventors surprisingly found that NOX-A12 increased the amount of NK cells in the lymphoma-stroma spheroids up to 8-fold in a dose-dependent manner (see, Example 13, FIG. 22A). The basal NK cell infiltration was quite low. This resulted in a weak efficacy of an anti-CD20 mAb such as obinutzumab and rituximab as monotherapy. NOX-A12-induced infiltration of NK cells alone did not significantly influence the viability of the lymphoma cells. However, raising the number of NK cells in the microtissues by 10 nM NOX-A12 enhanced the lymphoma cell death in the presence of the anti-CD20 antibodies rituximab and obitunuzumab presumably through NK cell-mediated ADCC (see, FIG. 22BA, Dose-response of obinutuzumab and NOX-A12 allowed to determine a putative synergism of both drugs. Calculation with CompuSyn software based on Chou-Talalay's Combination Index Theorem (Chou 2010) revealed a combination index of 0.03, indicating a very strong synergistic effect (see, FIG. 22C).

In general, NK cell-mediated ADCC represents an important mode of action of therapeutic antibodies in cancer treatment. The combination of CXCL12 inhibition by NOX-A12 with antibodies targeting other receptors than CD20 plausibly also enhances ADCC.

The antibody-dependent cell-mediated cytotoxicity (ADCC) is a mechanism of cell-mediated immune defense, whereby an effector cell of the immune system actively lyses a target cell whose membrane-surface antigens have been bound by specific antibodies (Hashimoto et al., 1983). In humans, ADCC is usually mediated by IgG. It is one of the mechanisms through which antibodies, as part of the humoral immune response, can act to limit and contain infection (Pollara et al., 2011).

Classical antibody-dependent cell-mediated cytotoxicity is mediated by natural killer (NK) cells; but macrophages, neutrophils and eosinophils can also mediate it via antibodies (Hashimoto et al., 1983). For example, eosinophils can kill certain parasitic worms known as helminths through ADCC mediated by IgE. ADCC is part of the adaptive immune response due to its dependence on a prior antibody response. Typical ADCC involves activation of NK cells by antibodies, whereby NK cells express Fc receptors, mostly CD16. These receptors recognize, and bind to, the Fc portion of an antibody, such as IgG1, which has bound to the surface of a pathogen-infected target cell. Once the Fc receptor binds to the Fc region of IgG, the Natural Killer cell releases cytokines such as IFN-γ.

Similarly, during replication of a virus some of the viral proteins are expressed on the cell surface membrane of the infected cell. Antibodies can then bind to these viral proteins. Next, the NK cells which have Fc Receptors will bind to that antibody, inducing the NK cell to release proteins such as perforin and proteases known as granzymes, which causes the lysis of the infected cell to hinder the spread of the virus.

Furthermore, NK cells are involved in killing tumor cells and other cells that may lack MHC I on their surface, indicating a non-self cell. This is because, generally, all nucleated cells (which excludes RBCs) of the body contain MHC I.

ADCC is an important mechanism of action of therapeutic monoclonal antibodies (Clynes et al., 2000). In the following, monoclonal antibodies against a variety of cancer surface antigens, capable of inducing NK cell-mediated ADCC and which are FDA approved for the treatment of cancer are listed in the following. It is to be acknowledged that the antibodies were taken from the website indicated below listing all approved targeted therapies for cancer. Anti-cancer antibodies from this source were then individually checked by web research for NK-mediated ADCC. See, e. g., Abramson, R. 2016. Overview of Targeted Therapies for Cancer. My Cancer Genome https://www.mycancergenome.org/content/molecular-medicine/overview-of-targeted-therapies-for-cancer/(Updated August 8)):

alemtuzumab (α-CD52) for chronic lymphocytic leukemia, cetuximab (α-EGFR) for metastatic colorectal cancer, head and neck cancer, daratumumab (α-CD38) for multiple myeloma, elotuzumab (SLAMF7 (CS1/CD319/CRACC)) for multiple myeloma, ofatumumab (α-CD20) for chronic lymphocytic leukemia, pertuzumab (HER2 (ERBB2/neu)) for breast cancer ($HER2^+$), and trastuzumab (HER2) for breast cancer.

T cell activation and tumor killing cannot be observed in in vitro assays with donor T cells. Therefore, a commercially Bioluminescent Reporter-Based PD-1/PD-L1 Blockade Bioassay (Promega) was used. This assay uses CHO cells stably expressing human PD-L1 and a T cell receptor (TCR) activator and act as antigen presenting cells (PD-L1+ cells) or "tumor cells". Reporter cells for T cell activation are Jurkat cells that express PD-1 and express luciferase under the control of the Nuclear factor of activated T-cells (NFAT) signaling pathway. Thereby the luminescence signal that can be recorded upon addition of the luciferase substrate (Bio-Glo) increases with T cell activation.

NOX-A12 was found to enhance T cell infiltration into the $CHO^{PD\text{-}L1}$/MS5 tumor/stroma spheroids as shown by flow cytometry with an anti CD45 antibody. The anti-programmed cell death 1 (αPD-1) antibody did not influence the infiltration of the T cells into the spheroid, neither with nor without NOX-A12 (see, Example 11, FIG. 19 A). A reduced number of Jurkat T cells around the spheroid, in the wells containing NOX-A12 was also visible under the microscope (see, Example 11, FIG. 19 B).

Surprisingly, the effect of the αPD-1 antibody on T cell activation (luminescence) was limited. While in 2-D assays there is a clear proportionality over a wide concentration range, the T cell activation was blunted on a low level in the 3-D microtissue assay. In contrast to this, NOX-A12, although not activating the T cells in the absence of a spheroid (data not shown), promoted T cell activation when added alone. The inventors have found that this is due to the fact that more T cells come into contact with the TCR activating "tumor cells". Thereby, in the 3-D situation, blockade of CXCL12 with a soluble ligand was more potent than immune checkpoint inhibition. Adding the immune checkpoint inhibitor, the anti-PD-1 antibody, further increased the T cell activation. Synergy calculations proved that the effects were synergistic at all concentrations tested (combination index<1)(Chou 2010).

The synergistic effect of NOX-A12 and anti-PD-1 was corroborated in vivo in the syngeneic CT-26 mouse model of undifferentiated, refractory colorectal cancer. The CT-26 model is characterized by poor sensitivity to checkpoint inhibition as monotherapy. While treatment of the single agents NOX-A12 or anti-PD-1 had no significant effect on tumor growth inhibition, NOX-A12 enhanced or facilitated the efficacy of anti-PD1 treatment (see, Example 12, FIG. 20A). The fraction of mice responding to treatment was increased from 2 out of 8 in the anti-PD1 group and 1 out of 8 in in the NOX-A12 group to 5 out of 8 in the combination group (see, FIG. 20B).

Using immunohistochemistry, the distribution of CXCL12 was found to be quite evenly spread within certain tumors and metastases, respectively, or at least within substructures within the tumor. Respective examples were: metastases of lung and renal carcinoma as well as multiple myeloma (Roccaro, Sacco et al. 2014). Without wishing to be bound by any theory, the inventors have found that leukocytes that would normally follow CXCL12 gradients do not receive further directional cues once inside the solid tumor tissue and thus remain close to the adjacent tissue or the vasculature or may even re-enter the vasculature.

By administering a diffusible inhibitor of SDF-1, such as NOX-A12, CXCL12 around the vasculature is partially bound and neutralized. The inhibitor thereby creates or at least enhances microgradients around the vasculature into the solid tumor and metastasis, respectively, which the leukocytes can follow. Thereby more leukocytes can come into contact with more tumor cells. This can enhance T cell and NK cell attack, ADCC, leukocyte engagement and tumor cell killing by multi-valent drugs such as bispecific antibodies, and also promote B cell-driven anti-tumor response. The importance of CXCL12 is underscored by the finding that a concentration of 100 nM NOX-A12 again leads to a reduction of cellular infiltration. Obviously, at higher concentrations a high fraction of the CXCL12 in the margin is neutralized so that the chemotactic cue is missing.

The tumor/stroma spheroids the inventors have used in this model also showed a relatively even distribution of CXCL12 with no decrease towards the margin, and may therefore serve well as a surrogate for a solid tumor.

The facts described here for solid tumors are clearly different from the spongey, loosely associated bone marrow in which there are clear CXCL12 gradients in normal physiology. These gradients are located in the bone marrow—between the stem cell niches comprising CXCL12-abundant reticular cells and the fenestrated sinusoids—where more fluid exchange is present. In bone marrow and lymphoid tissues NOX-A12 acts as a mobilizer of a wide range of leukocytes (Vater et al. 2013). Together with the enhancement of lymphocyte infiltration, one can speak of a redistribution of lymphocytes such as and including T cells, NK cells, B cells, from bone marrow or lymphoid tissues to the tumor.

As to the various diseases, conditions and disorders which may be treated or prevented by using the nucleic acid molecules according to the present invention or compositions, preferably a pharmaceutical composition, and, respectively, medicament comprising the same, it has to be acknowledged that such diseases, conditions and disorders are those which are described herein, including and in particular those described and set forth in the introductory part of the instant application. Insofar, the respective passages form an integral part of the present disclosure teaching the suitability of the nucleic acid molecules for the prevention and treatment, respectively, for said diseases, conditions, and disorders.

As used herein the term SDF-1 refers to any SDF-1 including, but not limited to, mammalian SDF-1. Preferably, the mammalian SDF-1 is selected from the group comprising mice, rat, rabbit, hamster, monkey and human SDF-1. More preferably the SDF-1 is human SDF-1 also referred to as SDF-1α (SEQ ID NO: 1) and/or human SDF-1β (SEQ ID NO: 2), most preferably human SDF-1 also referred to as SDF-1α (SEQ ID NO: 1).

SDF-1 acts through two different receptors, the receptors CXCR4 and RDC1/CXCR7 (Balabanian, Lagane et al. 2005a, Burns, Summers et al. 2006) (see the introductory part of the instant application). Elevated expression of CXCR4 and CXCR7 was shown for several cancer types as described herein.

Because SDF-1 acts through two different receptors, treatment of an SDF-1 related disease or disorder by a compound specific for one out of the two SDF-1 receptors CXCR4 and CXCR7 a) should be less effective due to the two different SDF-1 receptors expressed on cells, preferably cancer cells; and
b) is limited to a distinct population of cells, particularly to a distinct population of cancer cells, due to the individual SDF-1 receptors expressed on the cells.

Cancer as preferably used herein is a term for malignant neoplasms, and encompasses a great and heterogeneous group of diseases in which cells display uncontrolled growth, invasion and often metastasizes, wherein cancer cells spread to other locations in the body, to regional lymph nodes or distant body sites like brain, bone, liver, and other organs. These three malignant properties of cancer differentiate malignant tumors from benign tumors, whereby, as preferably used herein, the term cancer shall also encompass malignant tumors which in turn are also referred to herein as tumors. Malignant tumors fall into two categories based on their origin: Hematological and solid tumors. Hematological tumors are cancer types or forms of cancer affecting blood, bone marrow, and lymph nodes. Solid tumors are formed by an abnormal growth of body tissue cells other than blood, bone marrow or lymphatic cells.

Preferred forms of cancer which may be treated in accordance with the present invention are the following ones:

Adrenocortical Carcinoma
AIDS-Related Cancers such as Kaposi Sarcoma and Lymphoma
Anal Cancer
Appendix Cancer
Atypical Teratoid/Rhabdoid Tumor
Basal Cell Carcinoma
Bile Duct Cancer, Extrahepatic
Bladder Cancer
Bone Cancer
Osteosarcoma
Malignant Fibrous Histiocytoma
Brain Stem Glioma
Brain Tumor such as Astrocytomas, Brain and Spinal Cord Tumors, Brain Stem Glioma, Childhood, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma Breast Cancer Bronchial Tumors Carcinoid Tumor Carcinoma of Unknown Primary Cancer of Central Nervous System such as Atypical Teratoid/Rhabdoid Tumor and Lymphoma Cervical Cancer Childhood Cancers Chordoma Chronic Myeloproliferative Disorders Colon Cancer Colorectal Cancer Craniopharyngioma Cutaneous T-Cell Lymphoma Embryonal Tumors Endometrial Cancer Ependymoblastoma Ependymoma, Esophageal Cancer Esthesioneuroblastoma Ewing Sarcoma Family of Tumors Extracranial Germ Cell Tumor Extragonadal Germ Cell Tumor Extrahepatic Bile Duct Cancer Eye Cancer such as Intraocular Melanoma and Retinoblastoma Fibrous Histiocytoma of Bone Osteosarcoma Gallbladder Cancer Gastric (Stomach) Cancer Gastrointestinal Carcinoid Tumor Gastrointestinal Stromal Tumors (GIST)

Germ Cell Tumor (extracranial, extragonadal or ovarian)

Gestational Trophoblastic Tumor

Glioma

Hairy Cell Leukemia

Head and Neck Cancer

Heart Cancer

Hepatocellular (Liver) Cancer

Histiocytosis

Hypopharyngeal Cancer

Intraocular Melanoma

Islet Cell Tumors (Endocrine Pancreas)

Kaposi Sarcoma

Kidney Cancer

Langerhans Cell Histiocytosis

Laryngeal Cancer

Leukemia such Acute Lymphoblastic Leukemia (abbr. ALL), Acute Myeloid Leukemia (abbr. AML), Chronic Lymphocytic Leukemia (abbr. CLL), Chronic Myelogenous Leukemia (abbr. CML) and Hairy Cell Leukemia Lip and Oral Cavity Cancer Liver Cancer (Primary)

Lobular Carcinoma In Situ (LCIS)

Lung Cancer

Lymphoma such as AIDS-Related Lymphoma, Burkitt, Mycosis Fungoides and Sézary Syndrome, Hodgkin, Non-Hodgkin and leukemia of Primary Central Nervous System (abbr. CNS)

Macroglobulinemia

Malignant Fibrous Histiocytoma of Bone and Osteosarcoma

Medulloblastoma

Medulloepithelioma

Melanoma

Merkel Cell Carcinoma

Mesothelioma

Metastatic Squamous Neck Cancer with Occult Primary

Midline Tract Carcinoma Involving NUT Gene

Mouth Cancer

Multiple Endocrine Neoplasia Syndromes

Multiple Myeloma

Mycosis Fungoides

Myelodysplastic Syndromes

Myelodysplastic/Myeloproliferative Neoplasms

Myeloproliferative Disorders

Nasal Cavity and Paranasal Sinus Cancer

Nasopharyngeal Cancer

Neuroblastoma

Non-Small Cell Lung Cancer

Oral Cancer

Oral Cavity Cancer

Oropharyngeal Cancer

Osteosarcoma and Malignant Fibrous Histiocytoma of Bone

Ovarian Cancer

Pancreatic Cancer

Papillomatosis

Paraganglioma

Paranasal Sinus and Nasal Cavity Cancer

Parathyroid Cancer

Penile Cancer

Pharyngeal Cancer

Pheochromocytoma

Pineal Parenchymal Tumors of Intermediate Differentiation

Pineoblastoma and Supratentorial Primitive Neuroectodermal Tumors

Pituitary Tumor

Plasma Cell Neoplasm/Multiple Myeloma

Pleuropulmonary Blastoma, Childhood

Primary Central Nervous System (abbr CNS) Lymphoma

Prostate Cancer

Rectal Cancer

Renal Cell (Kidney) Cancer

Renal Pelvis and Ureter, Transitional Cell Cancer

Retinoblastoma

Rhabdomyosarcoma

Salivary Gland Cancer

Sarcoma such as Ewing Sarcoma Family of Tumors, Kaposi Sarcoma, Soft Tissue Sarcoma, Uterine Sarcoma Skin Cancer such Melanoma, Merkel Cell Carcinoma and Nonmelanoma Small Cell Lung Cancer Small Intestine Cancer Soft Tissue Sarcoma Squamous Cell Carcinoma Squamous Neck Cancer Stomach (Gastric) Cancer Supratentorial Primitive Neuroectodermal Tumors T-Cell Lymphoma Testicular Cancer Throat Cancer Thymoma and Thymic Carcinoma Thyroid Cancer Transitional Cell Cancer of the Renal Pelvis and Ureter Trophoblastic Tumor, Gestational Ureter and Renal Pelvis, Transitional Cell Cancer
Urethral Cancer
Uterine Cancer, Endometrial
Uterine Sarcoma
Vaginal Cancer
Vulvar Cancer
Waldenström Macroglobulinemia
Wilms Tumor The SDF-1-CXCR4 axis has been shown to play a role in stem cell mobilization including cancer stem cells, vasculogenesis, tumor growth and metastasis. The SDF-1 receptor CXCR4 is expressed in a variety of cancers and hematological malignancies in vivo as is CXCR7 (Maksym, Tarnowski et al., 2009; Wang, Shiosawa et al., 2008; Miao, Lucker et al., 2007). The growth and invasion signal for tumor cells is SDF-1, in particulaur if the cells express the receptors for SDF-1 (Batchelor et al., 2007; Zhu et al., 2009; Xu et al., 2009; Kozin et al., 2010).

CXCR4 as well as SDF-1 are induced by hypoxia (Ceradini et al. 2004). Together with VEGF they represent a potent synergistic axis that initiates and maintains angiogenic/vascologenic pathways (Kryczek et al. 2005). The role in vasculogenesis is supported by evidence that SDF-1 attracts CXCR4 expressing endothelial progenitor cells from the circulation (Sengupta et al. 2005). SDF-1-CXCR4 mediated recruitment of bone marrow derived cells that support vascularization may also be the reason for recurrence of glioblastoma after irradiation therapy (Kioi et al., 2010). As demonstrated by Kioi et al. in an intracranial glioblastoma multiforme (abbr. GBM) mouse xenograft model, the treatment of GBM patients with high dosis of radiation is less effective due to irradiation induced recruitment of bone-marrow derived cells (abbr. BMDCs). The blockade of the interaction of SDF-1 and its receptor CXCR4 by the CXCR4 antagonist AMD3100 prevented the influx of BMDCs in the irradiated tumor (Kioi et al., 2010). In 2010 Tseng et al. (Tseng et al., 2010) presented data with an ENU induced glioblastoma rat model, a model that closely mimics human GBM, that besides CXCR4 also CXCR7 is involved in irradiation induced recruitment of BMDCs. In this study the CXCR7 antagonist CCX2206 prevented the influx of BMDCs in the irradiated tumor (Tseng et al., 2010). In accordance therewith and because the nucleic acid molecules according to the present invention are able to block the interation of both SDF-1 and CXCR4 and SDF-1 and CXCR7, the effect on survival after irradiation is expected to be better than shown for the use of one of the CXCR4 and CXCR7 antagonists alone.

In addition, SDF-1 induces VEGF secretion, while VEGF increases CXCR4 expression (Salcedo et al. 1999) and angiogenesis signals. Therefore, inhibition of the SDF-1-CXCR4 axis may reduce or prevent tumor growth by inhibition of angiogenesis/vasculogenesis either with monotherapy or particularly in combination with other antivascular agents such as VEGF inhibitors.

Furthermore, it is suggested that 'homing' of CXCR4 expressing cancer cells to SDF-1-expressing organs directs metastatic cells preferentially to the liver, bone marrow, lung and lymph nodes (Alsayed et al. 2007; Burger & Peled 2009) and, therefore, the SDF-1-CXCR4 axis plays a role in metastasis, too.

Hence, the inhibition of the SDF-1-CXCR4 axis and of the SDF-1-CXCR7 axis with only one compound such as the SDF-1 binding nucleic acid molecule according to the present invention, should be effective in treating cancer and/or tumors, in particular a wide range of both haematological and solid tumors either as monotherapy or in combination with other treatments such as, but not limited to, drug therapy, cellular therapy, irradiation and surgery. Moreover, in comparison to a compound that binds and inhibits one out of the two SDF-1 receptors CXCR4 and CXCR7, the inhibition of the SDF-1-CXCR4 axis and of the SDF-1-CXCR7 axis with only one compound such as the SDF-1 binding nucleic acid molecule according to the present invention should be more effective in treating cancer and/or tumors, in particular a wide range of both haematological and solid tumors either as monotherapy or in combination with other treatments including, but not limited to drug therapy, cellular therapy, irradiation and surgery.

It is within the present invention that drug therapy comprises the treatment and/or prevention of a disease or disorder by a drug, preferably a pharmaceutically active agent, more preferably a pharmaceutically active agent as defined herein.

As preferably used herein, in cell therapy also referred to as cellular therapy, processed tissue from the organs, embryos, or fetuses of animals such as sheep or cows is injected into a subject suffering from or being at risk of developing a disease or disorder, whereby preferably the disease or disorder is cancer and cell therapy a form of cancer treatment.

In theory, non-hematological cancers can be cured if entirely removed by surgery. When the cancer has metastasized to other sites in the body prior to surgery, complete surgical excision is usually impossible. Examples of surgical procedures or surgery for cancer include mastectomy for breast cancer, prostatectomy for prostate cancer, and lung cancer surgery for non-small cell lung cancer. The goal of the surgery can be either the removal of only the tumor, or of the entire organ. Surgery is often combined, with other cancer treatments or therapies, such as chemotherapy and radiation. Cancer surgery may be used to achieve one or more goals. Such goals may include, but are not limited to, cancer prevention, diagnosis, staging, primary treatment, debulking and relieving symptoms or side effects.

Radiotherapy (also referred to X-ray therapy or irradiation) is the use of ionizing radiation to kill cancer cells. Radiotherapy is used in the medical art to treat almost every type of solid tumor. Irradiation is also used to treat leukemia and lymphoma. Radiotherapy injures or destroys cells in the area being treated by damaging their genetic material, making it impossible for these cells to continue to grow and divide. The effects of radiotherapy are localized and confined to the region being treated. Radiation dose to each site depends on a number of factors, including the radiosensitivity of each cancer type and whether there are tissues and organs nearby that may be damaged by radiation. The goal of radiotherapy is to damage as many cancer cells as possible, while limiting harm to nearby healthy tissue.

Additionally, an SDF-1 binding nucleic molecule according to the present invention is preferred if the physiological effect of the SDF-1-CXCR4 axis and/or of the SDF-1-CXCR7 axis is related to higher plasma levels of SDF-1. For instance, particular therapeutic agents such as paclitaxel and bevacizumab produce an elevation of plasma SDF-1 levels which can have a negative effect on tumor therapy by releasing more bone marrow derived endothelial progenitor cells or by stimulating growth, invasiveness or metastasis (Shaked, Henke et al., 2008; Xu, Duda et al., 2009). In this case, co-application of an SDF-1 binding nucleic acid such as the SDF-1 binding nucleic acids of the present invention will ameliorate the effects of elevated plasma SDF-1 levels.

Moreover, the inhibition of the SDF-1-CXCR4 axis and/or of the SDF-1-CXCR7 axis by an SDF-1 binding nucleic molecule according to the present invention will enhance the anti-tumor effects of other therapeutic agents by disrupting the adhesive stromal interactions with leukemia and other cancer cells that confer survival and drug resistance to these therapies (Jin et al., 2008; Nervi et al., 2009). Such use of SDF-1 binding nucleic molecule is known as a process known as chemosensitization.

The sensitization of tumor cells to chemotherapy or radiotherapy is known as 'chemosensitization'. or 'radiosensitization', respectively. Such 'chemosensitization' or 'radiosensitization', preferably by the nucleic acid molecules according to the present invention, sensitizes the subject suffering from a disease or disorder, whereby the sensitized subject is more responsive to a therapy for the treatment and/or prevention of the disease or disorder, whereby preferably the disease or the disorder is cancer. Such treatment used together with a primary treatment, preferably a cancer treatment, is an adjunct therapy according to the present invention and also referred to as adjunctive therapy. The purpose of such adjunct therapy is to assist a primary treatment, preferably a primary cancer treatment. Hence, the inhibition of the SDF-1-CXCR4 axis and/or SDF-1-CXCR7 axis will be particularly effective in treating a wide range of both haematological and solid tumors either as monotherapy or in combination with other treatments, including but not limited to, drug therapy, cellular therapy, irradiation and surgery.

By these means and in view of the outlined involvement of SDF-1 and SDF-1 receptors—such as CXCR4 and CXCR7—the SDF-1 binding and the interaction between SDF-1 and SDF-1 receptor inhibiting nucleic acid molecules according to the present invention can help to attenuate such diseases, whereby inhibition of SDF-1 by the SDF-1 binding nucleic acid molecules according to the present invention leads to chemosensitization of malignant cells to be treated by chemotherapy, reduction or inhibition of growth and invasiveness, inhibition of angiogenesis/vasculogenesis, inhibition of metastasis and/or inhibition of elevated plasma SDF-1 levels derived from the response of the host to chemotherapy.

Moreover, the present invention is based on the surprising finding that it is possible to generate nucleic acid molecules binding specifically and with high affinity to SDF-1, thereby inhibiting and antagonizing the effects of SDF-1, in particular the effects of SDF-1 on its receptors such as CXCR4 and CXCR7.

An antagonists to SDF-1 is a molecule that binds to SDF-1—such as the SDF-1 binding nucleic acid molecules according to the present invention—and inhibits the function of SDF-1, preferably in an in vitro assay or in an in vivo model as described in the Examples.

It is within the present invention that the nucleic acid according to the present invention is a nucleic acid molecule. Insofar the terms nucleic acid and nucleic acid molecule are used herein in a synonymous manner if not indicated to the contrary. Moreover, such nucleic acids are preferably also referred to herein as the nucleic acid molecules according to the present invention, the nucleic acids according to the present invention, the inventive nucleic acids or the inventive nucleic acid molecules.

The features of the nucleic acid according to the present invention as described herein can be realised in any aspect and embodiment, respectively, of the present invention where the nucleic acid is used, either alone or in any combination.

As outlined in more detail herein, the present inventors have identified a number of different SDF-1 binding nucleic acid molecules, whereby the nucleic acid molecules can be characterised in terms of stretches of nucleotides which are also referred to herein as Boxes (see, Example 1).

The different types of SDF-1 binding nucleic acid molecules comprise three different stretches of nucleotides: the first terminal stretch of nucleotides, the central stretch of nucleotides and second terminal stretch of nucleotides. In general, SDF-1 binding nucleic acid molecules of the present invention comprise at their 5'-end and the 3'-end the terminal stretches of nucleotides: the first terminal stretch of nucleotides and the second terminal stretch of nucleotides (also referred to as 5'-terminal stretch of nucleotides and 3'-terminal stretch of nucleotides). The first terminal stretch of nucleotides and the second terminal stretch of nucleotides can, in principle due to their base complementarity, hybridize to each other, whereby upon hybridization a double-stranded structure is formed. However, such hybridization is not necessarily realized in the molecule under physiological and/or non-physiological conditions. The three stretches of nucleotides of SDF-1 binding nucleic acid molecules—the first terminal stretch of nucleotides, the central stretch of nucleotides and second terminal stretch of nucleotides—are arranged to each other in 5'→3'-direction: the first terminal stretch of nucleotides—the central stretch of nucleotides—the second terminal stretch of nucleotides. However, alternatively, the second terminal stretch of nucleotides, the central stretch of nucleotides and the terminal first stretch of nucleotides are arranged to each other in 5'→3'-direction.

The differences in the sequences of the defined boxes or stretches between the different SDF-1 binding nucleic acid molecules influence the binding affinity to SDF-1. Based on binding analysis of the different SDF-1 binding nucleic acid molecules of the present invention the central stretch and the nucleotides forming the same are individually and more preferably in their entirety essential for binding to human SDF-1.

The terms 'stretch' and 'stretch of nucleotide' are used herein in a synonymous manner if not indicated to the contrary.

In a preferred embodiment the nucleic acid according to the present invention is a single nucleic acid molecule. In a further embodiment, the single nucleic acid molecule is present as a multitude of the single nucleic acid molecule or as a multitude of the single nucleic acid molecule species.

It will be acknowledged by the ones skilled in the art that the nucleic acid molecule in accordance with the invention preferably consists of nucleotides which are covalently linked to each other, preferably through phosphodiester links or linkages.

It is within the present invention that the nucleic acids according to the present invention comprise two or more stretches or part(s) thereof can, in principle, hybridise with each other. Upon such hybridisation a double-stranded structure is formed. It will be acknowledged by the ones skilled in the art that such hybridisation may or may not occur, particularly under in vitro and/or in vivo conditions. Also, in case of such hybridisation, it is not necessarily the case that the hybridisation occurs over the entire length of the two stretches where, at least based on the rules for base pairing, such hybridisation and thus formation of a double-stranded structure may, in principle, occur. As preferably used herein, a double-stranded structure is a part of a nucleic acid molecule or a structure formed by two or more separate strands or two spatially separated stretches of a single strand of a nucleic acid molecule, whereby at least one, preferably two or more base pairs exist which are base pairing preferably in accordance with the Watson-Crick base pairing rules.

It will also be acknowledged by the one skilled in the art that other base pairing such as Hoogsten base pairing may exist in or form such double-stranded structure. It is also to be acknowledged that the feature that two stretches hybridize preferably indicates that such hybridization is assumed to happen due to base complementarity of the two stretches.

In a preferred embodiment the term arrangement as used herein, means the order or sequence of structural or functional features or elements described herein in connection with the nucleic acids disclosed herein.

It will be acknowledged by the person skilled in the art that the nucleic acids according to the present invention are capable of binding to SDF-1. Without wishing to be bound by any theory, the present inventors have found that the SDF-1 binding results from a combination of three-dimensional structural traits or elements of the claimed nucleic acid molecule, which are caused by orientation and folding patterns of the primary sequence of nucleotides forming such traits or elements, whereby preferably such traits or elements are the first terminal stretch of nucleotides, the central stretch of nucleotides and the second terminal stretch of nucleotides of SDF-1 binding nucleic acid molecules. It is evident that the individual trait or element may be formed by various different individual sequences the degree of variation of which may vary depending on the three-dimensional structure such element or trait has to form. The overall binding characteristic of the claimed nucleic acid results from the interplay of the various elements and traits, respectively, which ultimately results in the interaction of the claimed nucleic acid with its target, i. e. SDF-1. Again without being wished to be bound by any theory, the central stretch of nucleotides that is characteristic for SDF-1 binding nucleic acids seems to be important for mediating the binding of the claimed nucleic acid molecules with SDF-1. Accordingly, the nucleic acids according to the present invention are suitable for the interaction with SDF-1. Also, it will be acknowledged by the person skilled in the art that the nucleic acids according to the present invention are antagonists to SDF-1. Because of this, the nucleic acids according to the present invention are suitable for the treatment and prevention, respectively, of any disease or condition which is associated with or caused by SDF-1. Such diseases and conditions may be taken from the prior art which establishes that SDF-1 is involved or associated with said diseases and conditions, respectively, and which is incorporated herein by reference providing the scientific rationale for the therapeutic use of the nucleic acids according to the invention. Insofar it is also and particularly referred to the introductory part of the instant application which is incorporated herewith by reference.

The nucleic acids according to the present invention shall also comprise nucleic acids which are essentially homologous to the particular sequences disclosed herein. The term substantially homologous shall be understood such as the homology is at least 75%, preferably 85%, more preferably 90% and most preferably more that 95%, 96%, 97%, 98% or 99%.

The actual percentage of homologous nucleotides present in the nucleic acid according to the present invention will depend on the total number of nucleotides present in the nucleic acid. The percent modification can be based upon the total number of nucleotides present in the nucleic acid.

The homology between two nucleic acid molecules can be determined as known to the person skilled in the art. More specifically, a sequence comparison algorithm may be used for calculating the percent sequence homology for the test sequence(s) relative to the reference sequence, based on the designated program parameters. The test sequence is preferably the sequence or nucleic acid molecule which is said to be homologous or to be tested whether it is homologous, and if so, to what extent, to a different nucleic acid molecule, whereby such different nucleic acid molecule is also referred to as the reference sequence. In an embodiment, the reference sequence is a nucleic acid molecule as described herein, preferably a nucleic acid molecule having a sequence according to any one of SEQ ID NO: 5 to SEQ ID NO: 225, more preferably a nucleic acid molecule having a sequence according to any one of SEQ ID NO: 22, SEQ ID NO: 28, SEQ ID NO: 120, SEQ ID NO: 128, SEQ ID NO: 129, SEQ ID NO: 134, SEQ ID NO: 135, SEQ ID NO: 223, SEQ ID NO: 224, SEQ ID NO: 84, SEQ ID NO: 146, SEQ ID NO: 142, SEQ ID NO: 143, and SEQ ID NO: 144. Optimal alignment of sequences for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson & Lipman (Pearson & Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g. Altschul et al (Altschul et al. 1990 and Altschul et al, 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al (McGinnis et al, 2004).

The nucleic acids according to the present invention shall also comprise nucleic acids which have a certain degree of identity relative to the nucleic acids disclosed herein and defined by their nucleotide sequence. More preferably, the instant invention also comprises those nucleic acid molecules which have an identity of at least 75%, preferably 85%, more preferably 90% and most preferably more than 95%, 96%, 97%, 98% or 99% relative to the nucleic acids disclosed herein and defined by their nucleotide sequence or a part thereof.

The term inventive nucleic acid or nucleic acid according to the present invention shall also comprise those nucleic acids comprising the nucleic acids sequences disclosed herein or part thereof, such as, e.g., a metabolite or derivative of the nucleic acid according to the present invention, preferably to the extent that the nucleic acids or said parts are involved in the or capable of binding to SDF-1. Such a nucleic acid may be derived from the ones disclosed herein, e.g., by truncation. Truncation may be related to either or both of the ends of the nucleic acids as disclosed herein. Also, truncation may be related to the inner sequence of nucleotides, i.e. it may be related to the nucleotide(s) between the 5' and the 3' terminal nucleotide, respectively. Moreover, truncation shall comprise the deletion of as little as a single nucleotide from the sequence of the nucleic acids disclosed herein. Truncation may also be related to more than one stretch of the inventive nucleic acid(s), whereby the stretch can be as little as one nucleotide long. The binding of a nucleic acid according to the present invention can be determined by the ones skilled in the art using routine experiments or by using or adopting a method as described herein, preferably as described herein in the example part.

The nucleic acids according to the present invention may be either D-nucleic acids or L-nucleic acids. Preferably, the inventive nucleic acids are L-nucleic acids. In addition it is possible that one or several parts of the nucleic acid are present as D-nucleic acids or at least one or several parts of the nucleic acids are L-nucleic acids. The term "part" of the nucleic acids shall mean as little as one nucleotide. Such nucleic acids are generally referred to herein as D- and L-nucleic acids, respectively. Therefore, in a particularly preferred embodiment, the nucleic acids according to the present invention consist of L-nucleotides and comprise at least one D-nucleotide. Such D-nucleotide is preferably attached to a part different from the stretches defining the nucleic acids according to the present invention, preferably those parts thereof, where an interaction with other parts of the nucleic acid is involved. Preferably, such D-nucleotide is attached at a terminus of any of the stretches and of any nucleic acid according to the present invention, respectively. In a further preferred embodiment, such D-nucleotides may act as a spacer or a linker, preferably attaching modifications such as PEG and HES to the nucleic acids according to the present invention.

It is also within the present invention that each and any of the nucleic acid molecules described herein in their entirety in terms of their nucleic acid sequence(s) are limited to the particular nucleotide sequence(s). In other words, the terms "comprising" or "comprise(s)" shall be interpreted in such embodiment in the meaning of containing or consisting of.

It is also within the present invention that the nucleic acids according to the present invention are part of a longer nucleic acid, whereby this longer nucleic acid comprises several parts, whereby at least one such part is a nucleic acid, or a part thereof, according to the present invention. The other part(s) of these longer nucleic acids can be either one or several D-nucleic acid(s) or L-nucleic acid(s). Any combination may be used in connection with the present invention. These other part(s) of the longer nucleic acid can exhibit a function which is different from binding, preferably from binding to SDF-1. One possible function is to allow interaction with other molecules, whereby such other molecules preferably are different from SDF-1, such as, e.g., for immobilization, cross-linking, detection or amplification. In a further embodiment of the present invention the nucleic acids according to the invention comprise, as individual or combined moieties, several of the nucleic acids of the present invention. Such nucleic acid comprising several of the nucleic acids of the present invention is also encompassed by the term longer nucleic acid.

L-nucleic acids as used herein are nucleic acids consisting of L-nucleotides, preferably consisting completely of L-nucleotides.

D-nucleic acids as used herein are nucleic acids consisting of D-nucleotides, preferably consisting completely of D-nucleotides.

The terms nucleic acid and nucleic acid molecule are used herein in an interchangeable manner if not explicitly indicated to the contrary.

Also, if not indicated to the contrary, any nucleotide sequence is set forth herein in 5'→3' direction.

As preferably used herein, any position of a nucleotide is determined or referred to relative to the 5' end of a sequence, a stretch or a substretch. Accordingly, a second nucleotide is the second nucleotide counted from the 5' end of the sequence, stretch and substretch, respectively. Also, in accordance therewith, a penultimate nucleotide is the second nucleotide counted from the 3' end of a sequence, stretch and substretch, respectively.

Irrespective of whether the inventive nucleic acid consists of D-nucleotides, L-nucleotides or a combination of both with the combination being, e.g., a random combination or a defined sequence of stretches consisting of at least one L-nucleotide and at least one D-nucleic acid, the nucleic acid may consist of desoxyribonucleotide(s), ribonucleotide(s) or combinations thereof.

Designing the inventive nucleic acids as L-nucleic acid is advantageous for several reasons. L-nucleic acids are enantiomers of naturally occurring D-nucleic acids. D-nucleic acids, however, are not very stable in aqueous solutions and particularly in biological systems or biological samples due to the widespread presence of nucleases. Naturally occurring nucleases, particularly nucleases from animal cells are not capable of degrading L-nucleic acids. Because of this, the biological half-life of the L-nucleic acid is significantly increased in such a system, including the animal and human body. Due to the lacking degradability of L-nucleic acid no nuclease degradation products are generated and thus no side effects arising therefrom are observed. This aspect delimits the L-nucleic acid of factually all other compounds which are used in the therapy of diseases and/or disorders involving the presence of SDF-1. L-nucleic acids which specifically bind to a target molecule through a mechanism different from Watson Crick base pairing, or aptamers which consists partially or completely of L-nucleotides, particularly with those parts of the aptamer being involved in the binding of the aptamer to the target molecule, are also called spiegelmers. Aptamers and spiegelmers as such are known to a person skilled in the art and are, among others, described in 'The Aptamer Handbook' (eds. Klussmann, 2006).

It is also within the present invention that the inventive nucleic acids, regardless whether they are present as D-nucleic acids, L-nucleic acids or D,L-nucleic acids or whether they are DNA or RNA, may be present as single stranded or double stranded nucleic acids. Typically, the inventive nucleic acids are single stranded nucleic acids which exhibit defined secondary structures due to the primary sequence and may thus also form tertiary structures. The inventive nucleic acids, however, may also be double stranded in the meaning that two strands which are complementary or partially complementary to each other, are hybridised to each other or at least may be hybridised to each other in light of their base complementarity.

The inventive nucleic acids may be modified. Such modifications may be related to a single nucleotide of the nucleic acid and are well known in the art. Examples for such modification are described by, among others, Venkatesan et al. (Venkatesan, Kim et al., 2003) and Kusser (Kusser, 2000). Such modification can be a H atom, an F atom or O—$CH_3$ group or $NH_2$-group at the 2' position of the individual nucleotide of which the nucleic acid consists. Also, the nucleic acid according to the present invention can comprises at least one LNA nucleotide. In an embodiment the nucleic acid according to the present invention consists of LNA nucleotides.

In an embodiment, the nucleic acids according to the present invention may be a multipartite nucleic acid. A multipartite nucleic acid as used herein, is a nucleic acid which consists of at least two separate nucleic acid strands. These at least two nucleic acid strands form a functional unit whereby the functional unit is a ligand to a target molecule. The at least two nucleic acid strands may be derived from any of the inventive nucleic acids by either cleaving the nucleic acid molecule to generate two strands or by synthesising one nucleic acid corresponding to a first part of the inventive, i.e. overall nucleic acid and another nucleic acid corresponding to the second part of the overall nucleic acid. It is to be acknowledged that both the cleavage and the synthesis may be applied to generate a multipartite nucleic acid where there are more than two strands as exemplified above. In other words, the at least two separate nucleic acid strands are typically different from two strands being complementary and hybridising to each other although a certain extent of complementarity between said at least two separate nucleic acid strands may exist and whereby such complementarity may result in the hybridisation of said separate strands.

Finally, it is also within the present invention that a fully closed, i.e. circular structure for the nucleic acids according to the present invention is realized, i.e. that the nucleic acids according to the present invention are closed in an embodiment, preferably through a covalent linkage, whereby more preferably such covalent linkage is made between the 5' end and the 3' end of the nucleic acid sequences as disclosed herein or any derivative thereof.

A possibility to determine the binding constants of the nucleic acid molecules according to the present invention is the use of the methods as described in Examples 3 and 4 which confirms the above finding that the nucleic acids according to the present invention exhibit a favourable $K_D$ value range. An appropriate measure in order to express the intensity of the binding between the individual nucleic acid molecule and the target which is in the present case SDF-1, is the so-called $K_D$ value which as such as well the method for its determination are known to the one skilled in the art.

Preferably, the $K_D$ value shown by the nucleic acids according to the present invention is below 1 μM. A $K_D$ value of about 1 μM is said to be characteristic for a non-specific binding of a nucleic acid to a target. As will be acknowledged by the ones skilled in the art, the $K_D$ value of a group of compounds such as the nucleic acids according to the present invention is within a certain range. The above-mentioned $K_D$ of about 1 μM is a preferred upper limit for the $K_D$ value. The lower limit for the $K_D$ of target binding nucleic acids can be as little as about 10 picomolar or can be higher. It is within the present invention that the $K_D$ values of individual nucleic acids binding to SDF-1 is preferably within this range. Preferred ranges can be defined by choosing any first number within this range and any second number within this range. Preferred upper $K_D$ values are 250 nM and 100 nM, preferred lower $K_D$ values are 50 nM, 10 nM, 1 nM, 100 pM and 10 pM. The more preferred upper $K_D$ value is 2.5 nM, the more preferred lower $K_D$ value is 100 pM.

In addition to the binding properties of the nucleic acid molecules according to the present invention, the nucleic acid molecules according to the present invention inhibit the function of the respective target molecule which is in the present case SDF-1. The inhibition of the function of SDF-1—for instance the stimulation of the respective receptors as described previously—is achieved by binding of nucleic acid molecules according to the present invention to SDF-1 and forming a complex of a nucleic acid molecule according to the present invention and SDF-1. Such complex of a nucleic acid molecule and SDF-1 cannot stimulate the receptors that normally are stimulated by SDF-1. Accordingly, the inhibition of receptor function by nucleic acid molecules according to the present invention is independent from the respective receptor that can be stimulated by SDF-1 but results from preventing the stimulation of the receptor by SDF-1 by the nucleic acid molecules according to the present invention.

A possibility to determine the inhibitory constant of the nucleic acid molecules according to the present invention is the use of the methods as described in Examples 5 and 6 (for CXCR4 and CXCR7, respectively) which confirms the above finding that the nucleic acids according to the present invention exhibit a favourable inhibitory constant which allows the use of said nucleic acids in a therapeutic treatment scheme. An appropriate measure in order to express the intensity of the inhibitory effect of the individual nucleic acid molecule on interaction of the target which is in the present case SDF-1 and the respective receptor, is the so-called half maximal inhibitory concentration (abbr. $IC_{50}$) which as such as well the method for its determination are known to the one skilled in the art.

Preferably, the $IC_{50}$ value shown by the nucleic acid molecules according to the present invention is below 1 μM. An $IC_{50}$ value of about 1 μM is said to be characteristic for a non-specific inhibition of target functions by a nucleic acid molecule. As will be acknowledged by the ones skilled in the art, the $IC_{50}$ value of a group of compounds such as the nucleic acid molecules according to the present invention is within a certain range. The above-mentioned $IC_{50}$ of about 1 μM is a preferred upper limit for the $IC_{50}$ value. The lower limit for the $IC_{50}$ of target binding nucleic acid molecules can be as little as about 10 picomolar or can be higher. It is within the present invention that the $IC_{50}$ values of individual nucleic acids binding to SDF-1 is preferably within this range. Preferred ranges can be defined by choosing any first number within this range and any second number within this range. Preferred upper $IC_{50}$ values are 250 nM and 100 nM, preferred lower $IC_{50}$ values are 50 nM, 10 nM, 1 nM, 100 pM and 10 pM. The more preferred upper $IC_{50}$ value is 2.5 nM, the more preferred lower $IC_{50}$ value is 100 pM.

The nucleic acid molecules according to the present invention may have any length provided that they are still able to bind to the target molecule. It will be acknowledged in the art that there are preferred lengths of the nucleic acids according to the present inventions. Typically, the length is between 15 and 120 nucleotides. It will be acknowledged by the ones skilled in the art that any integer between 15 and 120 is a possible length for the nucleic acids according to the present invention. More preferred ranges for the length of the nucleic acids according to the present invention are lengths of about 20 to 100 nucleotides, about 20 to 80 nucleotides, about 20 to 60 nucleotides, about 20 to 50 nucleotides and about 29 to 45 nucleotides.

It is within the present invention that the nucleic acids disclosed herein comprise a moiety which preferably is a high molecular weight moiety and/or which preferably allows to modify the characteristics of the nucleic acid in terms of, among others, residence time in the animal body, preferably the human body. A particularly preferred embodiment of such modification is PEGylation and HESylation of the nucleic acids according to the present invention. As used herein PEG stands for poly(ethylene glycole) and HES for hydroxyethly starch. PEGylation as preferably used herein is the modification of a nucleic acid according to the present invention whereby such modification consists of a PEG moiety which is attached to a nucleic acid according to the present invention. HESylation as preferably used herein is the modification of a nucleic acid according to the present invention whereby such modification consists of a HES moiety which is attached to a nucleic acid according to the present invention. These modifications as well as the process of modifying a nucleic acid using such modifications, is described in European patent application EP 1 306 382, the disclosure of which is herewith incorporated in its entirety by reference.

In case of PEG being such high molecular weight moiety the molecular weight is preferably from about 20,000 to about 120,000 Da, more preferably from about 30,000 to about 80,000 Da and most preferably about 40,000 Da. In case of HES being such high molecular weight moiety the molecular weight is preferably from about 50 to about 1000 kDa, more preferably from about 100 to about 700 kDa and most preferably from about 200 to about 500 kDa. HES exhibits a molar substitution of 0.1 to 1.5, more preferably of 1 to 1.5 and exhibits a substitution sample expressed as the C2/C6 ratio of approximately 0.1 to 15, preferably of approximately 3 to 10. The process of HES modification is, e.g., described in German patent application DE 1 2004 006 249.8 the disclosure of which is herewith incorporated in its entirety by reference.

The modification can, in principle, be made to the nucleic acid molecules of the present invention at any position thereof. Preferably such modification is made either to the 5'-terminal nucleotide, the 3'-terminal nucleotide and/or any nucleotide between the 5' nucleotide and the 3' nucleotide of the nucleic acid molecule.

The modification and preferably the PEG and/or HES moiety can be attached to the nucleic acid molecule of the present invention either directly or indirectly, preferably through a linker. It is also within the present invention that the nucleic acid molecule according to the present invention comprises one or more modifications, preferably one or more PEG and/or HES moiety. In an embodiment the individual linker molecule attaches more than one PEG moiety or HES moiety to a nucleic acid molecule according to the present invention. The linker used in connection with the present invention can itself be either linear or branched. This kind of linkers are known to the ones skilled in the art and are further described in patent applications WO2005/074993 and WO2003/035665.

In a preferred embodiment the linker is a biodegradable linker. The biodegradable linker allows to modify the characteristics of the nucleic acid according to the present invention in terms of, among other, residence time in an animal body, preferably in a human body, due to release of the modification from the nucleic acid according to the present invention. Usage of a biodegradable linker may allow a better control of the residence time of the nucleic acid according to the present invention. A preferred embodiment of such biodegradable linker is a biodegradable linker as described in, but not limited to, international patent applications WO2006/052790, WO2008/034122, WO2004/092191 and WO2005/099768.

It is within the present invention that the modification or modification group is a biodegradable modification, whereby the biodegradable modification can be attached to the nucleic acid molecule of the present invention either directly or indirectly, preferably through a linker. The biodegradable modification allows to modify the characteristics of the nucleic acid according to the present invention in terms of, among other, residence time in an animal body, preferably in a human body, due to release or degradation of the modification from the nucleic acid according to the present invention. Usage of biodegradable modification may allow a better control of the residence time of the nucleic acid according to the present invention. A preferred embodiment of such biodegradable modification is biodegradable as described in, but not restricted to, international patent applications WO2002/065963, WO2003/070823, WO2004/113394 and WO2000/41647, preferably in WO2000/41647, page 18, line 4 to 24.

Beside the modifications as described above, other modifications can be used to modify the characteristics of the nucleic acids according to the present invention, whereby such other modifications may be selected from the group of proteins, lipids such as cholesterol and sugar chains such as amylase, dextran etc.

Without wishing to be bound by any theory, it seems that by modifying the nucleic acids according to the present invention with high molecular weight moiety such as a polymer and more particularly one or several of the polymers disclosed herein, which are preferably physiologically acceptable, the excretion kinetic is changed. More particularly, it seems that due to the increased molecular weight of such modified inventive nucleic acids and due to the nucleic acids of the invention not being subject to metabolism particularly when in the L-form, excretion from an animal body, preferably from a mammalian body and more preferably from a human body is decreased. As excretion typically occurs via the kidneys, the present inventors have found that the glomerular filtration rate of the thus modified nucleic acids is significantly reduced compared to the nucleic acids not having this kind of high molecular weight modification which results in an increase in the residence time in the animal body. In connection therewith it is particularly noteworthy that, despite such high molecular weight modification the specificity of the nucleic acids according to the present invention is not affected in a detrimental manner. Insofar, the nucleic acids according to the present invention have among others, the surprising characteristic—which normally cannot be expected from pharmaceutically active compounds—such that a pharmaceutical formulation providing for a sustained release is not necessarily required to provide for a sustained release of the nucleic acids according to the present invention. Rather, the nucleic acids according to the present invention in their modified form comprising a high molecular weight moiety, can as such already be used as a sustained release-formulation as they act, due to their modification, already as if they were released from a sustained-release formulation. Insofar, the modification(s) of the nucleic acid molecules according to the present invention as disclosed herein and the thus modified nucleic acid molecules according to the present invention and any composition comprising the same may provide for a distinct, preferably controlled pharmacokinetics and biodistribution thereof. This also includes residence time in circulation and distribution to tissues. Such modifications are further described in the patent application WO2003/035665.

However, it is also within the present invention that the nucleic acids according to the present invention do not comprise any modification and particularly no high molecular weight modification such as PEGylation or HESylation. Such embodiment is particularly preferred when the nucleic acid according to the present invention shows preferential distribution to any target organ or tissue in the body or when a fast clearance of the nucleic acid according to the present invention from the body after administration is desired. Nucleic acids according to the present invention as disclosed herein with a preferential distribution profile to any target organ or tissue in the body would allow establishment of effective local concentrations in the target tissue while keeping systemic concentration of the nucleic acids low. This would allow the use of low doses which is not only beneficial from an economic point of view, but also reduces unnecessary exposure of other tissues to the nucleic acid agent, thus reducing the potential risk of side effects. Fast clearance of the nucleic acids according to the present invention from the body after administration might be desired, among others, in case of in vivo imaging or specific therapeutic dosing requirements using the nucleic acids according to the present invention or medicaments comprising the same.

The nucleic acids according to the present invention, and/or the antagonists according to the present invention may be used for the generation or manufacture of a medicament. Such medicament or a pharmaceutical composition according to the present invention contains at least one of the inventive nucleic acids selected from the group of SDF-1 binding nucleic acids, optionally together with one or more further pharmaceutically active compounds, whereby the inventive nucleic acid preferably acts as pharmaceutically active compound itself. Such medicaments comprise in preferred embodiments at least a pharmaceutically acceptable carrier. Such carrier may be, e.g., water, buffer, PBS, glucose solution, preferably a 5% glucose salt balanced solution, starch, sugar, gelatine or any other acceptable carrier substance. Such carriers are generally known to the one skilled in the art. It will be acknowledged by the person skilled in the art that any embodiments, use and aspects of or related to the medicament of the present invention is also applicable to the pharmaceutical composition of the present invention and vice versa.

The indications, diseases and disorders for the treatment and/or prevention of which the nucleic acids, the pharmaceutical compositions and medicaments are used in accordance with or prepared in accordance with the present invention result from the involvement, either direct or indirect, of SDF-1 in the respective pathogenic mechanism.

Of course, because the SDF-1 binding nucleic acids according to the present invention interact with or bind to human or murine SDF-1, a skilled person will generally understand that the SDF-1 binding nucleic acids according to the present invention can be easily used for the treatment, prevention and/or diagnosis of any disease of humans and animals as described herein. In connection therewith, it is to be acknowledged that the nucleic acid molecules according to the present invention can be used for the treatment and prevention of any of the diseases, disorder or condition described herein, irrespective of the mode of action underlying such disease, disorder and condition.

In the following the rational for the use of the nucleic acid molecules according to the present invention in connection with the various diseases, disorders and conditions is provided, thus rendering the claimed therapeutic, preventive and diagnostic applicability of the nucleic acid molecules according to the present invention plausible. In order to avoid any unnecessary repetition, it should be acknowledged that due to the involvement of the SDF-1—SDF-1 receptor axis as outlined in connection therewith said axis may be addressed by the nucleic acid molecules according to the present invention such that the claimed therapeutic, preventive and diagnostic effect is achieved. It should furthermore be acknowledged that the particularities of the diseases, disorders and conditions, of the patients and any detail of the treatment regimen described in connection therewith, may be subject to preferred embodiments of the instant application.

For haematological malignancies, in particular, there is considerable evidence that leukemia cells may be protected from conventional therapies (such as chemotherapy combined with various targeted agents such as specific antibodies or kinase inhibitors) within particular tissue microenvironments, referred to as niches. Such niches are found particularly in the bone marrow where they can harbour malignant cells that are then able to expand and produce a relapse following the initial therapy (Burger and Kipps, 2002; Burger and Burkle, 2007; Meads et al., 2008; Burger, Ghia et al., 2009). This preservation of malignant cells during chemotherapy is thought to be largely due to direct contact between the malignant cells and stromal cells (Lagneaux, Delforge et al. 1998; Kurtova, Balakrishnan et al., 2009; Damiano, Cress et al., 1999). However in the complexity of this microenvironment there are multiple cellular and molecular signals that may lead to resistance of the malignant cells to chemotherapy. Despite this complexity it is clear that stromal cells produce the chemokine SDF-1 and that both normal and malignant cells that express CXCR4 migrate to and are held in such niches. That this molecular pathway is key for this interaction is demonstrated by the fact that specific inhibition of this interaction is sufficient to release both normal and malignant cells from the niches (Broxmeyer, Orschell et al., 2005; Devine, Flomenberg et al., 2004; Azab, Runnels et al., 2009). In addition to weakening the interaction with the niches it has been shown for numerous hematological malignancies that disruption of the SDF-1-CXCR4 axis results in increasing the vulnerability of the cells to other therapies—so called 'chemosensitization'. This chemosensitization has been described, among others, for multiple myeloma (Azab, Runnels et al., 2009) and various acute and chronic leukemias (Dillmann, Veldwijk et al., 2009; Lagneaux, Delforge et al. 1998).

Therefore, using SDF-1 binding nucleic acids according to the present invention to disrupt cross talk between malignant cells and their milieu to sensitize them to other therapies is an attractive and convincing strategy for the treatment of haematological malignacies. Examples of therapies that can be enhanced by combination with SDF-1 binding nucleic acids according to the present invention include, but are not limited to Fludarabine, Cyclophosphamide, Rituxan, Chlorambucil, Lenalidomide, Bortezomib, Dexamethasone, Melphalan, Imatinib and Nilotinib.

The foregoing description emphasizes the role of bone marrow stromal cells and bone marrow niches in the protection of malignant cells from the effects of chemotherapy or other targeted therapies for haematological malignancies. However, there is evidence for similar interactions occurring locally within solid tumors as a large proportion of the cells in solid tumors are not cancer cells, but stromal, immune or vascular cells derived from the host that interact intimately with the tumor cells. Many different types of solid tumors express CXCR4 (Engl, Relja et al., 2006; Müller, Homey et al., 2001; Koshiba, Hosotani et al., 2000, Ehtesham, Stevenson, et al., 2008; Zeelenberg, Ruuls-Van Stalle et al., 2003; Sauer, Seidler et al., 2005; Su, Zhang et al., 2005) and/or CXCR7 (Burns, Summers et al. 2006; Miao et al., 2007; Wang et al., 2008; Zheng, Li et al., 2010) receptors either constitutively or in response to hypoxia or various treatments. Malignant cells may use this signaling pathway for survival and migration by activation of Akt and Erk. SDF-1 can be produced by the malignant cells themselves or by the stromal cells within the tumor. Once again in this complex environment the exact mechanism by which tumour cells grow and escape from chemotherapy or other therapeutic approaches are not clearly defined. However it is clear that the SDF-1-CXCR4 axis and the SDF-1-CXCR7 play an important role. For example, inhibition of CXCR4 sensitizes glioma cell lines to in vitro chemotherapy (Redjal et al., 2006) and high expression of CXCR4 is predictive of poor outcome in breast cancer (Holm, Abreo et al., 2008;

Mizell, Smith et al., 2009) and gastro-intestinal cancers (Schimanski et al., 2008). Therefore, the use of SDF-1 binding nucleic acids according to the present invention to inhibit the action of SDF-1 on either CXCR4 or CXCR7 receptors in a wide variety of solid tumors will enhance current therapy by making the cells more vulnerable to the therapy either by direct action or by blocking interactions with other cells in the tumor.

In addition to the above aspects, CXCR4 also conveys signals that are thought to be critical for recruitment and retention of pro-angiogenic and immunosuppressive bone marrow-derived cells (BMDCs). This pathway may therefore also be used for VEGF-independent angiogenesis. As a consequence, blocking the SDF1-CXCR4 axis to sensitize tumors to anti-VEGF therapy or radiation has emerged as an attractive and convincing strategy treatment for solid cancers.

However, there is concern that CXCR4 blockade may not be sufficient to block the effects of SDF-1, which may also bind to CXCR7 on cancer or stromal cells. For example, CXCR7 has been recently reported to be expressed in brain tumor cells and mediate anti-apoptotic effects, and has also been shown to regulate the invasion, angiogenesis and tumor growth of human hepatocellular carcinomas. In such cases, the action of SDF-1 binding nucleic acids to block the action of SDF-1 on both the CXCR7 and CXCR4 receptors in a single agent would provide particular and unseen efficacy compared to specific receptor blockers.

The medicament according to the present invention may be used in combination with a further medicament or a further pharmaceutically active agent, whereby the further medicament or the further pharmaceutically active agent damages, destroys and/or labels (the) cancer cells. If the nucleic acid molecule according to the present invention is used with a further medicament or a further pharmaceutically active agent, the therapy which is based on the nucleic acid molecule, is preferably an adjunct therapy to the therapy making use of or being based on the further medicament or further pharmaceutically active agent. Such further medicament or further pharmaceutically active agent is preferably selected from but not restricted to the group comprising

- a) antibodies such as Rituximab (target: CD20), Cetuximab (target: epidermal growth factor receptor), Ibritumomab-Tiuxetan (target: CD20), Tositumomab (target: CD20), Trastuzumab (target: HER2/neu), Bevacizumab (target: VEGF), Alemtuzumab (target: CD52);
- b) alkylating agents such as cisplatin, carboplatin, oxaliplatin, mechlorethamine, cyclophosphamide, chlorambucil, Doxorubicin, liposomal Doxorubicin, bendamustine, Melphalan, temozolomide;
- c) anti-metabolites such as purineazathioprine, mercaptopurine, fludarabine, pentostatin, cladribine;
- d) plant alkaloids such vinca alkaloids, plant terpenoids such as taxanes, preferably Docetaxel, Paclitaxel, podophyllotoxin, epothilone;
- e) topoisomerase inhibitors such as camptothecins, irinitecan, mitoxantrone; and
- f) and other agents such as Leucovorin, Methotrexate, Tamoxifen, Sorafenib, Lenalidomide, Bortezomib, Dexamethasone, Flurouracil and Prendnisone.

Other agents that can be used as further pharmaceutically active agent in the treatment of cancer are well known in the art and include, but are not limited to immunsuppressive drugs, cytokines and cytostatic drugs (for reference: "Allgemeine und Spezielle Pharmakologie und Toxikologie 2011", editor: Thomas Karow; Pulheim, Germany). Such agents well known in the art are used in the treatment of cancer according to the current standard of care for the particular cancer patient population.

It will be acknowledged that the above specified further pharmaceutically active agents can be used in connection with each any any aspect of the present invention which makes use of such further pharmaceutically active agent, including the medicament of the present invention and the pharmaceutical composition of the present invention.

The further medicament or pharmaceutically active agent has or may provide the function of a chemotherapy. Alternatively or additionally to chemotherapy, radiotherapy can be used.

The medicament according to the present invention, in combination with or without the further medicament or further pharmaceutically active agent, and with or without radiotherapy, can be used for the treatment and/or prevention of cancer, preferably

- a) hematological cancer, whereby more preferably the hematological cancer is selected from the group of leukemia and myeloma; and
- b) a solid tumor, whereby more preferably the solid tumor is selected from the group of glioblastoma, colorectal cancer, breast cancer, lymphoma, prostate cancer, pancreatic cancer, lung cancer, renal cancer and ovarian cancer.

Preferably, breast cancer is selected from the group of advanced HER2-negative breast cancer.

Preferably, leukemia is selected from the group of chronic lymphoid leukemia and acute myeloid leukemia.

Preferably, myeloma is selected from the group of multiple myeloma.

The preferred further medicament or the further pharmaceutically active agent for the treatment of Glioblastoma is radiotherapy or chemotherapy with temozolomide or therapy with bevacizumab. The preferred further medicament or the further pharmaceutically active agent for the treatment of colorectal cancer is selected from the group comprising fluorouracil Leucovorin, Oxaliplatin, Irinotecan and bevacizumab.

The preferred further medicament or the further pharmaceutically active agent for the treatment of advanced HER2-negative breast cancer is selected from the group of Doxorubicin, Paclitaxel, Docetaxel, Methotrexate, Fluorouracil, Bevacizumab, Tamoxifen, and aromatase inhibitors.

The preferred further medicament or the further pharmaceutically active agent for the treatment of chronic lymphoid leukemia is selected from the group comprising fludarabine, cyclophosphamide, rituximab, Chlorambucil, alemtuzumab, vincristine, pentostatin, mitoxantrone, doxorubicin, cladribine, and bendamustine.

The preferred further medicament or the further pharmaceutically active agent for the treatment of multiple myeloma is selected from the group comprising Lenalidomide, Bortezomib, Dexamethasone, Melphalan, Cyclophosphamide, liposomal doxorubicin, and prednisone.

In one embodiment of the medicament of the present invention, such medicament is for use in combination with other treatments for any of the diseases disclosed herein, particularly those for which the medicament of the present invention is to be used.

"Combination therapy" (or "co-therapy") includes the administration of a medicament of the invention and at least a second or further agent as part of a specific treatment regimen intended to provide the beneficial effect from the co-action of these therapeutic agents, i. e. the medicament of the present invention and said second or further agent. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may be, but generally is not, intended to encompass the administration of two or more of these therapeutic agents as part of separate monotherapy regimens. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" can also embrace the administration of the therapeutic agents as described above in further combination with other biologically active ingredients. Where the combination therapy further comprises a non-drug treatment, the non-drug treatment may be conducted at any suitable time as long as a beneficial effect from the co-action of the combination of the therapeutic agents and non-drug treatment is achieved. For example, in appropriate cases, the beneficial effect is still achieved when the non-drug treatment is temporally removed or separated from the administration of the therapeutic agent(s), perhaps by days or even weeks. As outlined in general terms above, the medicament according to the present invention can be administered, in principle, in any form known to the ones skilled in the art. A preferred route of administration is systemic administration, more preferably by parenteral administration, preferably by injection. Alternatively, the medicament may be administered locally. Other routes of administration comprise intramuscular, intraperitoneal, and subcutaneous, per orum, intranasal, intratracheal or pulmonary with preference given to the route of administration that is the least invasive, while ensuring efficiency. The same equally applies to the pharmaceutical composition of the present invention.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained, that are well known to the ordinary skill in the art.

Furthermore, preferred medicaments of the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels.

Subjects that will respond favorably to the method of the invention include medical and veterinary subjects generally, including human beings and human patients. Among other subjects for whom the methods and means of the invention are useful are cats, dogs, large animals, avians such as chickens, and the like.

The medicament of the present invention will generally comprise an effective amount of the active component(s) of the therapy, including, but not limited to, a nucleic acid molecule of the present invention, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the medicament of the present invention.

In a further aspect the present invention is related to a pharmaceutical composition. Such pharmaceutical composition comprises at least one of the nucleic acids according to the present invention and preferably a pharmaceutically acceptable binder. Such binder can be any binder used and/or known in the art. More particularly such binder is any binder as discussed in connection with the manufacture of the medicament disclosed herein. In a further embodiment, the pharmaceutical composition comprises a further pharmaceutically active agent.

The preparation of a medicament and a pharmaceutical composition is known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, a medicament will be administered in a manner compatible with the dosage formulation, and in such amount as is pharmacologically effective. The formulations are easily administered in a variety of dosage forms, such as the type of injectable solutions described above, but drug release capsules and the like can also be employed.

The medicament of the invention can also be administered in oral dosage forms as time release and sustained release tablets or capsules, pills, powders, granules, elixirs, tinctures, suspensions, syrups and emulsions. Suppositories are advantageously prepared from fatty emulsions or suspensions.

The pharmaceutical composition or medicament may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The medicaments and nucleic acid molecules, respectively, of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to form a lipid layer encapsulating the drug, what is well known to the ordinary skill in the art. For example, the nucleic acid molecules described herein can be provided as a complex with a lipophilic compound or non-immunogenic, high molecular weight compound constructed using methods known in the art. Additionally, liposomes may bear such nucleic acid molecules on their surface for targeting and carrying cytotoxic agents internally to mediate cell killing. An example of nucleic-acid associated complexes is provided in U.S. Pat. No. 6,011,020.

The medicaments and nucleic acid molecules, respectively, of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the medicaments and nucleic acid molecules, respectively, of the present invention may be coupled to a class of biodegradable polymers useful in achieving controlled release of a drug, for example, polylactic acid, polyepsilon capro lactone, polyhydroxy butyric acid, polyorthoesters, polyacetals, polydihydropyrans, polycyanoacrylates and cross-linked or amphipathic block copolymers of hydrogels.

If desired, the pharmaceutical composition and medicament, respectively, to be administered may also contain minor amounts of non-toxic auxiliary substances such as wetting or emulsifying agents, pH buffering agents, and other substances such as for example, sodium acetate, and triethanolamine oleate.

The dosage regimen utilizing the nucleic acid molecules and medicaments, respectively, of the present invention is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

Effective plasma levels of the nucleic acid according to the present invention preferably range from 500 fM to 200 μM, preferably from 1 nM to 20 μM, more preferably from 5 nM to 20 μM, most preferably 50 nM to 20 μM in the treatment of any of the diseases disclosed herein.

The nucleic acid molecules and medicaments, respectively, of the present invention may preferably be administered in a single daily dose, every second or third day, weekly, every second week, in a single monthly dose or every third month.

It is within the present invention that the medicament as described herein constitutes the pharmaceutical composition disclosed herein.

In a further aspect the present invention is related to a method for the treatment of a subject who is in need of such treatment, whereby the method comprises the administration of a pharmaceutically active amount of at least one of the nucleic acids according to the present invention. In an embodiment, the subject suffers from a disease or is at risk to develop such disease, whereby the disease is any of those, disclosed herein, particularly any of those diseases disclosed in connection with the use of any of the nucleic acids according to the present invention for the manufacture of a medicament.

Immunotherapy is a form of cancer treatment that uses a patient's own immune system to destroy cancer cells. The rational behind immunotherapy is to harness or further enhance the power of body's own immune system to fight tumor cells. There are different immunotherapy approaches, including:

- cellular therapies involving an approach where a patient's own T-cells are transformed to produce chimeric antigen receptors ("Chimeric antigen receptor T cell (CAR-T) approach"),
- NK cell therapy using expanded autologous or allogeneic NK cells
- immune checkpoint inhibitors,
- immunomodulators,
- T-cell and NK-cell engagers, (e.g. bispecific antibodies) and
- cancer vaccines.

An important part of the immune system is its ability to tell or distinguish between normal cells in the body and those it sees as "foreign." This lets the immune system attack the foreign cells while leaving the normal cells alone. To do this, it uses "checkpoints"—molecules on certain immune cells that need to be activated (or inactivated) to start an immune response. Cancer cells sometimes find ways to use these checkpoints to avoid being attacked by the immune system. But drugs that target these checkpoints hold a lot of promise as cancer treatments.

PD-1 is a checkpoint protein on immune cells called T cells. It normally acts as a type of "off switch" that helps preventing T cells from attacking other cells in the body. It does this when it attaches to PD-L1, a protein on some normal (and cancer) cells. When PD-1 binds to PD-L1, it basically tells the T cell to leave the other cell alone. Some cancer cells have large amounts of PD-L1, which helps them evading immune attack. Monoclonal antibody treatment that targets either PD-1 or PD-L1 can boost the immune response against cancer cells and have shown a great deal of promise in treating certain cancers. Examples of treatments that target PD-1 include, for example, Pembrolizumab (Keytruda®) and Nivolumab (Opdivo®)

CTLA-4 is another protein on some T cells that acts as a type of "off switch" to keep the immune system in check. Ipilimumab (Yervoy®) is a monoclonal antibody that attaches to CTLA-4 and stops it from working. This can boost the body's immune response against cancer cells.

A cancer vaccine is a vaccine that either treats existing cancer or prevents development of a cancer. Vaccines that treat existing cancer are also known as therapeutic cancer vaccines.

As preferably used herein, the term treatment comprises in a preferred embodiment additionally or alternatively prevention and/or follow-up.

As preferably used herein, the terms disease and disorder shall be used in an interchangeable manner, if not indicated to the contrary.

As preferably used herein, the terms SDF-1 and CXCL12 shall be used in an interchangeable manner, if not indicated to the contrary.

In an embodiment of the various aspects embodiments of the present invention the term modulating the number of cells and more specifically modulating the number of tumor-infiltrating leukocytes preferably means that the number of such cells and leukocytes, respectively, is increased or decreased.

In an embodiment of the present invention the term modulating the spatial distribution of cells and more specifically modulating the spatial distribution of tumor-infiltrating leukocytes, preferably means that the spatial distribution of such cells and leukocytes, respectively, is changed in a way which is beneficial and/or provides the prerequisites, preferably at the molecular and/or cellular level, for the success and/or efficacy of a therapeutic treatment, preferable a therapeutic treatment of a tumor and/or metastases.

As used herein, the term comprise is preferably not intended to limit the subject matter followed or described by such term. However, in an alternative embodiment the term comprises shall be understood in the meaning of containing and thus as limiting the subject matter followed or described by such term.

The various SEQ ID NOs: the chemical nature of the nucleic acid molecules according to the present invention and the target molecules SDF-1 as used herein, the actual sequence thereof and the internal reference number is summarized in the following table. It has to be noticed that the nucleic acids were characterized on the aptamer, i. e. D-nucleic acid level (D-RNA) with the biotinylated human D-SDF-1 (SEQ ID NO: 4) or on the Spiegelmer level, i. e. L-nucleic acid (L-RNA) with the natural configuration of SDF-1, the L-SDF-1 (human SDF-1α, SEQ ID NO: 1). The different nucleic acids share one internal reference name but one SEQ ID Nos: for the D-RNA (Aptamer) molecule and one SEQ ID Nos for the L-RNA (Spiegelmer) molecule, respectively.

TABLE 1

| SEQ ID NO: | RNA/Peptide | Sequence | Internal Reference |
|---|---|---|---|
| 1 | L-peptide | KPVSLSYRCPCRFFESHVARANVKHLKILNTPNCALQIVARLKNNNR QVCIDPKLKWIQEYLEKALNK | human/monkey/cat SDF-1α<br>human/monkey/cat SDF-1 |
| 2 | L-peptide | KPVSLSYRCPCRFFESHVARANVKHLKILNTPNCALQIVARLKNNNR QVCIDPKLKWIQEYLEKALNKRFKM | human/monkey/cat SDF-1β |
| 3 | L-peptide | KPVSLSYRCPCRFFESHIARANVKHLKILNTPNCALQIVARLKNNNR QVCIDPKLKWIQEYLEKALNK | murine SDF-1α<br>murine SDF-1 |
| 4 | D-peptide | KPVSLSYRCPCRFFESHVARANVKHLKILNTPNCALQIVARLKNNNR QVCIDPKLKWIQEYLEKALNKRFK-Biotin | biotinylated hu D-SDF-1 |
| 5 | L-RNA | AGCGUGGUGUGAUCUAGAUGUAGUGGCUGAUCCUAGUCAGGUACGCU | 193-C2-001 |
| 6 | L-RNA | AGCGUGGUGUGAUCUAGAUGUAUUGGCUGAUCCUAGUCAGGUACGCU | 193-G2-001 |
| 7 | L-RNA | AGCGUGGUGUGAUCUAGAUGUAAUGGCUGAUCCUAGUCAGGUGCGCU | 193-F2-001 |
| 8 | L-RNA | GCGAGGUGUGAUCUAGAUGUAGUGGCUGAUCCUAGUCAGGUGCGC | 193-G1-002 |
| 9 | L-RNA | GCGUGGUGUGAUCUAGAUGUAGUGGCUGAUCCUAGUCAGGUGCGC | 193-D2-002 |
| 10 | L-RNA | GCAUGGUGUGAUCUAGAUGUAGUGGCUGAUCCUAGUCAGGUGCCC | 193-A1-002 |
| 11 | L-RNA | GCGUGGUGUGAUCUAGAUGUAAUGGCUGAUCCUAGUCAGGGACGC | 193-D3-002 |
| 12 | L-RNA | GCGUGGUGUGAUCUAGAUGUAGAGGCUGAUCCUAGUCAGGUACGC | 193-B3-002 |
| 13 | L-RNA | GCGUGGUGUGAUCUAGAUGUAAAGGCUGAUCCUAGUCAGGUACGC | 193-H3-002 |
| 14 | L-RNA | GUGGUGUGAUCUAGAUGUAGUGGCUGUUCCUAGUCAGGUAUGC | 193-E3-002 |
| 15 | L-RNA | GCGUGGUGUGAUCUAGAUGUAGUGGCUGAUCCUAGUUAGGUACGC | 193-D1-002 |
| 16 | L-RNA | GCGUGGUGUGAUCUAGAUGUAGUGGCUGAUCCUAGUCAGGUACGC | 193-C2-002 |
| 17 | L-RNA | CGUGGUGUGAUCUAGAUGUAGUGGCUGAUCCUAGUCAGGUACG | 193-C2-003 |
| 18 | L-RNA | GUGGUGUGAUCUAGAUGUAGUGGCUGAUCCUAGUCAGGUAC | 193-C2-004 |
| 19 | L-RNA | UGGUGUGAUCUAGAUGUAGUGGCUGAUCCUAGUCAGGUA | 193-C2-005 |
| 20 | L-RNA | GGUGUGAUCUAGAUGUAGUGGCUGAUCCUAGUCAGGU | 193-C2-006 |
| 21 | L-RNA | GUGUGAUCUAGAUGUAGUGGCUGAUCCUAGUCAGG | 193-C2-007 |

TABLE 1-continued

| SEQ ID NO: | RNA/Peptide | Sequence | Internal Reference |
|---|---|---|---|
| 22 | L-RNA | GCGUGGUGUGAUCUAGAUGUAUUGGCUGAUCCUAGUCAGGUACGC | 193-G2-012 |
| 23 | L-RNA | GCGCGGUGUGAUCUAGAUGUAUUGGCUGAUCCUAGUCAGGCGCGC | 193-G2-013 |
| 24 | L-RNA | GCGCGUGUGAUCUAGAUGUAUUGGCUGAUCCUAGUCAGGGCGC | 193-G2-014 |
| 25 | L-RNA | GGGCGUGUGAUCUAGAUGUAUUGGCUGAUCCUAGUCAGGGCCC | 193-G2-015 |
| 26 | L-RNA | GGCCGUGUGAUCUAGAUGUAUUGGCUGAUCCUAGUCAGGGGCC | 193-G2-016 |
| 27 | L-RNA | GCCCGUGUGAUCUAGAUGUAUUGGCUGAUCCUAGUCAGGGGGC | 193-G2-017 |
| 28 | L-RNA | 5'-40 kDa-PEG-<br>GCGUGGUGUGAUCUAGAUGUAUUGGCUGAUCCUAGUCAGGUACGC | 193-G2-012-5'-PEG,<br>NOX-A12 |
| 29 | D-RNA | AGCGUGGUGUGAUCUAGAUGUAGUGGCUGAUCCUAGUCAGGUACGCU | 193-C2-001 |
| 30 | D-RNA | AGCGUGGUGUGAUCUAGAUGUAUUGGCUGAUCCUAGUCAGGUACGCU | 193-G2-001 |
| 31 | D-RNA | AGCGUGGUGUGAUCUAGAUGUAAUGGCUGAUCCUAGUCAGGUGCGCU | 193-F2-001 |
| 32 | D-RNA | GCGAGGUGUGAUCUAGAUGUAGUGGCUGAUCCUAGUCAGGUGCGC | 193-G1-002 |
| 33 | D-RNA | GCGUGGUGUGAUCUAGAUGUAGUGGCUGAUCCUAGUCAGGUGCGC | 193-D2-002 |
| 34 | D-RNA | GCAUGGUGUGAUCUAGAUGUAGUGGCUGAUCCUAGUCAGGUGCCC | 193-A1-002 |
| 35 | D-RNA | GCGUGGUGUGAUCUAGAUGUAAUGGCUGAUCCUAGUCAGGGACGC | 193-D3-002 |
| 36 | D-RNA | GCGUGGUGUGAUCUAGAUGUAGAGGCUGAUCCUAGUCAGGUACGC | 193-B3-002 |
| 37 | D-RNA | GCGUGGUGUGAUCUAGAUGUAAAGGCUGAUCCUAGUCAGGUACGC | 193-H3-002 |
| 38 | D-RNA | GUGGUGUGAUCUAGAUGUAGUGGCUGUUCCUAGUCAGGUAUGC | 193-E3-002 |
| 39 | D-RNA | GCGUGGUGUGAUCUAGAUGUAGUGGCUGAUCCUAGUUAGGUACGC | 193-D1-002 |
| 40 | D-RNA | GCGUGGUGUGAUCUAGAUGUAGUGGCUGAUCCUAGUCAGGUACGC | 193-C2-002 |
| 41 | D-RNA | CGUGGUGUGAUCUAGAUGUAGUGGCUGAUCCUAGUCAGGUACG | 193-C2-003 |
| 42 | D-RNA | GUGGUGUGAUCUAGAUGUAGUGGCUGAUCCUAGUCAGGUAC | 193-C2-004 |
| 43 | D-RNA | UGGUGUGAUCUAGAUGUAGUGGCUGAUCCUAGUCAGGUA | 193-C2-005 |
| 44 | D-RNA | GGUGUGAUCUAGAUGUAGUGGCUGAUCCUAGUCAGGU | 193-C2-006 |
| 45 | D-RNA | GUGUGAUCUAGAUGUAGUGGCUGAUCCUAGUCAGG | 193-C2-007 |
| 46 | D-RNA | GCGUGGUGUGAUCUAGAUGUAUUGGCUGAUCCUAGUCAGGUACGC | 193-G2-012 |
| 47 | D-RNA | GCGCGGUGUGAUCUAGAUGUAUUGGCUGAUCCUAGUCAGGCGCGC | 193-G2-013 |
| 48 | D-RNA | GCGCGUGUGAUCUAGAUGUAUUGGCUGAUCCUAGUCAGGGCGC | 193-G2-014 |
| 49 | D-RNA | GGGCGUGUGAUCUAGAUGUAUUGGCUGAUCCUAGUCAGGGCCC | 193-G2-015 |
| 50 | D-RNA | GGCCGUGUGAUCUAGAUGUAUUGGCUGAUCCUAGUCAGGGGCC | 193-G2-016 |
| 51 | D-RNA | GCCCGUGUGAUCUAGAUGUAUUGGCUGAUCCUAGUCAGGGGGC | 193-G2-017 |
| 52 | L-RNA | GUGUGAUCUAGAUGUADWGGCUGWUCCUAGUYAGG | Type B Formula-1 |
| 53 | L-RNA | GUGUGAUCUAGAUGUADUGGCUGAUCCUAGUCAGG | Type B Formula-2 |
| 54 | L-RNA | AAAGUAACACGUAAAAUGAAAGGUAAC | |
| 55 | L-RNA | AAAGCAACAUGUCAAUGAAAGGUAGC | |
| 56 | L-RNA | GGUUAGGGCUAAAGUCGG | |
| 57 | L-RNA | GGUUAGGGCUAGAAGUCGG | |
| 58 | L-RNA | GGUUAGGGCUCGAAGUCGG | |
| 59 | L-RNA | GGUUAGGGCUUGAAGUCGG | |

TABLE 1-continued

| SEQ ID NO: | RNA/Peptide | Sequence | Internal Reference |
|---|---|---|---|
| 60 | L-RNA | GCUGUGAAAGCAACAUGUCAAUGAAAGGUAGCCGCAGC | 192-A10-001 |
| 61 | L-RNA | GCUGUGAAAGUAACAUGUCAAUGAAAGGUAACCACAGC | 192-G10 |
| 62 | L-RNA | GCUGUGAAAGUAACACGUCAAUGAAAGGUAACCGCAGC | 192-F10 |
| 63 | L-RNA | GCUGUGAAAGUAACACGUCAAUGAAAGGUAACCACAGC | 192-B11 |
| 64 | L-RNA | GCUGUAAAAGUAACAUGUCAAUGAAAGGUAACUACAGC | 192-C9 |
| 65 | L-RNA | GCUGUAAAAGUAACAAGUCAAUGAAAGGUAACUACAGC | 192-E10 |
| 66 | L-RNA | GCUGUGAAAGUAACAAGUCAAUGAAAGGUAACCACAGC | 192-C10 |
| 67 | L-RNA | GCAGUGAAAGUAACAUGUCAAUGAAAGGUAACCACAGC | 192-D11 |
| 68 | L-RNA | GCUGUGAAAGUAACAUGUCAAUGAAAGGUAACCACUGC | 192-G11 |
| 69 | L-RNA | GCUAUGAAAGUAACAUGUCAAUGAAAGGUAACCAUAGC | 192-H11 |
| 70 | L-RNA | GCUGCGAAAGCGACAUGUCAAUGAAAGGUAGCCGCAGC | 192-D10 |
| 71 | L-RNA | GCUGUGAAAGCAACAUGUCAAUGAAAGGUAGCCACAGC | 192-E9 |
| 72 | L-RNA | GCUGUGAAAGUAACAUGUCAAUGAAAGGUAGCCGCAGC | 192-H9 |
| 73 | L-RNA | AGCGUGAAAGUAACACGUAAAAUGAAAGGUAACCACGCU | 191-A6 |
| 74 | L-RNA | AAAGYRACAHGUMAAXAUGAAAGGUARC; $X_A$ = A or absent | Type A Formula-1 |
| 75 | L-RNA | AAAGYRACAHGUMAAUGAAAGGUARC | Type A Formula-2 |
| 76 | L-RNA | AAAGYRACAHGUMAAAUGAAAGGUARC | Type A Formula-3 |
| 77 | L-RNA | AAAGYAACAHGUCAAUGAAAGGUARC | Type A Formula-4 |
| 78 | L-RNA | CUGUGAAAGCAACAUGUCAAUGAAAGGUAGCCGCAG | 192-A10-002 |
| 79 | L-RNA | UGUGAAAGCAACAUGUCAAUGAAAGGUAGCCGCA | 192-A10-003 |
| 80 | L-RNA | GUGAAAGCAACAUGUCAAUGAAAGGUAGCCGC | 192-A10-004 |
| 81 | L-RNA | UGAAAGCAACAUGUCAAUGAAAGGUAGCCG | 192-A10-005 |
| 82 | L-RNA | GAAAGCAACAUGUCAAUGAAAGGUAGCC | 192-A10-006 |
| 83 | L-RNA | AAAGCAACAUGUCAAUGAAAGGUAGC | 192-A10-007 |
| 84 | L-RNA | GCGUGAAAGCAACAUGUCAAUGAAAGGUAGCCGCGC | 192-A10-008 |
| 85 | L-RNA | GCGCGAAAGCAACAUGUCAAUGAAAGGUAGCCGCGC | 192-A10-015 |
| 86 | L-RNA | GCGGAAAGCAACAUGUCAAUGAAAGGUAGCCCGC | 192-A10-014 |
| 87 | L-RNA | CGUGAAAGCAACAUGUCAAUGAAAGGUAGCCGCG | 192-A10-016 |
| 88 | L-RNA | GCGCAAAGCAACAUGUCAAUGAAAGGUAGCGUGC | 192-A10-017 |
| 89 | L-RNA | GUGCAAAGCAACAUGUCAAUGAAAGGUAGCGCGC | 192-A10-018 |
| 90 | L-RNA | CGCGAAAGCAACAUGUCAAUGAAAGGUAGCCGUG | 192-A10-019 |
| 91 | L-RNA | GGGCAAAGCAACAUGUCAAUGAAAGGUAGCGCCC | 192-A10-020 |
| 92 | L-RNA | GGCCAAAGCAACAUGUCAAUGAAAGGUAGCGGCC | 192-A10-021 |
| 93 | L-RNA | GCCCAAAGCAACAUGUCAAUGAAAGGUAGCGGGC | 192-A10-022 |
| 94 | L-RNA | CCCCAAAGCAACAUGUCAAUGAAAGGUAGCGGGG | 192-A10-023 |
| 95 | L-RNA | GUGCUGCGGGGGUUAGGGCUAGAAGUCGGCCUGCAGCAC | 197-B2 |
| 96 | L-RNA | AGCGUGGCGAGGUUAGGGCUAGAAGUCGGUCGACACGCU | 191-D5-001 |
| 97 | L-RNA | GUGUUGCGGAGGUUAGGGCUAGAAGUCGGUCAGCAGCAC | 197-H1 |

TABLE 1-continued

| SEQ ID NO: | RNA/Peptide | Sequence | Internal Reference |
|---|---|---|---|
| 98 | L-RNA | CGUGCGGCCUAAGAGGUUAGGGCUUAAAGUCGGUCUUUGGCCA ACACG | 190-D3 |
| 99 | L-RNA | CGUGCGCUUGAGAUAGGGGUUAGGGCUUAAAGUCGGCUGAUUC UCACG | 190-A3-001 |
| 100 | L-RNA | CGUGAUUGGUGAGGGGUUAGGGCUUGAAGUCGGCCUUGUCCAG UCACG | 190-A2 |
| 101 | L-RNA | AGCGUGAAGGGGUUAGGGCUCGAAGUCGGCUGACACGCU | 191-A5 |
| 102 | L-RNA | GUGCUGCGGGGGUUAGGGCUCGAAGUCGGCCCGCAGCAC | 197-H3 |
| 103 | L-RNA | GUGUUCCCGGGGUUAGGGCUUGAAGUCGGCCGGCAGCAC | 197-E1 |
| 104 | L-RNA | GUGUUGCAGGGGUUAGGGCUUGAAGUCGGCCUGCAGCAC | 197-E3 |
| 105 | L-RNA | GUGCUGCGGGGGUUAGGGCUCAAAGUCGGCCUGCAGCAC | 197-H2 |
| 106 | L-RNA | GUGCUGCCGGGGUUAGGGCUAA-AGUCGGCCGACAGCAC | 197-D1 |
| 107 | L-RNA | GUGCUGUGGGGGUCAGGGCUAGAAGUCGGCCUGCAGCAC | 197-D2 |
| 108 | L-RNA | GGUYAGGGCUHRXAAGUCGG; $X_A$ = A or absent | Type C Formula-1 |
| 109 | L-RNA | GGUYAGGGCUHRAAGUCGG | Type C Formula-2 |
| 110 | L-RNA | GGUYAGGGCUHRAGUCGG | Type C Formula-3 |
| 111 | L-RNA | GGUUAGGGCUHGAAGUCGG | Type C Formula-4 |
| 112 | L-RNA | UGAGAUAGGGGUUAGGGCUUAAAGUCGGCUGAUUCUCA | 190-A3-003 |
| 113 | L-RNA | GAGAUAGGGGUUAGGGCUUAAAGUCGGCUGAUUCUC | 190-A3-004 |
| 114 | L-RNA | GGGGUUAGGGCUUAAAGUCGGCUGAUUCU | 190-A3-007 |
| 115 | L-RNA | GCGUGGCGAGGUUAGGGCUAGAAGUCGGUCGACACGC | 191-D5-002 |
| 116 | L-RNA | CGUGGCGAGGUUAGGGCUAGAAGUCGGUCGACACG | 191-D5-003 |
| 117 | L-RNA | CGGGCGAGGUUAGGGCUAGAAGUCGGUCGACCG | 191-D5-004 |
| 118 | L-RNA | CGGGCGAGGUUAGGGCUAGAAGUCGGUCGCCCG | 191-D5-005 |
| 119 | L-RNA | CGGCGAGGUUAGGGCUAGAAGUCGGUCGCCG | 191-D5-006 |
| 120 | L-RNA | CGGGAGGUUAGGGCUAGAAGUCGGUCCCG | 191-D5-007 |
| 121 | L-RNA | GGGAGGUUAGGGCUAGAAGUCGGUCCC | 191-D5-010 |
| 122 | L-RNA | CCGCGGUUAGGGCUAGAAGUCGGGCGG | 191-D5-017 |
| 123 | L-RNA | CCCGGGUUAGGGCUAGAAGUCGGCGGG | 191-D5-029 |
| 124 | L-RNA | GGCGGGUUAGGGCUAGAAGUCGGCGCC | 191-D5-024 |
| 125 | L-RNA | CCCGCGGUUAGGGCUAGAAGUCGGGCGGG | 191-D5-017-29a |
| 126 | L-RNA | GCCGCGGUUAGGGCUAGAAGUCGGGCGGC | 191-D5-017-29b |
| 127 | L-RNA | CCCCGGGUUAGGGCUAGAAGUCGGCGGGG | 191-D5-019-29a |
| 128 | L-RNA | CGGCGGGUUAGGGCUAGAAGUCGGCGCCG | 191-D5-024-29a |
| 129 | L-RNA | GGGCGGGUUAGGGCUAGAAGUCGGCGCCC | 191-D5-024-29b |
| 130 | L-RNA | UGCUGCGGGGGUUAGGGCUAGAAGUCGGCCUGCAGCA | 197-B2-001 |
| 131 | L-RNA | GCUGCGGGGGUUAGGGCUAGAAGUCGGCCUGCAGC | 197-B2-002 |
| 132 | L-RNA | CUGCGGGGGUUAGGGCUAGAAGUCGGCCUGCAG | 197-B2-003 |
| 133 | L-RNA | UGCGGGGGUUAGGGCUAGAAGUCGGCCUGCA | 197-B2-004 |
| 134 | L-RNA | GCGGGGGUUAGGGCUAGAAGUCGGCCUGC | 197-B2-005 |

TABLE 1-continued

| SEQ ID NO: | RNA/Peptide | Sequence | Internal Reference |
|---|---|---|---|
| 135 | L-RNA | GCCGGGGUUAGGGCUAGAAGUCGGCCGGC | 197-B2-006 |
| 136 | L-RNA | GGCCGGGGUUAGGGCUAGAAGUCGGCCGGCC | 197-B2-006-31a |
| 137 | L-RNA | CGCCGGGGUUAGGGCUAGAAGUCGGCCGGCG | 197-B2-006-31b |
| 138 | L-RNA | RKSBUSNVGR | Type C Formula-5-5' |
| 139 | L-RNA | YYNRCASSMY | Type C Formula-5-3' |
| 140 | L-RNA | RKSBUGSVGR | Type C Formula-6-5' |
| 141 | L-RNA | YCNRCASSMY | Type C Formula-6-3' |
| 142 | L-RNA | CGUGGUCCGUUGUGUCAGGUCUAUUCGCCCCGGUGCAGGGCAUCCGCG | 194-A2-001 |
| 143 | L-RNA | GCAGUGUGACGCGGACGUGAUAGGACAGAGCUGAUCCCGCUCAGGUGAG | 196-B12-003 |
| 144 | L-RNA | CAACAGCAGUGUGACGCGGACGUGAUAGGACAGAGCUGAUCCCGCUCAG | 196-B12-004 |
| 145 | L-RNA | 5'-40 kDa-PEG-<br>GCGUGAAAGCAACAUGUCAAUGAAAGGUAGCCGCGC | 192-A10-008-5'-PEG |
| 146 | D-RNA | GCUGUGAAAGCAACAUGUCAAUGAAAGGUAGCCGCAGC | 192-A10-001 |
| 147 | D-RNA | GCUGUGAAAGUAACAUGUCAAUGAAAGGUAACCACAGC | 192-G10 |
| 148 | D-RNA | GCUGUGAAAGUAACACGUCAAUGAAAGGUAACCGCAGC | 192-F10 |
| 149 | D-RNA | GCUGUGAAAGUAACACGUCAAUGAAAGGUAACCACAGC | 192-B11 |
| 150 | D-RNA | GCUGUAAAAGUAACAUGUCAAUGAAAGGUAACUACAGC | 192-C9 |
| 151 | D-RNA | GCUGUAAAAGUAACAAGUCAAUGAAAGGUAACUACAGC | 192-E10 |
| 152 | D-RNA | GCUGUGAAAGUAACAAGUCAAUGAAAGGUAACCACAGC | 192-C10 |
| 153 | D-RNA | GCAGUGAAAGUAACAUGUCAAUGAAAGGUAACCACAGC | 192-D11 |
| 154 | D-RNA | GCUGUGAAAGUAACAUGUCAAUGAAAGGUAACCACUGC | 192-G11 |
| 155 | D-RNA | GCUAUGAAAGUAACAUGUCAAUGAAAGGUAACCAUAGC | 192-H11 |
| 156 | D-RNA | GCUGCGAAAGCGACAUGUCAAUGAAAGGUAGCCGCAGC | 192-D10 |
| 157 | D-RNA | GCUGUGAAAGCAACAUGUCAAUGAAAGGUAGCCACAGC | 192-E9 |
| 158 | D-RNA | GCUGUGAAAGUAACAUGUCAAUGAAAGGUAGCCGCAGC | 192-H9 |
| 159 | D-RNA | AGCGUGAAAGUAACACGUAAAAUGAAAGGUAACCACGCU | 191-A6 |
| 160 | D-RNA | CUGUGAAAGCAACAUGUCAAUGAAAGGUAGCCGCAG | 192-A10-002 |
| 161 | D-RNA | UGUGAAAGCAACAUGUCAAUGAAAGGUAGCCGCA | 192-A10-003 |
| 162 | D-RNA | GUGAAAGCAACAUGUCAAUGAAAGGUAGCCGC | 192-A10-004 |
| 163 | D-RNA | UGAAAGCAACAUGUCAAUGAAAGGUAGCCG | 192-A10-005 |
| 164 | D-RNA | GAAAGCAACAUGUCAAUGAAAGGUAGCC | 192-A10-006 |
| 165 | D-RNA | AAAGCAACAUGUCAAUGAAAGGUAGC | 192-A10-007 |
| 166 | D-RNA | GCGUGAAAGCAACAUGUCAAUGAAAGGUAGCCGCGC | 192-A10-008 |
| 167 | D-RNA | GCGCGAAAGCAACAUGUCAAUGAAAGGUAGCCGCGC | 192-A10-015 |
| 168 | D-RNA | GCGGAAAGCAACAUGUCAAUGAAAGGUAGCCCGC | 192-A10-014 |
| 169 | D-RNA | CGUGAAAGCAACAUGUCAAUGAAAGGUAGCCGCG | 192-A10-016 |
| 170 | D-RNA | GCGCAAAGCAACAUGUCAAUGAAAGGUAGCGUGC | 192-A10-017 |
| 171 | D-RNA | GUGCAAAGCAACAUGUCAAUGAAAGGUAGCGCGC | 192-A10-018 |
| 172 | D-RNA | CGCGAAAGCAACAUGUCAAUGAAAGGUAGCCGUG | 192-A10-019 |

TABLE 1-continued

| SEQ ID NO: | RNA/Peptide | Sequence | Internal Reference |
|---|---|---|---|
| 173 | D-RNA | GGGCAAAGCAACAUGUCAAUGAAAGGUAGCGCCC | 192-A10-020 |
| 174 | D-RNA | GGCCAAAGCAACAUGUCAAUGAAAGGUAGCGGCC | 192-A10-021 |
| 175 | D-RNA | GCCCAAAGCAACAUGUCAAUGAAAGGUAGCGGGC | 192-A10-022 |
| 176 | D-RNA | CCCCAAAGCAACAUGUCAAUGAAAGGUAGCGGGG | 192-A10-023 |
| 177 | D-RNA | GUGCUGCGGGGGUUAGGGCUAGAAGUCGGCCUGCAGCAC | 197-B2 |
| 178 | D-RNA | AGCGUGGCGAGGUUAGGGCUAGAAGUCGGUCGACACGCU | 191-D5-001 |
| 179 | D-RNA | GUGUUGCGGAGGUUAGGGCUAGAAGUCGGUCAGCAGCAC | 197-H1 |
| 180 | D-RNA | CGUGCGGCCUAAGAGGUUAGGGCUUAAAGUCGGUCUUUGGCCA ACACG | 190-D3 |
| 181 | D-RNA | CGUGCGCUUGAGAUAGGGGUUAGGGCUUAAAGUCGGCUGAUUC UCACG | 190-A3-001 |
| 182 | D-RNA | CGUGAUUGGUGAGGGGUUAGGGCUUGAAGUCGGCCUUGUCCAG UCACG | 190-A2 |
| 183 | D-RNA | AGCGUGAAGGGGUUAGGGCUCGAAGUCGGCUGACACGCU | 191-A5 |
| 184 | D-RNA | GUGCUGCGGGGGUUAGGGCUCGAAGUCGGCCCGCAGCAC | 197-H3 |
| 185 | D-RNA | GUGUUCCCGGGGUUAGGGCUUGAAGUCGGCCGGCAGCAC | 197-B1 |
| 186 | D-RNA | GUGUUGCAGGGGUUAGGGCUUGAAGUCGGCCUGCAGCAC | 197-E3 |
| 187 | D-RNA | GUGCUGCGGGGGUUAGGGCUCAAAGUCGGCCUGCAGCAC | 197-H2 |
| 188 | D-RNA | GUGCUGCCGGGGUUAGGGCUAA-AGUCGGCCGACAGCAC | 197-D1 |
| 189 | D-RNA | GUGCUGUGGGGGUCAGGGCUAGAAGUCGGCCUGCAGCAC | 197-D2 |
| 190 | D-RNA | UGAGAUAGGGGUUAGGGCUUAAAGUCGGCUGAUUCUCA | 190-A3-003 |
| 191 | D-RNA | GAGAUAGGGGUUAGGGCUUAAAGUCGGCUGAUUCUC | 190-A3-004 |
| 192 | D-RNA | GGGGUUAGGGCUUAAAGUCGGCUGAUUCU | 190-A3-007 |
| 193 | D-RNA | GCGUGGCGAGGUUAGGGCUAGAAGUCGGUCGACACGC | 191-D5-002 |
| 194 | D-RNA | CGUGGCGAGGUUAGGGCUAGAAGUCGGUCGACACG | 191-D5-003 |
| 195 | D-RNA | CGGGCGAGGUUAGGGCUAGAAGUCGGUCGACCG | 191-D5-004 |
| 196 | D-RNA | CGGGCGAGGUUAGGGCUAGAAGUCGGUCGCCCG | 191-D5-005 |
| 197 | D-RNA | CGGCGAGGUUAGGGCUAGAAGUCGGUCGCCG | 191-D5-006 |
| 198 | D-RNA | CGGGAGGUUAGGGCUAGAAGUCGGUCCCG | 191-D5-007 |
| 199 | D-RNA | GGGAGGUUAGGGCUAGAAGUCGGUCCC | 191-D5-010 |
| 200 | D-RNA | CCGCGGUUAGGGCUAGAAGUCGGGCGG | 191-D5-017 |
| 201 | D-RNA | CCCGGGUUAGGGCUAGAAGUCGGCGGG | 191-D5-029 |
| 202 | D-RNA | GGCGGGUUAGGGCUAGAAGUCGGCGCC | 191-D5-024 |
| 203 | D-RNA | CCCGCGGUUAGGGCUAGAAGUCGGGCGGG | 191-D5-017-29a |
| 204 | D-RNA | GCCGCGGUUAGGGCUAGAAGUCGGGCGGC | 191-D5-017-29b |
| 205 | D-RNA | CCCCGGGUUAGGGCUAGAAGUCGGCGGGG | 191-D5-019-29a |
| 206 | D-RNA | CGGCGGGUUAGGGCUAGAAGUCGGCGCCG | 191-D5-024-29a |
| 207 | D-RNA | GGGCGGGUUAGGGCUAGAAGUCGGCGCCC | 191-D5-024-29b |
| 208 | D-RNA | UGCUGCGGGGGUUAGGGCUAGAAGUCGGCCUGCAGCA | 197-B2-001 |
| 209 | D-RNA | GCUGCGGGGGUUAGGGCUAGAAGUCGGCCUGCAGC | 197-B2-002 |

TABLE 1-continued

| SEQ ID NO: | RNA/Peptide | Sequence | Internal Reference |
|---|---|---|---|
| 210 | D-RNA | CUGCGGGGGUUAGGGCUAGAAGUCGGCCUGCAG | 197-B2-003 |
| 211 | D-RNA | UGCGGGGGUUAGGGCUAGAAGUCGGCCUGCA | 197-B2-004 |
| 212 | D-RNA | GCGGGGGUUAGGGCUAGAAGUCGGCCUGC | 197-B2-005 |
| 213 | D-RNA | GCCGGGGUUAGGGCUAGAAGUCGGCCGGC | 197-B2-006 |
| 214 | D-RNA | GGCCGGGGUUAGGGCUAGAAGUCGGCCGGCC | 197-B2-006-31a |
| 215 | D-RNA | CGCCGGGGUUAGGGCUAGAAGUCGGCCGGCG | 197-B2-006-31b |
| 216 | D-RNA | CGUGGUCCGUUGUGUCAGGUCUAUUCGCCCCGGUGCAGGGCAUCCGCG | 194-A2-001 |
| 217 | D-RNA | GCAGUGUGACGCGGACGUGAUAGGACAGAGCUGAUCCCGCUCAGGUGAG | 196-B12-003 |
| 218 | D-RNA | CAACAGCAGUGUGACGCGGACGUGAUAGGACAGAGCUGAUCCCGCUCAG | 196-B12-004 |
| 219 | L-RNA | 5'-40 kDa-PEG-UAAGGAAACUCGGUCUGAUGCGGUAGCGCUGUGCAGAGCU | Control Spiegelmer |
| 220 | L-RNA | CGUGCGCUUGAGAUAGG | |
| 221 | L-RNA | CUGAUUCUCACG | |
| 222 | L-RNA | CUGAUUCUCA | |
| 223 | L-RNA | 5'-40 kDa-PEG-GCCGGGGUUAGGGCUAGAAGUCGGCCGGC | 197-B2-006-5'-PEG |
| 224 | L-RNA | 5'-40 kDa-PEG-CGGGAGGUUAGGGCUAGAAGUCGGUCCCG | 191-D5-007-5'PEG |
| 225 | L-RNA | 5'-40 kDa-PEG-CGCAUGGACUGAUCCUAGUCGGUUAUGUAGAUCUAGUGUGGUGCG | revNOX-A12 |

The present invention is further illustrated by the figures, examples and the sequence listing from which further features, embodiments and advantages may be taken, wherein FIG. 1 shows an alignment of sequences of SDF-1 binding nucleic acid molecules of "type A";

FIGS. 2A+B show derivatives of SDF-1 binding nucleic acid molecule 192-A10-001 (SDF-1 binding nucleic acid molecules of "type A");

FIG. 3 shows an alignment of sequences of SDF-1 binding nucleic acid molecules of "type B";

FIGS. 4A+B show derivatives of SDF-1 binding nucleic acid molecules 193-C2-001 and 193-G2-001 (SDF-1 binding nucleic acid molecules of type B);

FIG. 5 shows an alignment of sequences of SDF-1 binding nucleic acid molecules of "type C";

FIG. 6 shows derivatives of SDF-1 binding nucleic acid molecule 190-A3-001 (SDF-1 binding nucleic acid molecules of "type C");

Figure 10:
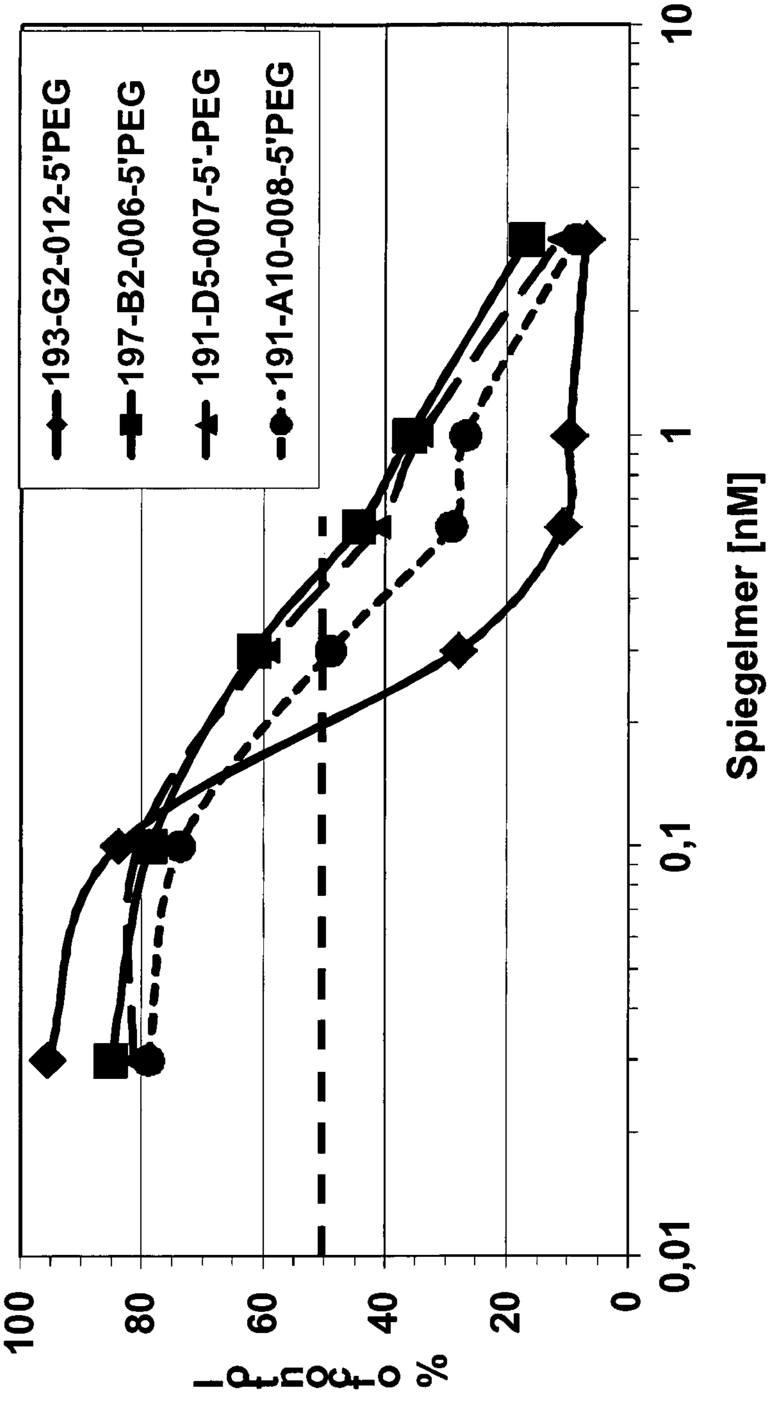
Figure 12:
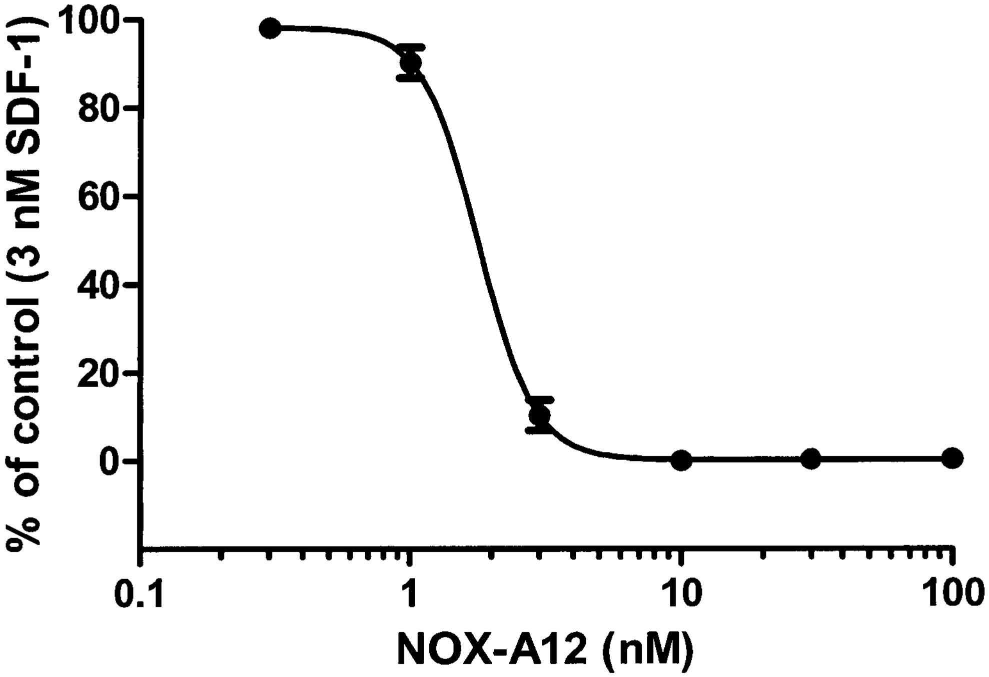
Figure 13:
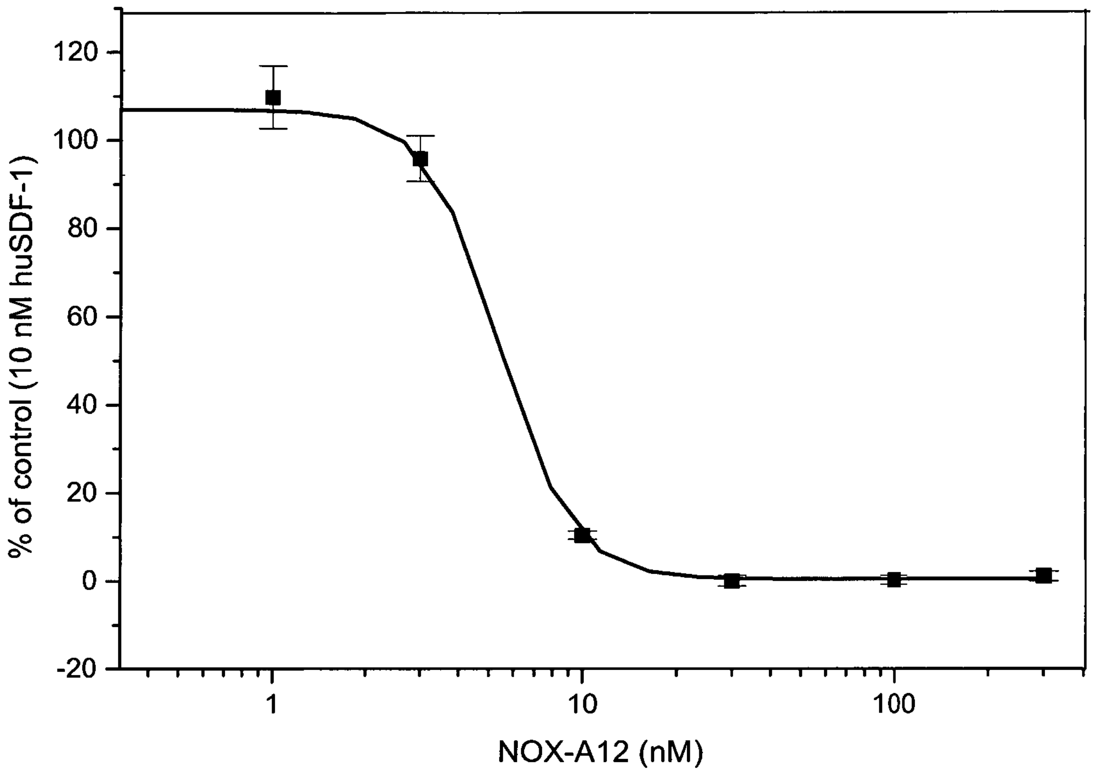
Figure 14:
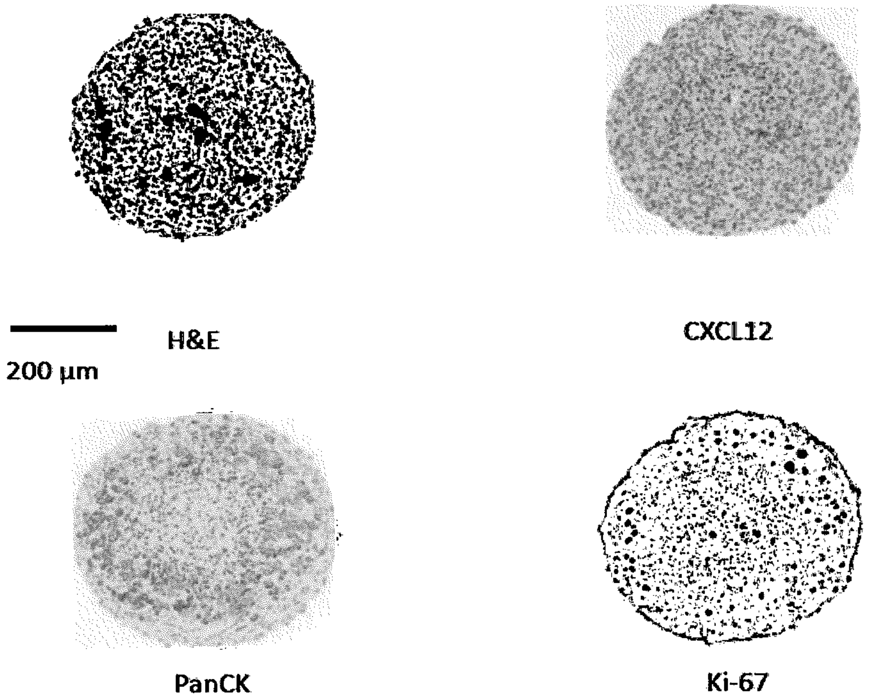
Figure 15:
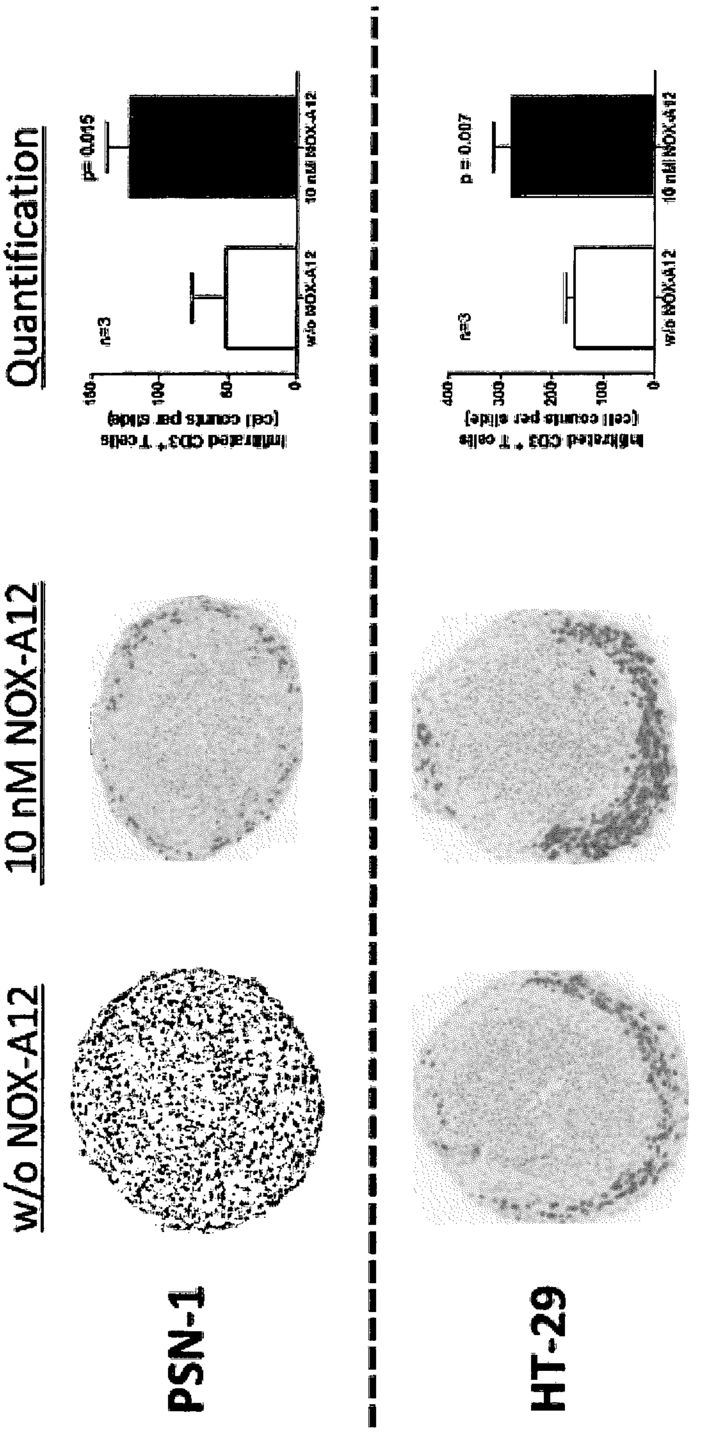
Figure 16:
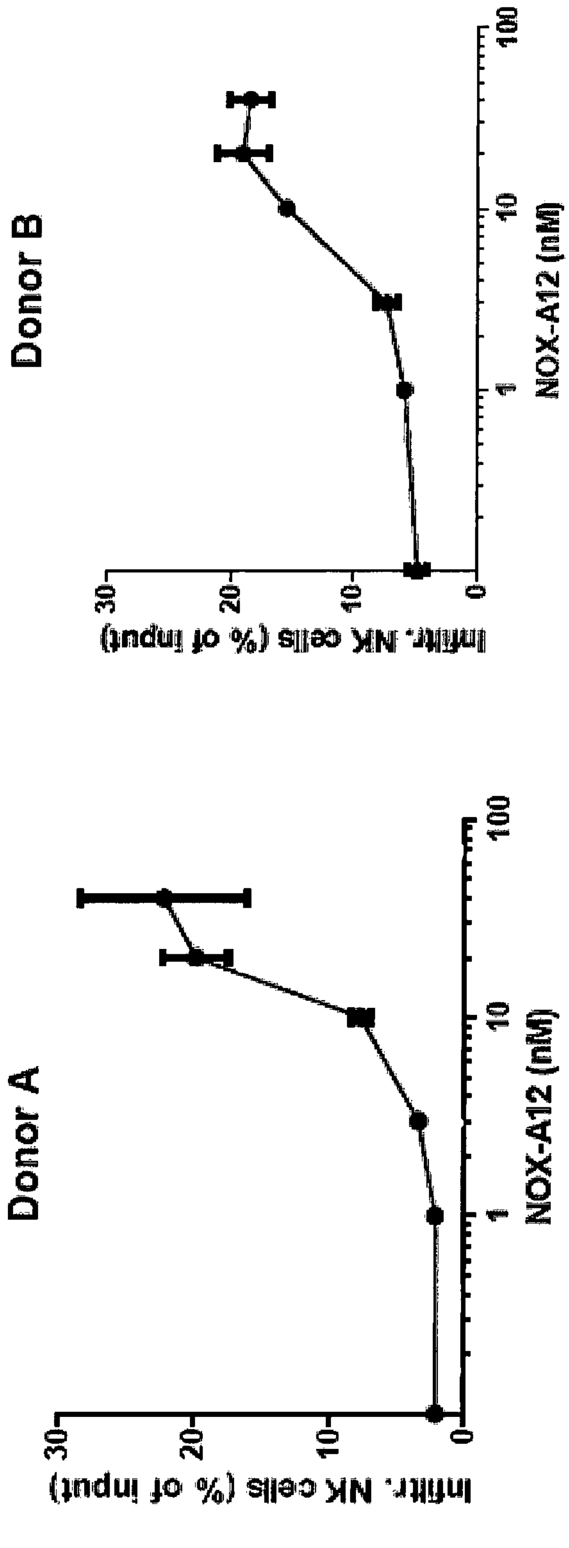
Figure 17:
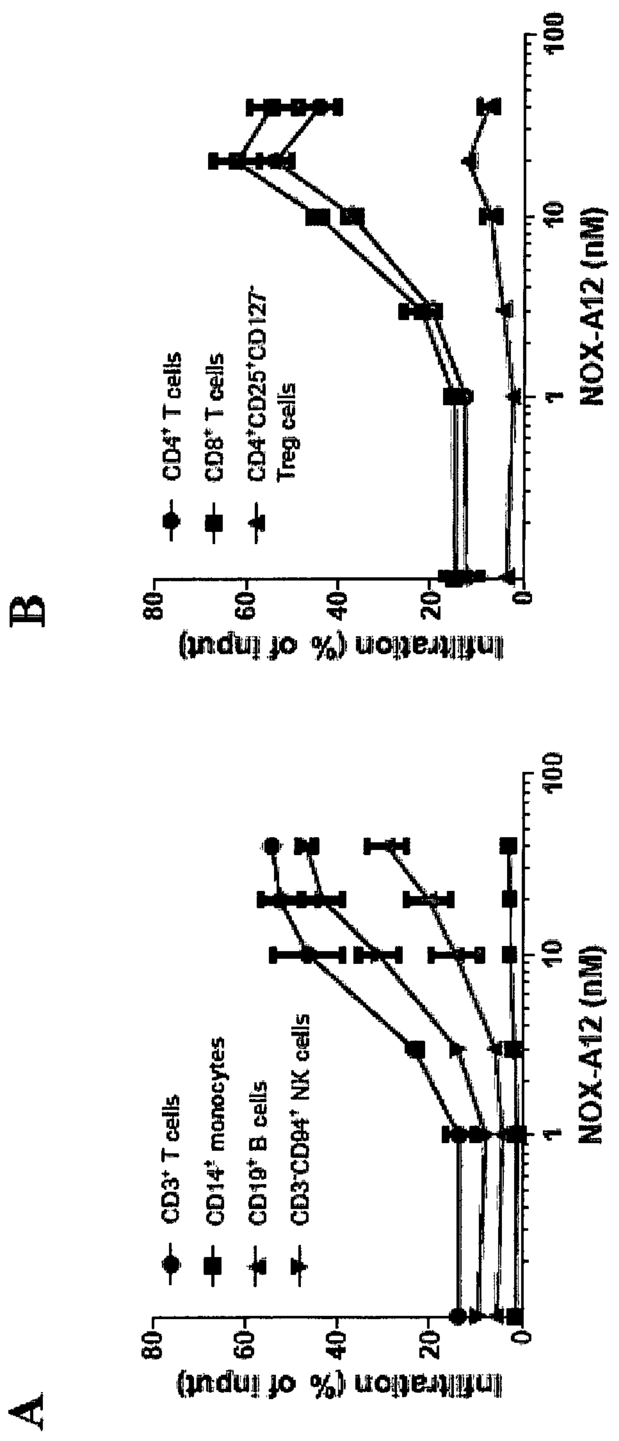
Figure 18:
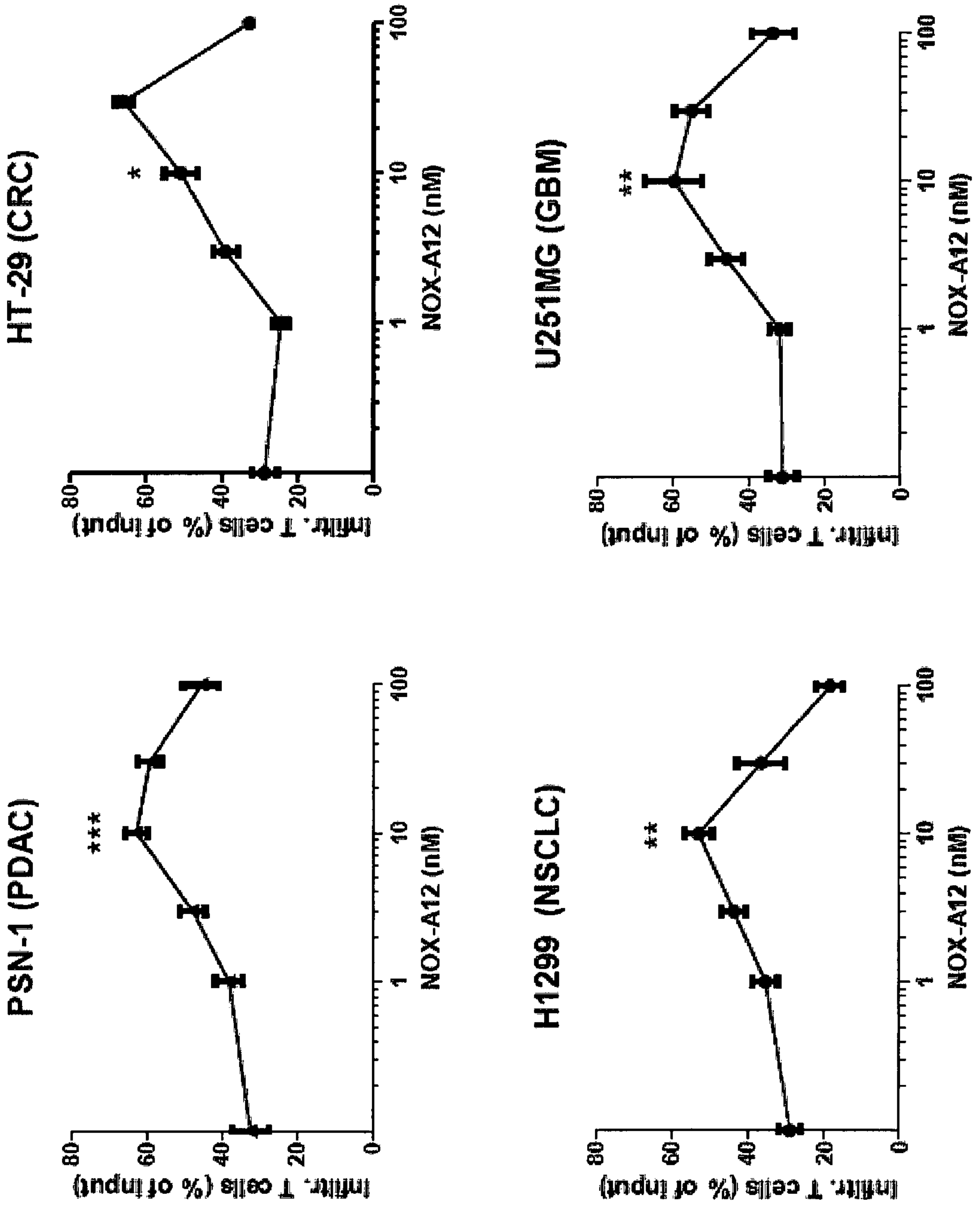
Figure 19:
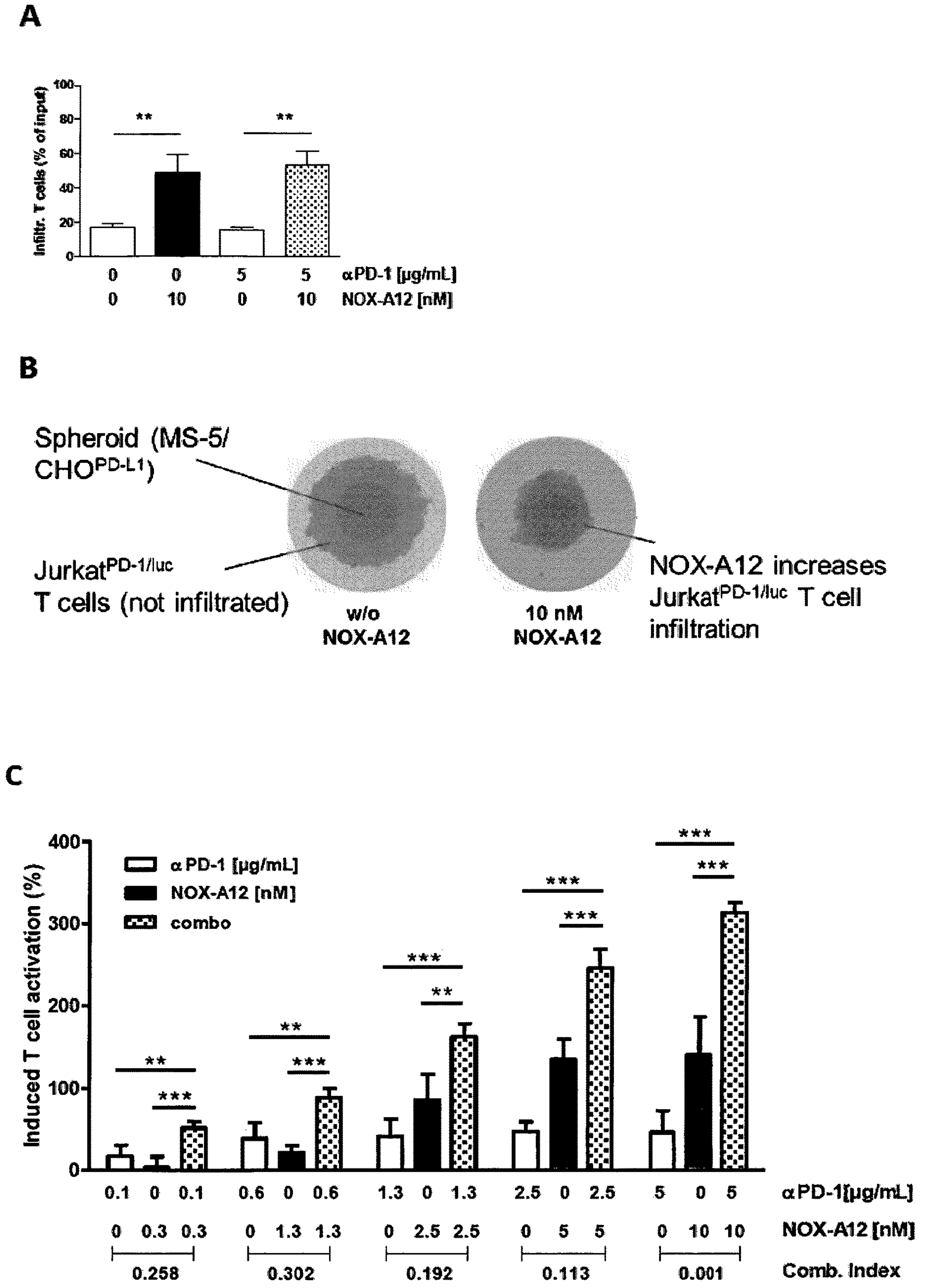
Figure 20:
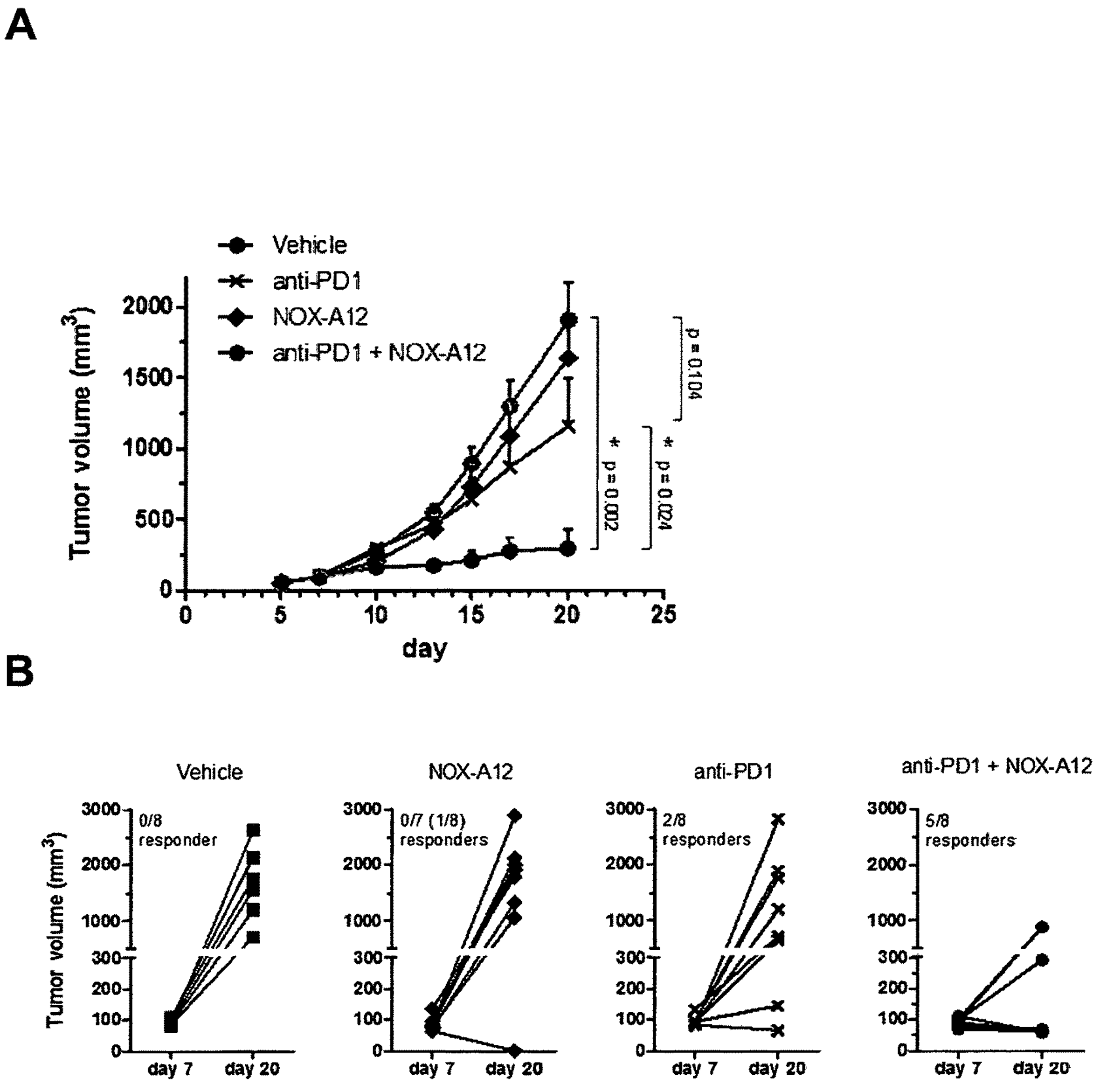
Figure 21:
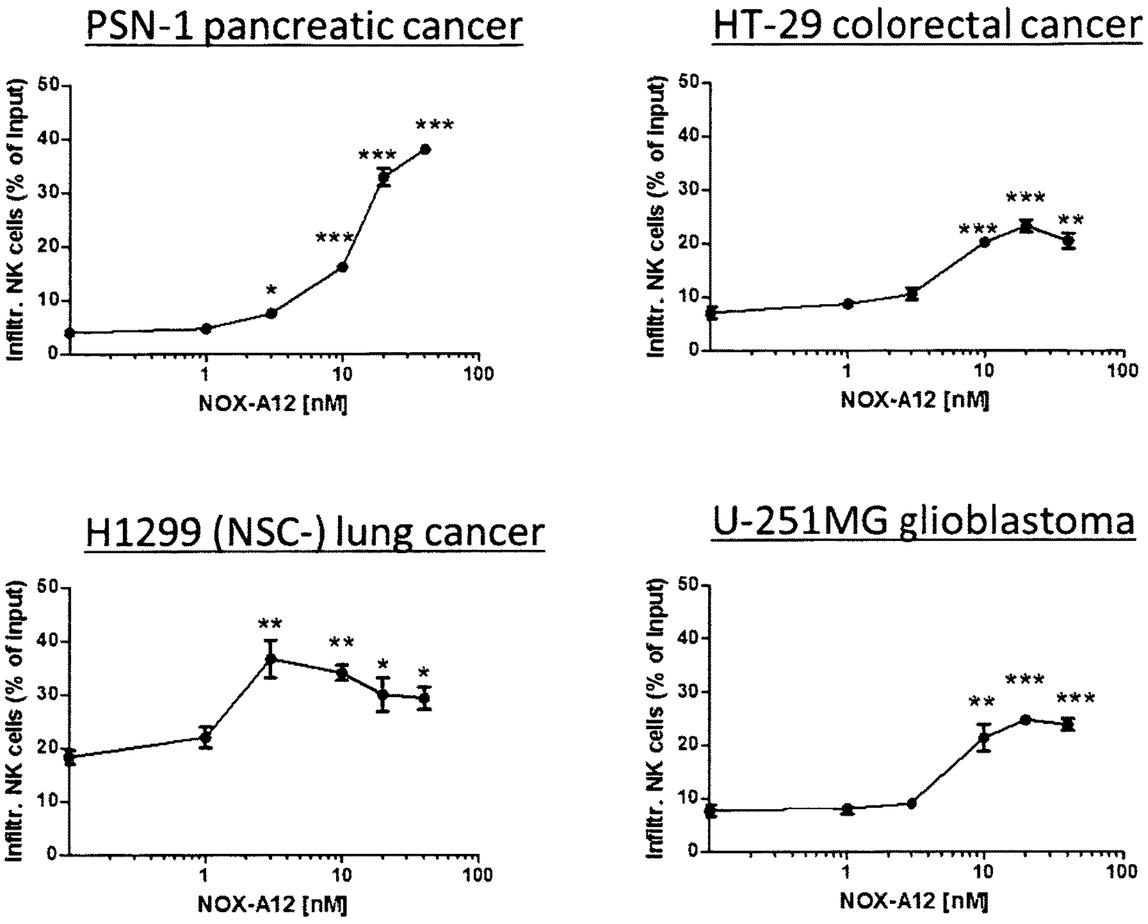
Figure 22:
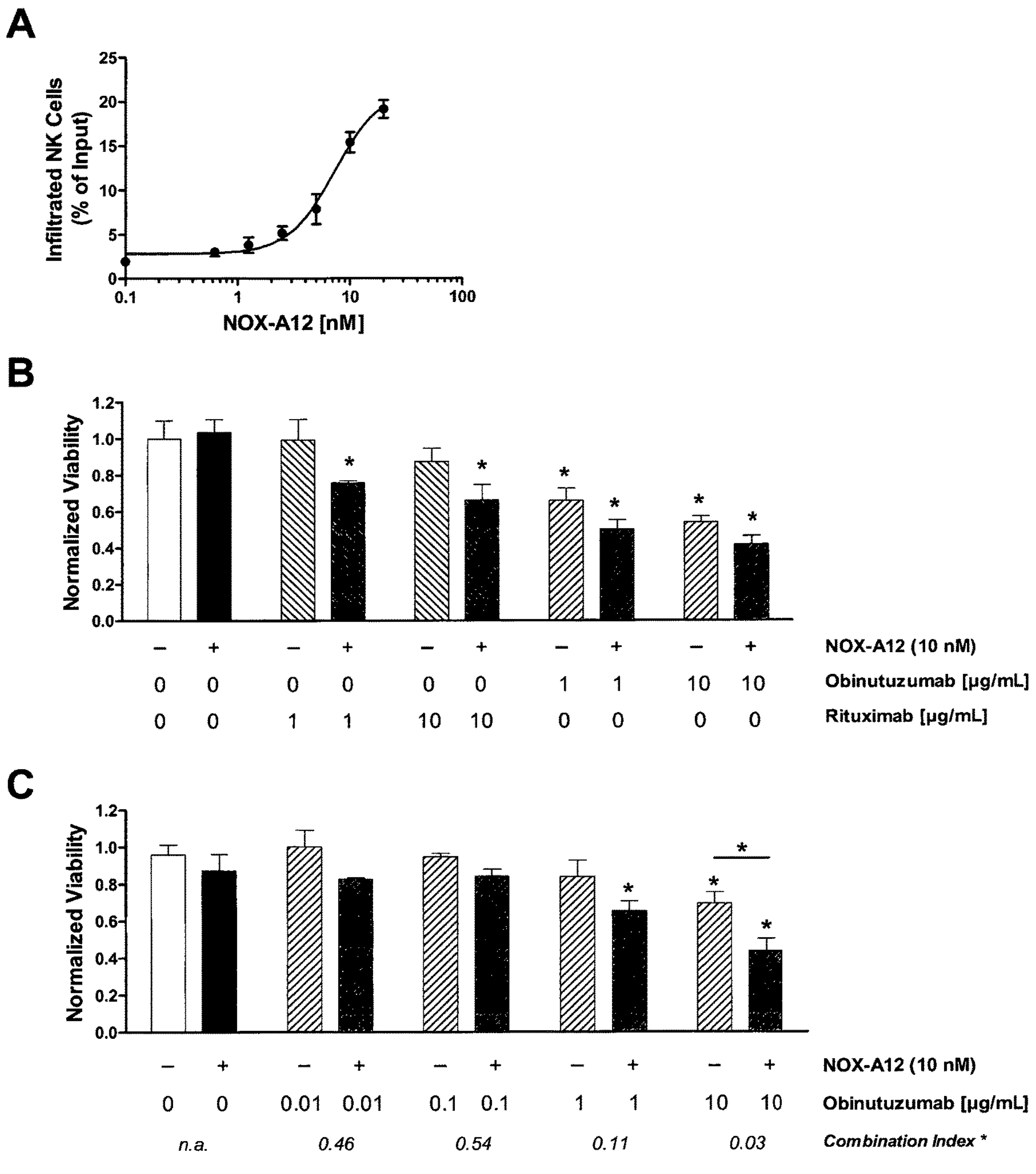

FIGS. 7A+B show derivatives of SDF-1 binding nucleic acid molecules 190-D5-001 (SDF-1 binding nucleic acid molecules of "type C");

FIG. 8 shows derivatives of SDF-1 binding nucleic acid molecule 197-B2 (SDF-1 binding nucleic acid molecule of "type C");

FIG. 9 shows further SDF-1 binding nucleic acid molecules molecules which are, in addition to other SDF-1 binding nucleic acid molecules, also referred to as SDF-1 binding nucleic acid molecules of "type D";

FIG. 10 shows the efficacy of SDF-1 binding Spiegelmers 193-G2-012-5'-PEG (also referred to as NOX-A12), 197-B2-006-5'-PEG, 191-D5-007-5'-PEG and 191-A10-008-5'-PEG in a chemotaxis assay with the human T cell leukemia cell line Jurkat whereby cells were allowed to migrate towards 0.3 nM human SDF-1 preincubated at 37° C. with various amounts of Spiegelmers 193-G2-012-5'-PEG, 197-B2-006-5'-PEG, 191-D5-007-5'-PEG and 191-A10-008-5'-PEG, represented as percentage of control over concentration of Spiegelmers 193-G2-012-5'-PEG, 197-B2-006-5'-PEG, 191-D5-007-5'-PEG and 191-A10-008-5'-PEG;

FIG. 11A shows the efficacy of SDF-1 binding Spiegelmer NOX-A12 in a chemotaxis assay with the human pre-B ALL cell line Nalm-6 whereby cells were allowed to migrate towards 0.3 nM human SDF-1 preincubated at 37° C. with various amounts of Spiegelmer NOX-A12 represented as percentage of control over concentration of Spiegelmer NOX-A12;

FIG. 11B shows the efficacy of SDF-1 binding Spiegelmer NOX-A12 in a chemotaxis assay with the human leukemic monocyte lymphoma cell line U937 whereby cells were allowed to migrate towards 3 nM human SDF-1 preincubated at 37° C. with various amounts of Spiegelmer NOX-A12 represented as percentage of control over concentration of Spiegelmer NOX-A12;

FIG. 12 shows the efficacy of SDF-1 binding Spiegelmer NOX-A12 in a chemotaxis assay with the human pre-B cell leukemia cell line BV-173 whereby cells were allowed to migrate towards 3 nM human SDF-1 preincubated at 37° C. with various amounts of Spiegelmer NOX-A12 represented as percentage of control over concentration of Spiegelmer NOX-A12;

FIG. 13 shows the efficacy of SDF-1 binding Spiegelmer NOX-A12 in a complementation assay with CHO cells stably expressing CXCR7 and β-arrestin both fused to a fragment of β-galactosidase whereby CXCR7 of the cells were activated towards 10 nM human SDF-1 preincubated at 37° C. with various amounts of Spiegelmer NOX-A12 represented as percentage of control over concentration of Spiegelmer NOX-A12;

FIG. 14 shows representative PSN-1/MS5 tumor/stroma spheroids; the spheroids are compact structures (H&E) with an even distribution of CXCL12 (except in the center, which may be partly necrotic). Pan cytokeratine only stains the tumor cells since they are of epithelial origin and the stromal cells are not. Tumor cells were found not to form a single cluster but are distributed within the spheroid quite well. Ki-67 staining shows that the cells are alive and proliferating;

FIG. 15 shows that NOX-A12 enhances T cell infiltration (brown spots=CD3+ T cells); PSN-1 spheroids were repeatedly shaken during the incubation with T-cells, while HT29-spheroids were not. This explains why only the lower hemisphere where there was direct contact with settled T cells was present, was infiltrated;

FIG. 16 shows that NOX-A12 increases the infiltration of NK cells into tumor/stroma microtissues as shown by FACS analysis;

FIG. 17 shows A: when PBMC are added to the spheroids, NOX-A12 enhances infiltration of NK cells, and T cells; B cell infiltration is promoted to a lesser extent; monocyte/macrophage infiltration was not increased by NOX-A12; B: more detailed analysis of T cell subsets that infiltrate the tumor after incubation of the spheroid with Pan T cells: Infiltration of CD8+ T cells, CD4+ T cells and NK cells is enhanced by NOX-A12, and to a lesser extent the infiltration of Treg;

FIG. 18 shows that NOX-A12 enhances infiltration of primary human CD3+ T cells into various tumor-stroma spheroids in a dose-dependent manner;

FIG. 19 (A) NOX-A12, but not anti-PD-1, increases T cell infiltration; (B) light microscopy showing the effect of NOX-A12 on the infiltration of T cells; (C) NOX-A12 dose-dependently increases T cell activation probably by increasing T cell infiltration and thereby facilitating physical contact of T cells with tumor cells; NOX-A12 acts synergistically with anti-PD-1 (Comb. Index<1). *p<0.05; p<0.01; *p<0.001;

FIG. 20 shows that NOX-A12 significantly enhances the efficacy of anti-PD-1 therapy in a syngeneic subcutaneous CT-26 colon cancer mouse model; treatment with NOX-A12 (20 mg/kg, s.c., q2d) and anti-PD1 antibody (10 mg/kg RMP1-14, i.p., twice weekly) was initiated at day 5 and 7, respectively; A, mean tumor volumes (n=8, ±SEM); B, individual tumor volumes;

FIG. 21 shows that NOX-A12 enhances infiltration of primary human NK cells into various tumor-stroma spheroids in a dose-dependent manner;

FIG. 22 shows that NOX-A12 dose-dependently increases NK cell infiltration (A), thereby facilitating physical contact of NK cells with Raji lymphoma cells; NOX-A12 enhances the efficacy of anti-CD20 mAbs rituximab and obinutuzumab in terms of lymphoma cell killing (B) and acts synergistically with obinutuzumab (C) (Comb. Index<1). *p<0.05; p<0.01; *p<0.001

EXAMPLE 1

Nucleic Acids that Bind Human SDF-1

In the following the terms 'nucleic acid' and 'nucleic acid molecule' are used herein in a synonymous manner if not indicated to the contrary. Moreover, the terms 'stretch' and 'stretch of nucleotide' are used herein in a synonymous manner if not indicated to the contrary.

L-nucleic acid molecules that bind to human SDF-1 and the respective nucleotide sequences are depicted in FIGS. 1 to 9. The nucleic acids were characterized on the aptamer, i. e. D-nucleic acid level using competitive or direct pull-down binding assays with biotinylated human D-SDF-1 (protocol, see Example 3). Spiegelmers were tested with the natural configuration of SDF-1 (L-SDF-1) by surface plasmon resonance measurement using a Biacore 2000 instrument (protocol, see Example 5) and a cell culture in vitro chemotaxis assay (protocol, see Example 4).

The SDF-1 binding nucleic acid molecules exhibit different sequence motifs, three main types are defined in FIGS. 1, 2A and 2B (Type A), FIGS. 3, 4A and 4B (Type B), FIGS. 5, 4, 7A, 7B and 8 (Type C). The nucleic acid molecules exhibit different sequence motifs. For definition of nucleotide sequence motifs, the IUPAC abbreviations for ambiguous nucleotides is used:

| | | |
|---|---|---|
| S | strong | G or C; |
| W | weak | A or U; |
| R | purine | G or A; |
| Y | pyrimidine | C or U; |
| K | keto | G or U; |
| M | imino | A or C; |
| B | not A | C or U or G; |
| D | not C | A or G or U; |
| H | not G | A or C or U; |
| V | not U | A or C or G; |
| N | all | A or G or C or U |

If not indicated to the contrary, any nucleic acid sequence or sequence of stretches and boxes, respectively, is indicated in the 5'→3' direction.

SDF-1 Binding Nucleic Acid Molecules of Type A

As depicted in FIG. 1 all sequences of SDF-1 binding nucleic acid molecules of type A comprise one central stretch of nucleotides which is flanked by the first (5'-) terminal and the second (3'-) terminal stretch of nucleotides (also referred to as first terminal stretch of nucleotides and second stretch of nucleotides) whereby both stretches can hybridize to each other. However, such hybridization is not necessarily given in the molecule.

In the following the terms 'SDF-1 binding nucleic acid molecules of type A' and 'Type A SDF-1 binding nucleic acids' or Type A SDF-1 binding nucleic acid molecules' are used herein in a synonymous manner if not indicated to the contrary.

The sequences of the defined boxes or stretches of nucleotides may be different between the SDF-1 binding nucleic acids of type A which influences the binding affinity to SDF-1. Based on binding analysis of the different SDF-1 binding nucleic acids summarized as Type A SDF-1 binding nucleic acids, the central stretch of nucleotides and its nucleotide sequences as described in the following are individually and more preferably in their entirety essential for binding to SDF-1.

The central stretch of nucleotides of all identified sequences of Type A SDF-1 binding nucleic acids share the sequence

AAAGYRACAHGUMAA$X_A$UGAAAGGUARC (Type A Formula-1, SEQ ID NO: 74), whereby $X_A$ is either absent or is 'A'. If 'A' is absent, the sequence of the central nucleotide sequence can be summarized as Type A Formula-2

(AAAGYRACAHGUMAA-UGAAAGGUARC,

SEQ ID NO: 75. Type A SDF-1 binding nucleic acid 191-A6 (central nucleotide sequence:

AAAGUAACACGUAAAAUGAAAGGUAAC,

SEQ ID NO: 54) carrying the additional nucleotide 'A' within the central nucleotide sequence and still binding to SDF-1 let conclude an alternative central nucleotide sequence (AAAGYRACAHGUMAAAUGAAAGGUARC, Type A Formula-3, SEQ ID NO: 76). Exemplarily for all the other nucleic acids of Type A SDF-1 binding nucleic acids, the Type A SDF-1 binding nucleic acid 192-A10-001 was characterized for its binding affinity to human SDF-1. The equilibrium binding constant $K_D$ was determined using the pull-down binding assay ($K_D$=1.5 nM) and by surface plasmon resonance measurement ($K_D$=1.0 nM). The $IC_{50}$ (inhibitory concentration 50%) of 0.12 nM for 192-A10-001 was measured using a cell culture in vitro chemotaxis assay. Consequently, all Type A SDF-1 binding nucleic acids as depicted in FIG. 1 were analyzed in a competitive pull-down binding assay vs. 192-A10-001. The Type A SDF-1 binding nucleic acids 192-B11 and 192-C10 showed equal binding affinities as 192-A10-001 in these competition experiments. Weaker binding affinity was determined for Type A SDF-1 binding nucleic acids 192-G10, 192-F10, 192-C9, 192-E10, 192-D11, 192-G11, 192-H11 and 191-A6. The Type A SDF-1 binding nucleic acids 192-D10, 192-E9 and 192-H9 have much weaker binding affinity than 192-A10-001.

As mentioned above, the Type A SDF-1 binding nucleic acid 192-B11 and 192-C10 exhibit equal binding affinity to SDF-1 as 192-A10-001. However, they show slight differences in the nucleotide sequence of the central stretch of nucleotides. Therefore the consensus sequence of the three molecules binding to SDF-1 with almost the same high affinity can be summarized by the nucleotide sequence

AAAGYAACAHGUCAAUGAAAGGUARC (Type A Formula-4, SEQ ID NO: 77)) whereby the nucleotide sequence of the central stretch of nucleotides of 192-A10-001 (nucleotide sequence:

AAAGCAACAUGUCAAUGAAAGGUAGC,

SEQ ID NO: 84) represents the nucleotide sequence with the best binding affinity of Type A SDF-1 binding nucleic acids.

Five or six out of the six nucleotides of the 5'-terminal stretch (also referred to as first terminal stretch) of Type A SDF-1 binding nucleic acids may hybridize to the respective five or six nucleotides out of the six nucleotides of the 3'-terminal stretch (also referred to as second terminal stretch) to form a terminal helix. Although these nucleotides are variable at several positions, the different nucleotides allow for hybridization of five or six out of the six nucleotides of the 5'- and 3'-terminal stretches each. The 5'-terminal and 3'-terminal stretches of Type A SDF-1 binding nucleic acids as shown in FIG. 1 can be summarized in a generic formula for the 5'-terminal stretch ('RSHRYR', Type A Formula-5-5') and for the 3'-terminal stretch ('YRYDSY', Type A Formula-5-3'). Truncated derivatives of Type A SDF-1 binding nucleic acid 192-A10-001 were analyzed in a competitive pull-down binding assay vs. the original molecule 192-A10-001 and 192-A10-008 (FIGS. 2A and 2B). These experiments showed that a reduction of the six terminal nucleotides (5'end: GCUGUG; 3'end: CGCAGC) of 192-A10-001 to five nucleotides (5'end: CUGUG; 3'end: CGCAG) of the derivative 192-A10-002 could be done without reduction of binding affinity. However, the truncation to four terminal nucleotides (5'end: UGUG; 3'end: CGCA; 192-A10-003) or less (192-A10-004/-005/-006/-007) led to reduced binding affinity to SDF-1 (FIG. 2A). The determined 5'-terminal and 3'-terminal stretches with a length of five and four nucleotides of the derivatives of Type A SDF-1 binding nucleic acid 192-A10-001 as shown in FIGS. 2A and 2B can be described in a generic formula for the 5'-terminal stretch ('$X_2$BBBS', Type A Formula-6-5') and of the 3'-terminal stretch ('SBBV$X_3$'; Type A Formula-6-3'), whereby X2 is either absent or is 'S' and $X_3$ is either absent or is 'S'.

The nucleotide sequence of the 5'- and 3'-terminal stretches has an influence on the binding affinity of Type A SDF-1 binding nucleic acids. This is not only shown by the nucleic acids 192-F10 and 192-E10, but also by derivatives of 192-A10-001 (FIG. 2B). The central stretch of 192-F10 and 192-E10 are identical to 192-B11 and 192-C10, but comprise slight differences at the 3'-end of 5'-terminal stretch and at the 5'-end of 3'-terminal stretch resulting in reduced binding affinity.

The substitution of 5'- and 3'-terminal nucleotides 'CUGUG' and 'CGCAG' of Type A SDF-1 binding nucleic acid 192-A10-002 by 'GCGCG' and 'CGCGC' (192-A10-015) resulted in a reduced binding affinity whereas substitutions by 'GCGUG' and 'CGCGC' (192-A10-008) resulted in same binding affinity as shown for 192-A10-002 (FIG. 2B). Additionally, nine derivatives of Type A SDF-1 binding nucleic acid 192-A10-001 (192-A10-014/-015/-016/-017/-018/-019/-020/-021/-022/-023) bearing four 5'- and 3'-terminal nucleotides respectively were tested as aptamers for their binding affinity vs. 192-A10-001 or its derivative 192-A10-008 (both have the identical binding affinity to SDF-1). All molecules showed weaker, much weaker or very much weaker binding affinity to SDF-1 as 192-A10-001 (six nucleotides forming a terminal helix) or as 192-A10-008 with five terminal nucleotides, respectively (FIG. 2B). Consequently, the sequence and the number of nucleotides of the 5'- and 3'-terminal stretches are essential for an effective binding to SDF-1. As shown for Type A SDF-1 binding nucleic acids 192-A10-002 and 192-A10-08 the preferred combination of 5'- and 3'-terminal stretches are 'CUGUG' and 'CGCAG' (5'- and 3'-terminal stretches of Type A SDF-1 binding nucleic acid 192-A10-002) and 'GCGUG' and 'CGCGC' (5'- and 3'-terminal stretches of Type A SDF-1 binding nucleic acid 192-A10-008).

However, combining the 5'- and 3'-terminal stretches of all tested Type A SDF-1 binding nucleic acids the generic formula for the 5'-terminal stretch of Type A SDF-1 binding nucleic acids is '$X_1X_2$NNBV' (Type A Formula-7-5') and the generic formula for the 3'-terminal stretch of Type A SDF-1 binding nucleic acids is 'BNBN$X_3X_4$' (Type A Formula-7-3'), whereas $X_1$ is 'R' or absent, $X_2$ is 'S', $X_3$ is 'S' and $X_4$ is 'Y' or absent;

or $X_1$ is absent, $X_2$ is 'S' or absent, $X_3$ is 'S' or absent and $X_4$ is absent.

In order to prolong the Spiegelmer's plasma residence time in vivo, Spiegelmers 192-A10-008 was covalently coupled to a 40 kDa polyethylene glycol (PEG) moiety at the 5'-end as described in chapter 2. The PEG-moiety has no influence on Spiegelmers potency to inhibit SDF-1 induced chemotaxis.

SDF-1 Binding Nucleic Acid Molecules of Type B

As depicted in FIG. 3 all sequences of SDF-1 binding nucleic acids of type B comprise one central stretch of nucleotides which is flanked by 5'- and 3'-terminal stretches (also referred to as first and second terminal stretch of nucleotides) that can hybridize to each other. However, such hybridization is not necessarily given in the molecule.

In the following the terms 'SDF-1 binding nucleic acid molecules of type B' and 'Type B SDF-1 binding nucleic acids' or Type B SDF-1 binding nucleic acid molecules' are used herein in a synonymous manner if not indicated to the contrary.

The sequences of the defined boxes or stretches may be different between the SDF-1 binding nucleic acids which influences the binding affinity to SDF-1. Based on binding analysis of the different SDF-1 binding nucleic acids, the central stretch of nucleotides and its nucleotide sequences as described in the following are individually and more preferably in their entirety essential for binding to SDF-1.

The central stretch of nucleotides of all identified sequences of SDF-1 binding nucleic acids 193-C2-001, 193-G2-001, 193-F2-001, 193-G1-002, 193-D2-002, 193-A1-002, 193-D3-002, 193-B3-002, 193-H3-002, 193-E3-002 and 193-D1-002 share the sequence

GUGUGAUCUAGAUGUADWGGCUGWUCCUAGUYAGG (Type B Formula-1, SEQ ID NO: 52). The SDF-1 binding nucleic acids 193-G2-001, 193-C2-001 and 193-F2-001 that differ in one position of the central stretch of nucleotides (consensus sequence of central stretch of nucleotides:

GUGUGAUCUAGAUGUADUGGCUGAUCCUAGUCAGG (Type B Formula-2, SEQ ID NO: 53) were analyzed in a competitive pull-down binding assay vs. the SDF-1 binding nucleic acid 192-A10-001 ($K_D$ of 1.5 nM determined in a pull-down binding assay, $IC_{50}$ of 0.12 nM). Each of the SDF-1 binding nucleic acids 193-G2-001, 193-C2-001 and 193-F2 showed superior binding to human SDF-1 in comparison to SDF-1 binding nucleic acid 192-A10-001 whereby the binding affinity of 193-G2-001 is as good as 193-C2-001 and 193-F2-001 (FIG. 3). The data suggests that the difference in the nucleotide sequence of the central stretch of nucleotides of SDF-1 binding nucleic acids 193-G2-001, 193-C2-001 and 193-F2-001 has no influence on the binding affinity to SDF-1. The SDF-1 binding nucleic acids 193-G1-002, 193-D2-002, 193-A1-002, 193-D3-002, 193-B3-002, 193-H3-002, 193-E3-002 and 193-D1-002 showed reduced binding to human SDF-1 in comparison to SDF-1 binding nucleic acid 193-G2-001. SDF-1 binding nucleic acid 193-G2-001 was characterized for its binding affinity to human SDF-1. The equilibrium binding constant $K_D$ was determined using the pull-down binding assay ($K_D$=0.3 nM). The $IC_{50}$ (inhibitory concentration 50%) of 0.08 nM for 193-G2-001 was measured using a cell culture in vitro chemotaxis assay.

Four, five or six nucleotides out of the six nucleotides of the 5'-terminal stretch of SDF-1 binding nucleic acids may hybridize to the respective four, five or six out of the six nucleotides of the 3'-terminal stretch of SDF-1 binding nucleic acids to form a terminal helix. Although the nucleotides are variable at several positions, the different nucleotides allow the hybridization for four, five or six nucleotides out of the six nucleotides of the 5'- and 3'-terminal stretches each. The 5'-terminal and 3'-terminal stretches of SDF-1 binding nucleic acids as shown in FIG. 3 can be summarized in a generic formula for the 5'-terminal stretch ('$X_1X_2$GCRWG' whereas $X_1$ is 'A' or absent, $X_2$ is 'G') and of the 3'-terminal stretch ('KRYSC$X_3X_4$' whereas $X_3$ is 'G', $X_4$ is 'U' or absent). SDF-1 binding nucleic acids 193-G1-002, 193-D2-002, 193-A1-002 and 193-D3-002 have weaker binding affinities to SDF-1 although they share the identical central stretch of nucleotides with 193-C2-001, 193-G2-001 and 193-F2-001 (FIG. 3). The unfavorable binding properties of SDF-1 binding nucleic acids 193-G1-002, 193-D2-002, 193-A1-002 and 193-D3-002 may be due to the number of nucleotides and sequence of the 5'- and 3'-terminal stretches.

Truncated derivatives of the SDF-1 binding nucleic acids 193-G2-001 and 193-C2-001 were analyzed in a competitive pull-down binding assay vs. 193-G2-001 and 193-G2-012, respectively (FIGS. 4A and 4B). These experiments showed that a reduction of the six terminal nucleotides (5'end: AGCGUG; 3'end: UACGCU) of SDF-1 binding nucleic acids 193-G2-001 and 193-C2-001 to five nucleotides (5'end: GCGUG; 3'end: UACGC) lead to molecules with similar binding affinity (193-C2-002 and 193-G2-012). The equilibrium dissociation constant $K_D$ was determined using the pull-down binding assay ($K_D$=0.3 nM). A truncation to four (5'end: CGUG; 3'end: UACG; 193-C2-003) or less nucleotides (193-C2-004, 193-C2-005, 193-C2-006, 193-C2-007) resulted in a reduced binding affinity to SDF-1 which was measured by using the competition pull-down binding assay (FIG. 4A). The nucleotide sequence of the five terminal nucleotides at the 5'- and 3'-end, respectively, has an influence on the binding affinity of SDF-1 binding nucleic acids. The substitution of 5'- and 3'-terminal nucleotides 'GCGUG' and 'UACGC' (193-C2-002, 193-G2-12) by 'GCGCG' and 'CGCGC' (193-G2-013) resulted in a reduced binding affinity. Additionally, the four different derivatives of SDF-1 binding nucleic acid 193-G2-001 with a terminal helix with a length of four base-pairing nucleotides (193-G2-014/-015/-016/-017) were tested. All of them showed reduced binding affinity to SDF-1 (FIG. 4B). Therefore the sequence and the length of the 5'- and 3'-terminal nucleotides are essential for an effective binding to SDF-1. The 5'-terminal and 3'-terminal stretches with a length of five and four nucleotides of the derivatives of SDF-1 binding nucleic acids 193-C2-003 and 193-G2-012 as shown in FIGS. 4A and 4B can be described in a generic formula for the 5'-terminal stretch ('$X_1X_2$SSBS'), whereby $X_1$ is absent, $X_2$ is either absent or is 'G', and of the 3'-terminal stretch ('BVSS$X_3X_4$'), and whereby $X_3$ is either absent or is 'C' and $X_4$ is absent. As shown for SDF-1 binding nucleic acids 193-G2-001 and 193-C2-01 and their derivatives 193-G2-012 and 193-C2-002 the preferred combination of 5'- and 3'-terminal stretches are '$X_1X_2$GCGUG' (5'-terminal stretch) and 'UACGC$X_3X_4$' (3'-terminal stretch), whereas $X_1$ is either 'A' or absent, $X_2$ is 'G' and $X_3$ is 'C' and '$X_4$ is 'U' or absent.

However, combining the 5'- and 3'-terminal stretches of all tested SDF-1 binding nucleic acids the generic formula for the 5'-terminal stretch of SDF-1 binding nucleic acids is '$X_1X_2$SVNS' and the generic formula for the 3'-terminal stretch SDF-1 binding nucleic acids is 'BVBS$X_3X_4$', whereas $X_1$ is 'A' or absent, $X_2$ is 'G', $X_3$ is 'C' and $X_4$ is 'U' or absent;

or $X_1$ is absent, $X_2$ is 'G' or absent, $X_3$ is 'C' or absent and $X_4$ is absent.

In order to prolong the Spiegelmer's plasma residence time in vivo, Spiegelmers 193-G2-012 was covalently coupled to a 40 kDa polyethylene glycol (PEG) moiety at the 5'-end as described in chapter 2 (PEGylated-nucleic acid molecule: 193-G2-012-5'-PEG also referred to as NOX-A12). The PEGylated Spiegelmer NOX-A12 was analyzed in cell culture in an in vitro chemotaxis-assay and an inhibition of SDF-1 induced chemotaxis was determined ($IC_{50}$ of 0.2 nM). The PEGylated Spiegelmer NOX-A12 was analyzed by Biacore measurement and a binding constant ($K_D$) of 0.2 nM was determined.

SDF-1 Binding Nucleic Acid Molecules of Type C

As depicted in FIG. 12 all sequences of SDF-1 binding nucleic acids of type C comprise one central stretch of nucleotides which is flanked by 5'- and 3'-terminal stretches (also referred to as first terminal stretch and second terminal stretch of nucleotides) that can hybridize to each other. However, such hybridization is not necessarily given in the molecule.

In the following the terms 'SDF-1 binding nucleic acid molecules of type C' and 'Type C SDF-1 binding nucleic acids' or Type C SDF-1 binding nucleic acid molecules' are used herein in a synonymous manner if not indicated to the contrary.

The sequences of the defined boxes or stretches may be different between the SDF-1 binding nucleic acids of Type C which influences the binding affinity to SDF-1. Based on binding analysis of the different SDF-1 binding nucleic acids summarized as Type C SDF-1 binding nucleic acids, the central stretch of nucleotides and its nucleotide sequence as described in the following are individually and more preferably in their entirety essential for binding to SDF-1.

The central stretch of nucleotides of all identified sequences of Type C SDF-1 binding nucleic acids share the sequence

GGUYAGGGCUHR$X_A$AGUCGG (Type C Formula-1, SEQ ID NO: 108), whereby $X_A$ is either absent or is 'A'. With the exception of Type C SDF-1 binding nucleic acid 197-D1 the central stretch of nucleotides of all identified sequences of Type C SDF-1 binding nucleic acids share the nucleotide sequence

GGUYAGGGCUHRAAGUCGG (Type C Formula-2, SEQ ID NO: 109). Type C SDF-1 binding nucleic acid 197-D1 (central stretch of nucleotides:

GGUUAGGGCUAA-AGUCGG (SEQ ID NO: 56) missing one nucleotide 'A' within the central stretch of nucleotides and still binding to SDF-1 let conclude an alternative central stretch of nucleotides (GGUYAGGGCUHR-AGUCGG, Type C Formula-3, SEQ ID NO: 110). Initially, all Type C SDF-1 binding nucleic acids as depicted in FIG. 5 were analyzed in a competitive pull-down binding assay vs. Type A SDF-1 binding nucleic acid 192-A10-001 ($K_D$=1.5 nM determined by pull-down assay and by surface plasmon resonance measurements; $IC_{50}$=0.12 nM). The Type C SDF-1 binding nucleic acids 191-D5-001, 197-B2, 190-A3-001, 197-H1, 197-H3 and 197-E3 showed weaker binding affinities than 192-A10-001 in competition experiments. Much weaker binding affinity was determined for 191-A5, 197-B1, 197-D1, 197-H2 and 197-D2 (FIG. 5). The molecules or derivatives thereof were further characterized by further competitive pull-down binding assays, plasmon resonance measurements and an in vitro chemotaxis assay. The Type C SDF-1 binding nucleic acid 191-D5-001 was characterized for its binding affinity to human SDF-1 whereas the equilibrium binding constant $K_D$ was determined by surface plasmon resonance measurement ($K_D$=0.8 nM). The $IC_{50}$ (inhibitory concentration 50%) of 0.2 nM for 191-D5-001 was measured using a cell-culture in vitro chemotaxis assay. The binding affinity of Type C SDF-1 binding nucleic acid 197-B2 for human SDF-1 was determined by surface plasmon resonance measurement ($K_D$=0.9 nM), its $IC_{50}$ (inhibitory concentration 50%) of 0.2 nM was analyzed in a cell-culture in vitro chemotaxis assay. These data indicates that Type C SDF-1 binding nucleic acids 191-D5-001 and 197-B2 have the similar binding affinity to SDF-1 (FIGS. 5 and 8).

Type C SDF-1 binding nucleic acid 190-A3-001 comprises a 5'-terminal stretch of 17 nucleotides ('CGUGCGC-UUGAGAUAGG', SEQ ID NO: 220) and a 3'-terminal stretch of 12 nucleotides ('CUGAUUCUCACG', SEQ ID NO: 221) whereby on the one hand the four nucleotides at the 5'-end of the 5'-terminal stretch and the four nucleotides at the 3'-end of the 3'-terminal stretch may hybridize to each other to form a terminal helix. Alternatively the nucleotides 'UGAGA' in the 5'-terminal stretch may hybridize to the nucleotides 'UCUCA' in the 3'-terminal stretch to form a terminal helix. A reduction to nine nucleotides of the 5'-terminal stretch ('UGAGAUAGG') and to ten ('CUGAUU-CUCA', SEQ ID NO: 222) nucleotides of the 3'-terminal stretch ('CUGAUUCUC') of molecule 190-A3-001 does not have an influence on the binding affinity to SDF-1 (190-A3-003; FIG. 13). A reduction to eight nucleotides of the 5'-terminal stretch ('GAGAUAGG') and to nine nucleotides of the 3'-terminal stretch ('CUGAUUCUC') of molecule 190-A3-001 does not have an influence on the binding affinity to SDF-1 (190-A3-004; FIG. 6). The equilibrium binding constant $K_D$ of 190-A3-004 was determined using the pull-down binding assay ($K_D$=4.6 nM) and by surface plasmon resonance measurement ($K_D$=4.7 nM). The $IC_{50}$ (inhibitory concentration 50%) of 0.1 nM for 190-A3-004 was measured using a cell-culture in vitro chemotaxis assay. However, the truncation to two nucleotides at the 5'-terminal stretch leads to a very strong reduction of binding affinity (190-A3-007; FIG. 6).

The Type C SDF-1 binding nucleic acids 191-D5-001, 197-B2 and 197-H1 (central stretch of nucleotides:

GGUUAGGGCUAGAAGUCGG,

SEQ ID 57, 197-H3/191-A5 (central stretch of nucleotides:

GGUUAGGGCUCGAAGUCGG,

SEQ ID NO: 58 and 197-E3/197-B1 (central stretch of nucleotides:

GGUUAGGGCUUGAAGUCGG,

SEQ ID NO: 59 share an almost identical central stretch of nucleotides (Type C formula-4; nucleotide sequence:

GGUUAGGGCUHGAAGUCGG

SEQ ID NO: 111). 191-D5-001, 197-B2 and 197-H1 do not share a similar 5'- and 3'-terminal stretch (197-H3 and 197-E3 have the identical 5'- and 3'-terminal stretch as 197-B2). However, the respective ten (197-B2, 197-E3, 197-H3) or nine out of the ten (191-D5-001, 197-H1) nucleotides of the 5'-terminal stretch may hybridize to the respective ten (197-B2, 197-E3, 197-H3) or nine out of the ten (191-D5-001, 197-H1) nucleotides of the 3'-terminal stretch (FIG. 5). Thus, the 5'-terminal stretch of Type C SDF-1 binding nucleic acids 197-B2, 191-D5-001, 197-H1, 197-E3 and 197-H3 as mentioned above plus 191-A5, 197-B1, 197-H2, 197-D1 and 197-D2 comprise a common generic nucleotide sequence of 'RKSBUSNVGR' (Type C Formula-5-5', SEQ ID NO: 138). The 3'-terminal stretch of Type C SDF-1 binding nucleic acids 197-B2, 191-D5-001, 197-H1, 197-E3, and 197-H3 as mentioned above plus 191-A5, 197-B1, 197-H2, 197-D1 and 197-D2 comprise a common generic nucleotide sequence of 'YYNRCASSMY' (Type C Formula-5-3', SEQ ID NO: 139), whereby the 5' and the 3'-terminal stretches of Type C SDF-1 binding nucleic acids 197-B2, 191-D5-001, 197-H1, 197-E3 and 197-H3 are preferred. These preferred 5'- and and 3'-terminal stretches of Type C SDF-1 binding nucleic acids 197-B2, 191-D5-001, 197-H1, 197-E3 and 197-H3 can be summarized in the generic formula 'RKSBUGSVGR' (Type C Formula-6-5'; 5'-terminal stretch, SEQ ID NO: 140) and 'YCNRCASSMY' (Type C Formula-6-3'; 3'-terminal stretch, SEQ ID NO: 141).

Truncated derivatives of Type C SDF-1 binding nucleic acid 191-D5-001 were constructed and tested in a competitive pull-down binding assay vs. the original molecule 191-D5-001 (FIG. 7A, FIG. 7B). At first the length of the 5'- and 3'-terminal stretches were shortened from ten nucleotides (191-D5-001) each to seven nucleotides each (191-D5-004) as depicted in FIG. 14A whereby nine out of the ten (191-D5-001) or six out of the seven nucleotides (191-D5-004) of the 5'-terminal stretch and of the 3'-terminal stretch, respectively can hybridize to each other. The reduction to seven nucleotides of the 5'- and 3'-terminal stretch respectively (whereas six out of the seven nucleotides can hybridize to each other) led to reduced binding affinity to SDF-1 (191-D5-004). The terminal stretches of Type C SDF-1 binding nucleic acid 191-D5-004 were modified whereby the non-pairing nucleotide 'A' within the 3'-terminal stretch of 191-D5-004 was substituted by a 'C' (191-D5-005). This modification led to an improvement of binding. This derivative, Type C SDF-1 binding nucleic acid 191-D5-005, showed similar binding to SDF-1 as 191-D5-001. Further truncation of the 5'- and 3'-terminal stretch to five nucleotides respectively led to a molecule with a length of total 29 nucleotides (191-D5-007). Because of the similarities of 191-D5-001 and of the Type C SDF-1 binding nucleic acids 197-B2, 191-D5-001, 197-H1, 191-A5, 197-H3, 197-B1, 197-E3, 197-D1, 197-H2 and 197-D2 and because of the data shown for 191-D5-007 it may assume that the 5'- and 3'-terminal stretch can in principle be truncated down to five nucleotides whereby the nucleotide sequence 'CGGGA' for 5'-terminal stretch and 'UCCCG' for the 3'-terminal stretch was successfully tested (Type C SDF-1 binding nucleic acid 191-D5-007). Type C SDF-1 binding nucleic acid 191-D5-007 surprisingly binds somewhat better to SDF-1 than 191-D5-001 (determined on aptamer level using the competition binding assay). The equilibrium binding constant $K_D$ of 191-D5-007 was determined using the pull-down binding assay ($K_D$=2.2 nM) and by surface plasmon resonance measurement ($K_D$=0.8 nM). The $IC_{50}$ (inhibitory concentration 50%) of 0.1 nM for 191-D5-007 was measured using a cell-culture in vitro chemotaxis assay. Further truncation of both terminal stretches to four nucleotides (191-D5-010, FIG. 7A).

Further derivatives of Type C SDF-1 binding nucleic acid 191-D5-001 (191-D5-017/-024/-029) bearing 5'- and 3'-terminal stretches of respectively four nucleotides also showed reduced binding affinity to SDF-1 in the competition pull-down binding assay vs. 191-D5-007 (FIG. 7B). Alternative 5'- and 3'-terminal stretches with a length of respectively five nucleotides were additionally tested, too (191-D5-017-29a, 191-D5-017-29b, 191-D5-019-29a, 191-D5-024-29a, 191-D5-024-29b). The generic formula of these derivatives for the 5'-terminal stretch is '$X_s$SSSV' (Type C Formula-7-5') and for the 3'-stretch is 'BSSS$X_s$' Type C Formula-7-3'), whereby Xs is absent or, S'. Two out of the five tested variants showed identical binding affinity to SDF-1 as 191-D5-007 (191-D5-024-29a, 191-D5-024-29b; FIG. 7B). The sequences of the 5'-terminal and 3'-terminal stretches of 191-D5-001-derivatives that show the best binding affinity to SDF-1 and comprise a 5'-terminal and 3'-terminal stretch of five nucleotides respectively (191-D5-007, 191-D5-024-29a, 191-D5-024-29b) can be summarized in a generic formula (5'-terminal stretch: 'SGGSR', Type C Formula-8-5'; 3'-terminal stretch: 'YSCCS', Type C Formula-8-3').

Truncated derivatives of Type C SDF-1 binding nucleic acid 197-B2 were analyzed in a competitive pull-down binding assay vs. the original molecule 197-B2 and 191-D5-007 (FIG. 7). Using the competitive pull-down binding assay vs. 191-D5-007 it was shown that 197-B2 has the same binding affinity to SDF-1 as 191-D5-007. The 5'- and 3'-terminal stretches were shortened without loss of binding affinity from ten nucleotides (197-B2) each to five nucleotides each (197-B2-005) whereby the nucleotides of the 5'-terminal stretch and of the 3'-terminal stretch can completely hybridize to each other. If the 5'-terminal ('GCGGG') and 3'-terminal ('CCUGC') stretch of 197-B2-

005 was substituted by 'GCCGG' (5'-terminal stretch) and by 'CCGGC' (3'-terminal stretch) of 197-B2-006, the binding affinity to SDF-1 fully persisted. Because 197-B2 and 191-D5-001 (and their derivatives) share the identical core nucleotide sequence and several derivatives of 191-D5 with 5'- and 3'-terminal stretches with a length of respectively four nucleotides were tested, a further truncation of the 5'- and 3'-terminal stretch was omitted. Two further derivatives were designed that comprise six nucleotides at the 5'- and 3'-end (5'- and 3'-terminal stretches) respectively. The binding affinity to SDF-1 of both molecules (197-B2-006-31a and 197-B2-006-31b) is the same as shown for 191-D5-007 and 197-B2-006 (FIG. 15). The sequences of the 5'-terminal and 3'-terminal stretches of 197-B2 derivatives that show the best binding affinity to SDF-1 and comprise a 5'-terminal and 3'-terminal stretch of five nucleotides respectively can be summarized in a generic formula (5'-terminal stretch: 'GCSGG', Type C Formula-9-5'; 3'-terminal stretch: CCKGC', Type C Formula-9-3').

Combining the preferred 5'- and 3'-stretches of truncated derivatives of Type C SDF-1 binding nucleic acids 191-D5-001 (5'-terminal stretch: 'SGGSR', Type C Formula-8-5'; 3'-terminal stretch: 'YSCCS', Type C Formula-8-3') and 197-B2 (5'-terminal stretch: 'GCSGG', Type C Formula-9-5'; 3'-terminal stretch: CCKGC', Type C Formula-9-3') the common preferred generic formula for the 5'-terminal and the 3'-terminal stretch is 'SSSSR' (5'-terminal stretch, Type C Formula-10-5') and 'YSBSS' (3'-terminal stretch: Type C Formula-10-3').

In order to prolong the Spiegelmer's plasma residence time in vivo, Spiegelmers 197-B2-006 and 191-D5-007 were covalently coupled to a 40 kDa polyethylene glycol (PEG) moiety at their 5'-ends as described in chapter 2. The PEGylated Spiegelmers 197-B2-006 and 191-D5-007 were analyzed in cell culture in an in vitro chemotaxis. The PEG-moiety has no influence on Spiegelmers potency to inhibit SDF-1 induced chemotaxis.

SDF-1 Binding Nucleic Acid Molecules of Type D

Additionally, further three SDF-1 binding nucleic acids that do not share the SDF-1 binding motifs of 'Type A', 'Type B' and 'Type C' were identified and are referred to herein as "type D". There were analyzed as aptamers using the pull-down binding assay (FIG. 9).

It is to be understood that any of the sequences shown in FIGS. 1 through 9 are nucleic acid molecules according to the present invention, including those truncated forms thereof but also including those extended forms thereof under the proviso, however, that the thus truncated and extended, respectively, nucleic acid molecules are still capable of binding to the target.

EXAMPLE 2

Synthesis and Derivatization of Aptamers and Spiegelmers

Small Scale Synthesis

Aptamers and Spiegelmers were produced by solid-phase synthesis with an ABI 394 synthesizer (Applied Biosystems, Foster City, Calif., USA) using 2'TBDMS RNA phosphoramidite chemistry (Damha and Ogilvie, 1993). rA(N-Bz)-, rC(Ac)-, rG(N-ibu)-, and rU-phosphoramidites in the D- and L-configuration were purchased from ChemGenes, Wilmington, Mass. Aptamers and Spiegelmers were purified by gel electrophoresis.

Large Scale Synthesis Plus Modification

The Spiegelmers were produced by solid-phase synthesis with an ÄktaPilot100 synthesizer (Amersham Biosciences; General Electric Healthcare, Freiburg) using 2'TBDMS RNA phosphoramidite chemistry (Damha and Ogilvie, 1993). L-rA(N-Bz)-, L-rC(Ac)-, L-rG(N-ibu)-, and L-rU-phosphoramidites were purchased from ChemGenes (Wilmington, Mass., USA). The 5'-amino-modifier was purchased from American International Chemicals Inc. (Framingham, Mass., USA). Synthesis of the Spiegelmers was started on L-riboG; L-riboC, L-riboA, L-riboU respectively modified CPG pore size 1000 Å (Link Technology, Glasgow, UK). For coupling (15 min per cycle), 0.3 M benzylthiotetrazole (American International Chemicals Inc., Framingham, Mass., USA) in acetonitrile, and 3.5 equivalents of the respective 0.2 M phosphoramidite solution in acetonitrile was used. An oxidation-capping cycle was used. Further standard solvents and reagents for oligonucleotide synthesis were purchased from Biosolve (Valkenswaard, NL). The Spiegelmers were synthesized DMT-ON; after deprotection, it was purified via preparative RP-HPLC (Wincott F. et al., 1995) using Source 15RPC medium (Amersham). The 5'DMT-group was removed with 80% acetic acid (90 min at RT). Subsequently, aqueous 2 M NaOAc solution was added and the Spiegelmer was desalted by tangential-flow filtration using a 5 K regenerated cellulose membrane (Millipore, Bedford, Mass.).

Pegylation

In order to prolong the Spiegelmer's plasma residence time in vivo, the Spiegelmers were covalently coupled to a 40 kDa polyethylene glycol (PEG) moiety at the 5'-end.

For PEGylation (for technical details of the method for PEGylation see European patent application EP 1 306 382), the purified 5'-amino modified Spiegelmerd were dissolved in a mixture of $H_2O$ (2.5 ml), DMF (5 ml), and buffer A (5 ml; prepared by mixing citric acid • $H_2O$ [7 g], boric acid [3.54 g], phosphoric acid [2.26 ml], and 1 M NaOH [343 ml] and adding water to a final volume of 1 l; pH=8.4 was adjusted with 1 M HCl).

The pH of the Spiegelmer solution was brought to 8.4 with 1 M NaOH. Then, 40 kDa PEG-NHS ester (JenKem Technology USA Inc., Allen, Tex.) was added at 37° C. every 30 min in six portions of 0.25 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), and 4 ml buffer B (0.1 M triethylammonium acetate in $H_2O$) and heated to 95° C. for 15 min. The PEGylated Spiegelmer was then purified by RP-HPLC with Source 15RPC medium (Amersham), using an acetonitrile gradient (buffer B; buffer C: 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAC. The PEGylated Spiegelmer was desalted by tangential-flow filtration (5 K regenerated cellulose membrane, Millipore, Bedford Mass.).

EXAMPLE 3

Determination of Binding Constants (Pull-Down Binding Assay)

Direct Pull-Down Binding Assay

The affinity of aptamers to biotinlayted human D-SDF-1 was measured in a pull-down binding assay format at 37° C. Aptamers were 5'-phosphate labeled by T4 polynucleotide kinase (Invitrogen, Karlsruhe, Germany) using [$\gamma$-$^{32}$P]-labeled ATP (Hartmann Analytic, Braunschweig, Germany). The specific radioactivity of labeled aptamers was 200,000-800,000 cpm/pmol. Aptamers were incubated after de- and renaturation at 10, 20, 30 or 40 pM concentration at 37° C. in selection buffer (20 mM Tris-HCl pH 7.4; 137 mM NaCl; 5 mM KCl; 1 mM $MgCl_2$; 1 mM $CaCl_2$; 0.1% [w/vol] Tween-20) together with varying amounts of biotinlayted human D-SDF-1 for 4-12 hours in order to reach equilibrium at low concentrations. Selection buffer was supplemented with 10 μg/ml human serum albumin (Sigma-Aldrich, Steinheim, Germany), and 10 μg/ml yeast RNA (Ambion, Austin, USA) in order to prevent adsorption of binding partners with surfaces of used plasticware or the immobilization matrix. The concentration range of biotinlayted human D-SDF-1 was set from 8 pM to 100 nM; total reaction volume was 1 ml. Peptide and peptide-aptamer complexes were immobilized on 1.5 μl Streptavidin Ultralink Plus particles (Pierce Biotechnology, Rockford, USA) which had been preequilibrated with selection buffer and resuspended in a total volume of 6 μl. Particles were kept in suspension for 30 min at the respective temperature in a thermomixer. Immobilized radioactivity was quantitated in a scintillation counter after detaching the supernatant and appropriate washing. The percentage of binding was plotted against the concentration of biotinlayted human D-SDF-1 and dissociation constants were obtained by using software algorithms (GRAFIT; Erithacus Software; Surrey U.K.) assuming a 1:1 stoichiometry.

Competitive Pull-Down Binding Assay

In order to compare different D-SDF-1 binding aptamers, a competitive ranking assay was performed. For this purpose the most affine aptamer available was radioactively labeled (see above) and served as reference. After de- and renaturation it was incubated at 37° C. with biotinlayted human D-1 in 1 ml selection buffer at conditions that resulted in around 5-10% binding to the peptide after immobilization and washing on NeutrAvidin agarose or Streptavidin Ultralink Plus (both from Pierce) without competition. An excess of de- and renatured non-labeled D-RNA aptamer variants was added to different concentrations (e.g. 2, 10, and 50 nM) with the labeled reference aptamer to parallel binding reactions. The aptamers to be tested competed with the reference aptamer for target binding, thus decreasing the binding signal in dependence of their binding characteristics. The aptamer that was found most active in this assay could then serve as a new reference for comparative analysis of further aptamer variants.

EXAMPLE 4

Binding Analysis by Surface Plasmon Resonance Measurement

The Biacore 2000 instrument (Biacore AB, Uppsala, Sweden) was used to analyze binding of Spiegelmers to human SDF-1α. When coupling of human SDF-1α was to be achieved via amine groups, human SDF-1α was dialyzed against water for 1-2 h (Millipore VSWP mixed cellulose esters; pore size, 0.025 μM) to remove interfering amines. CM4 sensor chips (Biacore AB, Uppsala, Sweden) were activated before protein coupling by a 35-μl injection of a 1:1 dilution of 0.4 M NHS and 0.1 M EDC at a flow of 5 μi/min. Human MCP-1 or human SDF-1α was then injected in concentrations of 0.1-1.5 μg/ml at a flow of 2 μl/min until the instrument's response was in the range of 1000-2000 RU (relative units). Unreacted NHS esters were deactivated by injection of 35 μl ethanolamine hydrochloride solution (pH 8.5) at a flow of 5 μl/min. The sensor chip was primed twice with binding buffer and equilibrated at 10 μl/min for 1-2 hours until the baseline appeared stable. For all proteins, kinetic parameters and dissociation constants were evaluated by a series of Spiegelmer injections at concentrations of 1000, 500, 250, 125, 62.5, 31.25, and 0 nM in selection buffer (Tris-HCl, 20 mM; NaCl, 137 mM; KCl, 5 mM; $CaCl_2$, 1 mM; $MgCl_2$, 1 mM; Tween20, 0.1% [w/v]; pH 7.4). In all experiments, the analysis was performed at 37° C. using the Kinject command defining an association time of 180 and a dissociation time of 360 seconds at a flow of 10 μl/min. Data analysis and calculation of dissociation constants ($K_D$) was done with the BIAevaluation 3.0 software (BIACORE AB, Uppsala, Sweden) using the Langmuir 1:1 stochiometric fitting algorithm.

EXAMPLE 5

Analysis of the Inhibition of SDF-1-Induced Chemotaxis by SDF-1-Binding Spiegelmers The human T cell leukemia cell line Jurkat, the human leukemic monocyte lymphoma cell line U937, the human pre-B cell leukemia cell line BV-173 and human pre-B ALL cell line Nalm-6 express CXCR4. While Jurkat cells do not express CXCR7, the leukemia lines BV-173 and U-937 were tested positive for CXCR7 expression. All cells used were obtained from the DSMZ (Braunschweig). All cell lines were cultivated at 37° C. and 5% CO2 in RPMI 1640 medium with Glutamax (Invitrogen, Karlsruhe, Germany) which contains 10% fetal bovine serum, 100 units/ml penicillin and 100 μg/ml streptomycin (Invitrogen, Karlsruhe, Germany). One day before the experiment, cells were seeded in a new T175 flask with a density of $0.3 \times 10^6$/ml (Jurkat, U937, BV-173) or $0.75 \leq 10^6$/ml (Nalm-6), respectively.

For the experiment, cells were centrifuged (5 min at 300 g), resuspended, counted and washed once with 15 ml HBH (Hanks balanced salt solution containing 1 mg/ml bovine serum albumin and 20 mM HEPES; Invitrogen, Karlsruhe, Germany). Then the cells were resuspended at $1.33 \times 10^6$/ml (Jurkat, U937, BV-173) or $2.67 \times 10^6$/ml (Nalm-6), respectively. Cells were then allowed to migrate through the porous membranes of the filter plates for three hours towards a solution containing SDF-1 and various amounts of Spiegelmer. The stimulation solutions (SDF-1+various concentrations of Spiegelmer) were made up as 10× solutions in a 0.2 ml low profile 96-tube plate. 212 μl HBH were pipetted into the lower compartments of the transport plate and 23.5 μl of the stimulation solutions were added. All conditions were made up as triplicates. After 20 to 30 min the filter plate was inserted into the plate containing the stimulation solutions and 75 μl of a cell suspension with $1.33 \times 10^6$/ml or $2.67 \times 10^6$/ml, respectively, were added to the wells of the filter plate ($1 \times 10^5$ or $2 \times 10^5$ cells/well). The cells were then allowed to migrate for 3 h at 37° C. For calibration, 0, 10 and 30 μl of the cell suspension was added to 235, 225 and 205 μl HBH, respectively, in wells of a separate 96-well plate. After 3 hours incubation, the insert plate was removed and 30 μl resazurin working solution (440 μM in PBS) were added to the lower wells and to the wells of the calibration plate. The plates were then incubated at 37° C. for 2.5 h. After incubation, 100 μl of each well were transferred to a black 96 well plate.

For evaluation, fluorescence values were corrected for background fluorescence (no cells in well). Then the difference between experimental conditions with and without SDF-1 was calculated. The value for the sample without Spiegelmer (SDF-1 only) was set 100% and the values for the samples with Spiegelmer were calculated as percent of this. For a dose-response curve the percent-values were plotted against Spiegelmer concentration and the $IC_{50}$-value (concentration of Spiegelmer at which 50% of the activity without Spiegelmer is present) was determined graphically from the resulting curve.

Results

Human SDF-1 was found to stimulate migration of Jurkat cells in a dose dependent manner, with half-maximal stimulation at about 0.3 nM.

Human SDF-1 was found to stimulate migration of cells of the human leukemic monocyte lymphoma cell line U937 in a dose dependent manner, with half-maximal stimulation at about 3 nM.

Human SDF-1 was found to stimulate migration of cells of the human pre-B cell leukemia cell line BV-173 in a dose dependent manner, with half-maximal stimulation at about 3 nM.

Human SDF-1 was found to stimulate migration of cells of the human pre-B ALL cell line Nalm-6 in a dose dependent manner, with half-maximal stimulation at about 0.3 nM.

When cells were allowed to migrate towards a solution containing human SDF-1 plus increasing concentrations of SDF-1 binding Spiegelmers, dose-dependent inhibition was observed. The respective IC50s of the tested Spiegelmers as specified in Example 1 were determined in human T cell leukemia cell line Jurkat cells. For example, for SDF-1 binding Spiegelmer NOX-A12 (also referred to as 193-G2-012-5'-PEG) an IC50 of 0.2 nM was determined (FIG. 10). When an unspecific Control Spiegelmer was used instead of SDF-1 binding Spiegelmers, no inhibitory effect was observed up to 1 μM.

Inhibition of the SDF-1 induced chemotaxis by SDF-1 binding spiegelmer NOX-A12 was also observed in three other different leukemia cell types: the human leukemic monocyte lymphoma cell line U937 (FIG. 11B), the human pre-B cell leukemia cell line BV-173 (FIG. 12) and the human pre-B ALL cell line Nalm-6 (FIG. 11A). Furthermore, the inventors have evidence that primary chronic lymphocytic leukemia cells migrate towards SDF-1 and that SDF-1 dependent chemotaxis is effectively blocked by NOX-A12.

The leukemia lines BV-173 and U-937 were tested positive also for CXCR7 expression. The potency of SDF-binding spiegelmer NOX-A12 to block interaction of SDF-1 and CXCR7 was determined as shown in Example 6.

EXAMPLE 6

Inhibition of CXCR7 Activation by SDF-1-Binding Spiegelmer NOX-A12

Besides CXCR4, SDF-1 also binds to the chemokine receptor CXCR7. The inhibitory potential of SDF-1-binding Spiegelmer NOX-A12 towards CXCR7 was tested in a complementation assay with CHO cells stably expressing CXCR7 and β-arrestin both fused to a fragment of β-galactosidase (PathHunter™—β-arrestin assay, DiscoveRX, Calif., USA). Upon SDF-1 binding β-arrestin complexed with CXCR7 and thus led to complementation and activation of the β-galactosidase which was measured with a chemiluminescence substrate.

Method

PathHunter eXpress CHO-K1 Human CXCR7 β-arrestin cells were plated for 48 hours in OCC2 Medium and stimulated with 10 nM SDF-1 and various concentrations of SDF-1-binding Spiegelmer NOX-A12 for 90 minutes. Following stimulation, signal was detected using the PathHUnter Detection Kit and the manufacturer's recommended protocol (DiscoveRX, Calif., USA).

Results

Stimulation of β-galactosidase and hence CXCR7 activation with 10 nM human SDF-1 was efficiently blocked by SDF-1-binding Spiegelmer NOX-A12 with an IC50 of 5.4 nM (FIG. 13).

EXAMPLE 7

Spheroid Formation and T Cell Infiltration Shown by Immunohistochemistry

Three-dimensional multicellular microtissues that mimic a CXCL12-expressing solid tumor were established. For this purpose, $2.5\times10^4$ CXCL12-expressing murine stromal MS-5 cells were co-cultured with $0.5\times10^4$ human cancer cells (PSN-1 pancreatic ductal adenocarcinoma, HT-29 colorectal carcinoma) in DMEM+5% fetal bovine serum (FBS) in 96-well ultra-low attachment plates for three days. Primary human T cells ($5\times10^4$/well) isolated from PBMCs of healthy donors (Pan T cell isolation Kit, Miltenyi) were added to the spheroids in the presence or absence of NOX-A12. The next day, spheroids were washed, fixed in neutral buffered formalin (2 h) and paraffin-embedded. 2 μm sections were prepared for H&E- or immuno-staining with antibodies against the following targets: βCXCL12 (mAb350, R&D Systems), αPan cytokeratine, αKi-67, αCD3 and hematoxylin counterstaining for the visualization of nuclei (FIGS. 14, 15). T cells were quantified by counting (2-3 persons).

EXAMPLE 8

NK Cell Infiltration Using Isolated NK Cells as Input

Tumor/stroma microtissues (spheroids) were prepared from PSN-1 cancer cells and MS5 stromal cells as described in Example 7. NK cells were isolated from PBMCs from healthy donors (NK cell isolation kit, Miltenyi). Isolated NK cells ($5\times10^4$/well) were added with various concentrations of NOX-A12 (0-40 nM) to the spheroids. The next day, spheroids were washed and dissociated (Accumax, eBiosciences) for NK cell ($CD3^-CD45^+$) quantification by flow cytometry.

NOX-A12 was found to enhance infiltration of human NK cells isolated from two different healthy donors into tumor-stroma spheroids in a dose-dependent manner (FIG. 16).

NK cell infiltration was further analyzed in four different tumor-stroma spheroid types using the cancer cell lines PSN-1 (pancreatic ductal adenocarcinoma, PDAC), HT-29 (colorectal carcinoma, CRC), H1299 (non-small cell lung cancer, NSCLC) and U251MG (glioblastoma, GBM).

The results are similar to the data shown in FIG. 16. All four spheroid types responded with the same pattern of a dose-dependent increase of NK cell infiltration (FIG. 21).

EXAMPLE 9

Infiltration of NK Cells and Other Cell Types (PBMC or Pan T Cells as Input)

For a more in-depth characterization of immune cell infiltration PSN-1/MS-5 spheroids were generated as described above. PBMCs (A) or Pan T cells (B) from healthy donors were added together with various concentrations of NOX-A12 (0-40 nM) to the spheroids. After dissociation using Accumax, cells were incubated overnight to recover Accumax-labile cell surface molecules for detection by flow cytometry, whereby CD4, CD8, CD25, CD56, CD94 are cleaved by Accumax; CD3, CD14, CD19, CD45 and CD127 are accessible for immediate antibody labeling. Cell types were counted, normalized to the input cell count of each cell type and plotted against NOX-A12 concentration.

NK cell infiltration was found to be enhanced also when PBMC from a human donor were used. Furthermore infiltration of T cells and, to a lesser extent, infiltration of B cells was found to be enhanced by NOX-A12. An analysis of the T cell subset migration showed that NOX-A12 promoted spheroid infiltration by cytotoxic T cells ($CD8^+$) that are besides the NK cells particularly important for anti-tumor defense, as well as helper T cells ($CD4^+$), and, to a lesser extent, regulatory T cells ($CD4^+CD25^+CD127^-$) thereby shifting the balance more into the direction of effector cells (FIG. 17).

EXAMPLE 10

NOX-A12 Enhances T Cell Infiltration in Various Tumor Types

Three dimensional tumor/stroma spheroids were prepared as follows: $2.5\times10^4$ CXCL12-expressing murine stromal MS-5 cells were co-cultured with $0.5\times10^4$ solid human cancer cells (PSN-1 pancreatic ductal adenocarcinoma (PDAC), HT-29 colorectal carcinoma (CRC), H1299 non-small cell lung cancer (NSCLC) and U251MG glioblastoma (GBM)) in DMEM+5% FBS in ultra-low attachment 96-well plates for three days. Primary human T cells ($5\times10^4$/well) isolated from PBMCs of healthy donors (Pan T cell isolation Kit, Miltenyi) were added to the spheroids in the presence or absence of NOX-A12 (0-100 nM). The next day, spheroids were washed and dissociated using Accumax (eBiosciences) for 2 hours for T cell quantification by flow cytometry (antiCD45, clone 2D1, eBiosciences). T cell counts were normalized to the input cell count and plotted against NOX-A12 concentration.

The results show that the pattern of enhanced T cell infiltration that was observed with PSN-1 pancreatic ductal adenocarcinoma cells in Example 7 can be expanded to other cancer entities: Cell lines of colorectal cancer, non-small cell lung cancer and glioblastoma responded with the same pattern of a dose-dependent increase of T cell infiltration. In this experiment the highest concentration of NOX-A12 was 100 nM as opposed to 40 nM in the previous experiments. It becomes apparent that completely neutralizing CXCL12 in the outer margin of the spheroid (around the vessels in a tumor) also blocks the CXCL12 gradient-dependent migration/infiltration (see, FIG. 18).

EXAMPLE 11

NOX-A12 Synergizes with PD-1 Checkpoint Inhibition In Vitro

In order to investigate T cell activation in the spheroids, a reporter-based PD-1/PD-L1 blockade bioassay from Promega was adapted to the 3D format: $Jurkat^{PD-1/luc}$ T cells ($5\times10^4$/well) were incubated with anti-PD-1 (clone PD1.3.1.3, Miltenyi) and added with or without NOX-A12 to tumor-stroma spheroids ($CHO^{PD-L1}$+MS-5; $0.5\times10^4$ $2.5\times10^4$/well, respectively). The next day, T cell infiltration was quantified by flow cytometry as described above. T cell infiltration was also visualized using light microscopy. T cell activation was quantified by incubating the spheroids in 75 μl medium (DMEM+5% FBS) with 50 μL BioGlo substrate (Promega) for 45 min. Baseline activity was set to 0%.

NOX-A12, but not αPD-1 enhanced the infiltration of T cells into the spheroids (see, FIG. 19A). The infiltration was visible under the light microscope by lower numbers of T cells around the spheroid (see, FIG. 19B). NOX-A12 promoted T cell activation, probably by allowing more T cell tumor cell contacts. NOX-A12 without spheroid did not activate T cells (data not shown). The activating effect of NOX-A12 was even stronger than the effect of αPD-1. Also, NOX-A12 was found to synergize with αPD-1 (see, FIG. 19C).

EXAMPLE 12

NOX-A12 Synergizes with PD-1 Checkpoint Inhibition In Vivo

The synergistic effect of NOX-A12 and anti-PD-1 was corroborated in vivo in the syngeneic CT-26 mouse model of undifferentiated, refractory colorectal cancer. The CT-26 model is characterized by poor sensitivity to checkpoint inhibition as monotherapy.

While treatment of the single agents NOX-A12 or anti-PD-1 had no significant effect on tumor growth inhibition, the combination enhanced the efficacy of anti-PD1 treatment with a mean tumor volume reduction by 75% vs. anti-PD-1 monotherapy and by 85% vs. vehicle (see, FIG. 20A). The percentage of mice responding to treatment was increased from 25% (2 out of 8) in the anti-PD1 and 12.5% (1 out of 8) in the NOX-A12 group to 62.5% (5 out of 8) in the combination group (see, FIG. 20B).

EXAMPLE 13

NOX-A12 Synergizes with NK Cell-Mediated ADCC

The inventors established a 3D lymphoid microtissue model mimicking the stroma-rich and CXCL12-abundant TME of lymphoid malignancies in vitro. Using this model NK cell infiltration and Raji lymphoma cell killing in the presence of obinutuzumab and NOX-A12 were studied.

For this purpose, $1.25\times10^4$ CXCL12-expressing murine stromal MS-5 cells (DSMZ) were co-cultured with $0.25\times10^4$ CFSE (Life Technologies)-stained Raji lymphoma cells (ECACC) in DMEM with 5% FBS in ultra-low attachment 96-well plates (Greiner Bio-One, cell repellent surface) for 24 hours. Primary human NK cells ($4\times10^4$/well) isolated from PBMCs of healthy donors (NK cell isolation Kit, Miltenyi) were incubated with various concentrations of rituximab or obinutuzumab and added to the spheroids in the presence or absence of NOX-A12. The next day, spheroids were washed and dissociated using Accumax (eBiosciences) for 90 minutes for NK cell quantification by flow cytometry. NK cell counts were normalized to total cell counts and plotted against NOX-A12 concentration. CFSE-stained Raji cells were counted and live/dead cell discrimination was performed using propidium iodide (Life Technologies).

It was found that NOX-A12 increased the amount of NK cells in the lymphoma-stroma spheroids up to 8-fold in a dose-dependent manner (see, FIG. 22A). The basal NK cell infiltration was quite low with 2-3% of input cells corresponding to 10-15% NK cells relative to total spheroidal cells. This resulted in a weak efficacy of anti-CD20 mAbs obinutzumab and rituximab as monotherapy (see, FIG. 22B). 10 μg/mL obinutuzumab killed 30-40% of Raji cells, while 10 μg/mL rituximab only killed 10%.

NOX-A12-induced infiltration of NK cells alone did not significantly influence the viability of Raji cells. Raising the number of NK cells in the microtissues by 10 nM NOX-A12 enhances the efficacy of both anti-CD20 mAbs in terms of NK cell-mediated killing of lymphoma cells (see, FIG. 22B). A dose-response of obinutuzumab and NOX-A12 allowed to determine a putative synergism of both drugs. Calculation with CompuSyn software based on Chou-Talalay's Combination Index Theorem revealed a combination index of 0.03, indicating a very strong synergistic effect (see, FIG. 22C).

REFERENCES

The complete bibliographic data of the documents recited herein are, if not indicated to the contrary, as follows, whereby the disclosure of said references is incorporated herein by reference.

Alsayed Y., Ngo H., et al. (2007) Mechanisms of regulation of CXCR4/SDF-1 (CXCL12)-dependent migration and homing in multiple myeloma. Blood 109(7): 2708-17.

Altschul S. F., Gish W., et al. (1990) Basic local alignment search tool. J Mol Biol. 215(3):403-10.

Altschul S. F., Madden T. L., et al. (1997) Gapped BLAST and PSI-BLAST: a new generation of protein database search programs. Nucleic Acids Res. 25(17):3389-402.

Arya S. K., Ginsberg C. C., et al. (1999) In vitro phenotype of SDF1 gene mutant that delays the onset of human immunodeficiency virus disease in vivo. J Hum Virol 2(3): 133-8.

Auerbach R., Lewis R., et al. (2003) Angiogenesis assays: a critical overview. Clin Chem. 49(1):32-40. Review.

Azab A. K., Runnels J. M., et al. (2009) CXCR4 inhibitor AMD3100 disrupts the interaction of multiple myeloma cells with the bone marrow microenvironment and enhances their sensitivity to therapy. Blood. 113(18): 4341-51.

Balabanian K., Lagane B., et al. (2005) The chemokine SDF-1/CXCL12 binds to and signals through the orphan receptor RDC1 in T lymphocytes. J Biol Chem 280(42): 35760-35766

Balabanian, K., Lagane B., et al. (2005) WHIM syndromes with different genetic anomalies are accounted for by impaired CXCR4 desensitization to CXCL12. Blood 105 (6): 2449-57.

Balkwill F. (2004) Cancer and the chemokine network. Nat Rev Cancer 4(7): 540-50.

Batchelor T. T., Sorensen A. G., et al. (2007) AZD2171, a pan-VEGF receptor tyrosine kinase inhibitor, normalizes tumor vasculature and alleviates edema in glioblastoma patients. Cancer Cell. 11(1):83-95.

Brahmer, J. R., S. S. Tykodi, L. Q. Chow, W. J. Hwu, S. L. Topalian, P. Hwu, C. G. Drake, L. H. Camacho, J. Kauh, K. Odunsi, H. C. Pitot, O. Hamid, S. Bhatia, R. Martins, K. Eaton, S. Chen, T. M. Salay, S. Alaparthy, J. F. Grosso, A. J. Korman, S. M. Parker, S. Agrawal, S. M. Goldberg, D. M. Pardoll, A. Gupta and J. M. Wigginton (2012). "Safety and activity of anti-PD-L1 antibody in patients with advanced cancer." *N Engl J Med* 366(26): 2455-2465.

Brooks H. L. Jr., Caballero S. Jr., et al. (2004) Vitreous levels of vascular endothelial growth factor and stromal-derived factor 1 in patients with diabetic retinopathy and cystoid macular edema before and after intraocular injection of triamcinolone. Arch Ophthalmol 122(12): 1801-7.

Broxmeyer H. E., Orschell C. M., (2005) Rapid mobilization of murine and human hematopoietic stem and progenitor cells with AMD3100, a CXCR4 antagonist. J Exp Med. 201(8):1307-18.

Buckley C. D., Amft N., et al. (2000) Persistent induction of the chemokine receptor CXCR4 by TGF-beta 1 on synovial T cells contributes to their accumulation within the rheumatoid synovium. J Immunol 165(6): 3423-9.

Burger J. A. and Peled A. (2009) CXCR4 antagonists: targeting the microenvironment in leukemia and other cancers. Leukemia 23(1): 43-52.

Burger J. A., Bürkle A, et al. (2007) The CXCR4 chemokine receptor in acute and chronic leukaemia: a marrow homing receptor and potential therapeutic target. Br J Haematol. 137(4):288-96.

Burger J. A., Ghia P., et al. (2009) The microenvironment in mature B-cell malignancies: a target for new treatment strategies. Blood. 114(16):3367-75. Review Burger J. A., Kipps T. J. et al. (2002) Chemokine receptors and stromal cells in the homing and homeostasis of chronic lymphocytic leukemia B cells. Leuk Lymphoma. 43(3):461-6

Burger J. A., Tsukada N., et al. (2000) Blood-derived nurse-like cells protect chronic lymphocytic leukemia B cells from spontaneous apoptosis through stromal cell-derived factor-1. Blood. 96(8):2655-63.

Burns J. M., Summers B. C., et al. (2006) A novel chemokine receptor for SDF-1 and I-TAC involved in cell survival, cell adhesion, and tumor development. J Exp Med 203(9): 2201-2213

Butler J. M., Guthrie S. M., et al. (2005) SDF-1 is both necessary and sufficient to promote proliferative retinopathy. J Clin Invest 115(1): 86-93

Cabioglu, N., Sahin A., et al. (2005) Chemokine receptor CXCR4 expression in breast cancer as a potential predictive marker of isolated tumor cells in bone marrow. Clin Exp Metastasis 22(1): 39-46.

Ceradini D. J., Kulkarni A. R., et al. (2004) Progenitor cell trafficking is regulated by hypoxic gradients through HIF-1 induction of SDF-1. Nat Med. 10(8):858-64.

Chou, T. C. (2010). "Drug combination studies and their synergy quantification using the Chou-Talalay method." *Cancer Res* 70(2): 440-446.

Clynes R A, Towers T L, Presta L G, Ravetch J V. Inhibitory Fc receptors modulate in vivo cytotoxicity against tumor targets. Nat Med. 2000 April; 6(4):443-6.

Corcione A., Ottonello L., et al. (2000) Stromal cell-derived factor-1 as a chemoattractant for follicular center lymphoma B cells. J Natl Cancer Inst 92(8): 628-35.

Damha M. J., Ogilvie K. K., et al. (1993) Oligoribonucleotide synthesis. The silyl-phosphoramidite method. Methods Mol Biol. 20:81-114.

Damiano J. S., Cress A. E., et al. (1999) Cell adhesion mediated drug resistance (CAM-DR): role of integrins and resistance to apoptosis in human myeloma cell lines. Blood. 93(5):1658-67

Devine S. M., Flomenberg N., et al. (2004) Rapid mobilization of CD34+ cells following administration of the CXCR4 antagonist AMD3100 to patients with multiple myeloma and non-Hodgkin's lymphoma. J Clin Oncol. 22(6):1095-102.

Dillmann F., Veldwijk M. R., et al. (2009) Plerixafor inhibits chemotaxis toward SDF-1 and CXCR4-mediated stroma contact in a dose-dependent manner resulting in increased susceptibility of BCR-ABL+ cell to Imatinib and Nilotinib. Leuk Lymphoma. 50(10):16

Ehtesham M., Stevenson C. B., et al. (2008) Preferential expression of chemokine receptor CXCR4 by highly malignant human gliomas and its association with poor patient survival. Neurosurgery. 63(4):E820

Engl T., Relja B., et al. (2006) CXCR4 chemokine receptor mediates prostate tumor cell adhesion through alpha5 and beta3 integrins. Neoplasia. 8(4):290-301.

Fedyk E. R., Jones D., et al. (2001) Expression of stromal-derived factor-1 is decreased by IL-1 and TNF and in dermal wound healing. J Immunol. 166(9):5749-54.

Fridman, W. H., F. Pages, C. Sautes-Fridman and J. Galon (2012). "The immune contexture in human tumours: impact on clinical outcome." *Nat Rev Cancer* 12(4): 298-306.

Geminder H., Sagi-Assif O., et al. (2001) A possible role for CXCR4 and its ligand, the CXC chemokine stromal cell-derived factor-1, in the development of bone marrow metastases in neuroblastoma. J Immunol 167(8): 4747-57.

Grassi F., Cristino S., et al. (2004) CXCL12 chemokine up-regulates bone resorption and MMP-9 release by human osteoclasts: CXCL12 levels are increased in synovial and bone tissue of rheumatoid arthritis patients. J Cell Physiol 199(2): 244-51.

Grunewald M., Avraham I., et al. (2006) VEGF-induced adult neovascularization: recruitment, retention, and role of accessory cells. Cell 124(1): 175-89.

Gulino, A. V., Moratto D., et al. (2004) Altered leukocyte response to CXCL12 in patients with warts hypogammaglobulinemia, infections, myelokathexis (WHIM) syndrome. Blood 104(2): 444-52.

Guo, F., Y. Wang, J. Liu, S. C. Mok, F. Xue and W. Zhang (2015). "CXCL12/CXCR4: a symbiotic bridge linking cancer cells and their stromal neighbors in oncogenic communication networks." *Oncogene.*

Hashimoto G, Wright P F, Karzon D T. Antibody-dependent cell-mediated cytotoxicity against influenza virus-infected cells. J Infect Dis. 1983 November; 148(5):785-94.

Holm N. T., Abreo F., et al. (2009) Elevated chemokine receptor CXCR4 expression in primary tumors following neoadjuvant chemotherapy predicts poor outcomes for patients with locally advanced breast cancer (LABC). Breast Cancer Res Treat. 113(2):293-9. Epub 2008 Feb. 13

Hwang J. H., Chung H. K., et al. (2003) CXC chemokine receptor 4 expression and function in human anaplastic thyroid cancer cells. J Clin Endocrinol Metab 88(1): 408-16.

Jin L., Tabe Y., et al. (2008) CXCR4 up-regulation by imatinib induces chronic myelogenous leukemia (CML) cell migration to bone marrow stroma and promotes survival of quiescent CML cells. Mol Cancer Ther 7(1): 48-58

Kanbe K., Takagishi K., et al. (2002) Stimulation of matrix metalloprotease 3 release from human chondrocytes by the interaction of stromal cell-derived factor 1 and CXC chemokine receptor 4. Arthritis Rheum 46(1): 130-7.

Kawai T., Choi U., et al. (2005) Enhanced function with decreased internalization of carboxy-terminus truncated CXCR4 responsible for WHIM syndrome. Exp Hematol 33(4): 460-8.

Kioi M., Vogel H., et al. (2010) Inhibition of vasculogenesis, but not angiogenesis, prevents the recurrence of glioblastoma after irradiation in mice. J Clin Invest 120(3): 694-705.

Klussmann S. (2006). The Aptamer Handbook—Functional Oligonucleotides and their Applications. Edited by S. Klussmann. WILEY-VCH, Weinheim, Germany, ISBN 3-527-31059-2

Koshiba T., Hosotani R., et al. (2000) Expression of stromal cell-derived factor 1 and CXCR4 ligand receptor system in pancreatic cancer: a possible role for tumor progression. Clin Cancer Res 6(9): 3530-5.

Kozin S. V., Kamoun W. S., et al. (2010) Recruitment of myeloid but not endothelial precursor cells facilitates tumor regrowth after local irradiation. Cancer Res 70(14): 5679-85.

Krumbholz M., Theil D., et al. (2006) Chemokines in multiple sclerosis: CXCL12 and CXCL13 up-regulation is differentially linked to CNS immune cell recruitment. Brain 129: 200-211.

Kryczek I., Lange A., et al. (2005) CXCL12 and vascular endothelial growth factor synergistically induce neoangiogenesis in human ovarian cancers. Cancer Res 65(2): 465-72.

Kurtova A. V., Balakrishnan K., et al. (2009) Diverse marrow stromal cells protect CLL cells from spontaneous and drug-induced apoptosis: development of a reliable and reproducible system to assess stromal cell adhesion-mediated drug resistance. Blood. 114(20):4441-50.

Kusser W. (2000) Chemically modified nucleic acid aptamers for in vitro selections: evolving evolution. J Biotechnol 74(1): 27-38.

Lagneaux L., Delforge A., et al. (1998) Chronic lymphocytic leukemic B cells but not normal B cells are rescued from apoptosis by contact with normal bone marrow stromal cells. Blood. 91(7):2387-96.

Li J. K., Yu L., et al. (2008) Inhibition of CXCR4 activity with AMD3100 decreases invasion of human colorectal cancer cells in vitro. World J Gastroenterol 14(15): 2308-2313

Maksym R. B., Tarnowski M., et al. (2009) The role of stromal-derived factor-1-CXCR7 axis in development and cancer. Eur J Pharmacol. 625(1-3):31-40. Review.

Marechal V., Arenzana-Seisdedos F., et al. (1999) Opposite effects of SDF-1 on human immunodeficiency virus type 1 replication. J Virol 73(5): 3608-15.

McGinnis S., Madden T. L. et al. (2004) BLAST: at the core of a powerful and diverse set of sequence analysis tools. Nucleic Acids Res. 32(Web Server issue):W20-5.

Meads M. B., Hazlehurst L. A., et al. (2008) The bone marrow microenvironment as a tumor sanctuary and contributor to drug resistance. Clin Cancer Res. 14(9): 2519-26. Review.

Meleth A. D., Agron E., et al. (2005) Serum inflammatory markers in diabetic retinopathy. Invest Ophthalmol Vis Sci 46(11): 4295-301.

Miao, Z., Luker K. E., et al. (2007) CXCR7 (RDC1) promotes breast and lung tumor growth in vivo and is expressed on tumor-associated vasculature. Proc Natl Acad Sci USA 104(40): 15735-40.

Mitsiades C. S., Mitsiades N., et al. (2004) Focus on multiple myeloma. Cancer Cell. 6(5):439-44. Review.

Mitsiades C. S., Mitsiades N. S., et al. (2003) Fluorescence imaging of multiple myeloma cells in a clinically relevant SCID/NOD in vivo model: biologic and clinical implications. Cancer Res. 63(20):6689-96.

Mizell J., Smith M., et al. (2009) Overexpression of CXCR4 in primary tumor of patients with HER-2 negative breast cancer was predictive of a poor disease-free survival: a validation study. Ann Surg Oncol. 16(10):2711-6.

Muller, A., Homey B., et al. (2001) Involvement of chemokine receptors in breast cancer metastasis. Nature 410 (6824): 50-6.

Murdoch, C. (2000) CXCR4: chemokine receptor extraordinaire. Immunol Rev 177: 175-84.

Needleman and Wunsch (1970) A general method applicable to the search for similarities in the amino acid sequence of two proteins. J Mol Biol. 48(3):443-53.

Nervi B., Ramirez P., et al. (2009) Chemosensitization of acute myeloid leukemia (AML) following mobilization by the CXCR4 antagonist AMD3100. Blood. 113(24): 6206-14. Epub 2008 Dec. 2

Pearson and Lipman (1988) Improved tools for biological sequence comparison. Proc. Nat'l. Acad. Sci. USA 85: 2444

Pollara J, Hart L, Brewer F, Pickeral J, Packard B Z, Hoxie J A, Komoriya A, Ochsenbauer C, Kappes J C, Roederer M, Huang Y, Weinhold K J, Tomaras G D, Haynes B F, Montefiori D C, Ferrari G. High-throughput quantitative analysis of HIV-1 and IV-specific ADCC-mediating antibody responses. Cytometry A. 2011 August; 79(8)

Redjal N., Chan J. A., et al. (2006) CXCR4 inhibition synergizes with cytotoxic chemotherapy in gliomas. Clin Cancer Res. 12(22):6765-71.

Roccaro, A. M., A. Sacco, W. G. Purschke, M. Moschetta, K. Buchner, C. Maasch, D. Zboralski, S. Zollner, S. Vonhoff, Y. Mishima, P. Maiso, M. R. Reagan, S. Lonardi, M. Ungari, F. Facchetti, D. Eulberg, A. Kruschinski, A. Vater, G. Rossi, S. Klussmann and I. M. Ghobrial (2014). "SDF-1 inhibition targets the bone marrow niche for cancer therapy." *Cell Rep* 9(1): 118-128.

Salcedo R., Wasserman K., et al. (1999) Vascular endothelial growth factor and basic fibroblast growth factor induce expression of CXCR4 on human endothelial cells: In vivo neovascularization induced by stromal-derived factor-1 alpha. Am J Pathol 154(4): 1125-1135

Salcedo, R. and Oppenheim J. J. (2003) Role of chemokines in angiogenesis: CXCL12/SDF-1 and CXCR4 interaction, a key regulator of endothelial cell responses. Microcirculation 10(3-4): 359-70.

Salvucci O., Yao L., et al. (2002) Regulation of endothelial cell branching morphogenesis by endogenous chemokine stromal-derived factor-1. Blood 99(8): 2703-11.

Saur D., Seidler B., et al. (2005) CXCR4 expression increases liver and lung metastasis in a mouse model of pancreatic cancer. Gastroenterology. 129(4):1237-50.

Schimanski C. C., Galle P. R., et al. (2008) Chemokine receptor CXCR4-prognostic factor for gastrointestinal tumors. World J Gastroenterol. 14(30):4721-4.

Scotton C. J., Wilson J. L., et al. (2002) Multiple actions of the chemokine CXCL12 on epithelial tumor cells in human ovarian cancer. Cancer Res. 62(20):5930-8

Sengupta N., Caballero S., et al. (2005) Preventing stem cell incorporation into choroidal neovascularization by targeting homing and attachment factors. Invest Ophthalmol Vis Sci. 46(1):343-8.

Shaked Y., Henke E., et al. (2008) Rapid chemotherapy-induced acute endothelial progenitor cell mobilization: implications for antiangiogenic drugs as chemosensitizing agents. Cancer Cell. 14(3):263-73

Sharma, P. and J. P. Allison (2015). "The future of immune checkpoint therapy." *Science* 348(6230): 56-61.

Shirozu M., Nakano T., et al. (1995) Structure and chromosomal localization of the human stromal cell-derived factor 1 (SDF1) gene. Genomics 28(3): 495-500.

Smith and Waterman (1981), Adv. Appl. Math. 2: 482

Soriano A., Martinez C., et al. (2002) Plasma stromal cell-derived factor (SDF)-1 levels, SDF1-3'A genotype, and expression of CXCR4 on T lymphocytes: their impact on resistance to human immunodeficiency virus type 1 infection and its progression. J Infect Dis 186(7): 922-31.

Su L., Zhang J, et al. (2005) Differential expression of CXCR4 is associated with the metastatic potential of human non-small cell lung cancer cells. Clin Cancer Res. 11(23):8273-80.

Sunshine, J. and J. M. Taube (2015). "PD-1/PD-L1 inhibitors." *Curr Opin Pharmacol* 23: 32-38.

Tseng D., Lartey F. et al. (2010) J. K., Yu L., et al. (2008) (MS108) Inhibition of SDF-1/CXCR7 radiosensitizes ENU induced glioblastomas in the rat. 56th Annual Meeting Radiation Research Society, Sep. 25-29, 2010, Grand Wailea Resort Hotel and Spa, Maui, Hi., USA Vater A, Sahlmann J, Kröger N, Zöllner S, Lioznov M, Maasch C, Buchner K, Vossmeyer D, Schwoebel F, Purschke W G, Vonhoff S, Kruschinski A, Hübel K, Humphrey M, Klussmann S, Fliegert F. Hematopoietic stem and progenitor cell mobilization in mice and humans by a first-in-class mirror-image oligonucleotide inhibitor of CXCL12. Clin Pharmacol Ther. 2013 July; 94(1):150-7.

Venkatesan N., Kim S. J., et al. (2003) Novel phosphoramidite building blocks in synthesis and applications toward modified oligonucleotides. Curr Med Chem 10(19): 1973-91.

Wang J., Guan E., et al. (2001) Role of tyrosine phosphorylation in ligand-independent sequestration of CXCR4 in human primary monocytes-macrophages. J Biol Chem 276(52): 49236-43.

Wang J., Shiozawa Y., et al. (2008) The role of CXCR7/RDC1 as a chemokine receptor for CXCL12/SDF-1 in prostate cancer. J Biol Chem 283(7): 4283-4294. Epub 2007 Dec. 5.

Wang N., Wu Q. L., et al. (2005) Expression of chemokine receptor CXCR4 in nasopharyngeal carcinoma: pattern of expression and correlation with clinical outcome. J Transl Med 3: 26.

Xu L., Duda D. G., et al. (2009) Direct evidence that bevacizumab, an anti-VEGF antibody, up-regulates SDF1alpha, CXCR4, CXCL6, and neuropilin 1 in tumors from patients with rectal cancer. Cancer Res. 69(20): 7905-10.

Yamaguchi J., Kusano K. F., et al. (2003) Stromal cell-derived factor-1 effects on ex vivo expanded endothelial progenitor cell recruitment for ischemic neovascularization. Circulation 107(9): 1322-8.

Yang J., Zhang B. et al. (2008) Breast cancer metastasis suppressor 1 inhibits SDF-1alpha-induced migration of non-small cell lung cancer by decreasing CXCR4 expression. Cancer Lett 269(1):46-56

Zagzag D., Esencay M., et al. (2008) Hypoxia- and vascular endothelial growth factor-induced stromal cell-derived factor-1 alpha/CXCR4 expression in glioblastomas: one plausible explanation of Scherer's structures. Am J Pathol 173(2): 545-560

Zeelenberg I. S., Ruuls-Van Stalle L., et al. (2003) The chemokine receptor CXCR4 is required for outgrowth of colon carcinoma micrometastases. Cancer Res. 63(13): 3833-9.

Zheng K., Li H. Y., et al. (2010) Chemokine receptor CXCR7 regulates the invasion, angiogenesis and tumor growth of human hepatocellular carcinoma cells. J Exp Clin Cancer Res. 29:31.

Zhou Y., Larsen P. H., et al. (2002) CXCR4 is a major chemokine receptor on glioma cells and mediates their survival. J Biol Chem 277(51): 49481-7.

Zhu A. X., Sahani D. V., et al. (2009) Efficacy, safety, and potential biomarkers of sunitinib monotherapy in advanced hepatocellular carcinoma: a phase II study. J Clin Oncol 27(18): 3027-35.

The features of the present invention disclosed in the specification, the claims and/or the drawings may both separately and in any combination thereof be material for realizing the invention in various forms thereof.

The invention claimed is:

1. A method for modulating number and/or spatial distribution of NK cells that infiltrate a tumor in the treatment of a subject suffering from the tumor, wherein the method comprises administering to the subject a molecule that inhibits signaling between SDF-1 and CXCR4 and/or CXCR7 thereby modulating number and/or the spatial distribution of NK cells that infiltrate the tumor; and at least one checkpoint inhibitor, wherein said molecule comprises an L-nucleic acid and is selected from the group consisting of an SDF-1 binding nucleic acid molecule of type B, an SDF-1 binding nucleic acid molecule of type C, an SDF-1 binding nucleic acid molecule of type A and an SDF-1 binding nucleic acid molecule of type D, wherein the SDF-1 binding nucleic acid molecule of type B comprises in 5'→3' direction a first terminal stretch of nucleotides, a central stretch of nucleotides and a second terminal stretch of nucleotides; or a second terminal stretch of nucleotides, a central stretch of nucleotides and a first terminal stretch of nucleotides, and wherein the central stretch of nucleotides comprises the nucleotide sequence of

```
                          (SEQ ID NO: 52)
5' GUGUGAUCUAGAUGUADWGGCUGWUCCUAGUYAGG 3';
```

the SDF-binding nucleic acid molecule of type C comprises in 5'→3' direction a first terminal stretch of nucleotides, a central stretch of nucleotides and a second terminal stretch of nucleotides; or a second terminal stretch of nucleotides, a central stretch of nucleotides and a first terminal stretch of nucleotides, and wherein the central stretch of nucleotides comprises the nucleotide sequence of GGUYAGGGCUHRX$_A$AGUCGG (SEQ ID NO:108), wherein X$_A$ is either absent or is A;

the SDF-binding nucleic acid molecule of type A comprises in 5'→3' direction a first terminal stretch of nucleotides, a central stretch of nucleotides and a second terminal stretch of nucleotides; or a second terminal stretch of nucleotides, a central stretch of nucleotides and a first terminal stretch of nucleotides, and wherein the central stretch of nucleotides comprises the nucleotide sequence of 5' AAAGYRACAHGUMAAX$_A$UGAAAGGUARC 3' (SEQ ID NO:74), wherein X$_A$ is either absent or is A; or the SDF-1 binding nucleic acid molecule of type D comprises the nucleotide sequence according to any one of SEQ ID NO:142 to SEQ ID NO:144.

2. The method of claim 1, wherein the method comprises inducing an NK cell mediated immune response against the tumor.

3. The method of claim 1, wherein the molecule:

a) increases the number of NK cells in a tumor, and/or b) leads to a more homogeneous spatial distribution of NK cells in a tumor as compared to not using the method of claim 1, and/or c) leads to a spatial distribution of NK cells to more compartments in a tumor as compared to not using the method of claim 1.

4. The method of claim 2, wherein the NK cell mediated immune response against the tumor is enhanced, and/or an antibody-dependent cellular cytotoxicity is enhanced.

5. The method of claim 1, wherein the tumor is selected from the group consisting of a solid tumor, a lymphoma, a myeloma and precursor thereof.

6. The method of claim 1, wherein the central stretch of nucleotides of a type B nucleic acid molecule comprises the following nucleotide sequence:

```
                          (SEQ ID NO: 53)
5' GUGUGAUCUAGAUGUADUGGCUGAUCCUAGUCAGG 3'.
```

7. The method of claim 1, wherein the SDF-1 binding nucleic acid molecule of type B comprises the nucleotide sequence according to any one of SEQ ID NO:5 to SEQ ID NO:20 or SEQ ID NO:22 to SEQ ID NO:28.

8. The method of claim 7, wherein the SDF-1 binding nucleic acid molecule of type B comprises the nucleotide sequence according to any one of SEQ ID NO:22 or SEQ ID NO:28.

9. The method of claim 1, wherein the central stretch of nucleotides of a type C SDF-1 binding nucleic acid molecule comprises the nucleotide sequence of 5' GGUYAGGHRAAGUCGG 3' (SEQ ID NO:109), 5' GGUYAGGGCUHRAGUCGG 3' (SEQ ID NO:110) or 5' GGUUAGGGCUHGAAGUCGG 3' (SEQ ID NO:111).

10. The method of claim 1, wherein the type C SDF-1 binding nucleic acid molecule comprises the nucleotide sequence according to any one of SEQ ID NO:95 to SEQ ID NO:107, SEQ ID NO:112 to SEQ ID NO:137, SEQ ID NO:223 or SEQ ID NO:224.

11. The method of claim 1, wherein the central stretch of nucleotides of a type A SDF-1 binding nucleic acid molecule comprises the nucleotide sequence of

```
                          (SEQ ID NO: 75)
5'AAAGYRACAHGUMAAUGAAAGGUARC 3',
or

                          (SEQ ID NO: 76)
5' AAAGYRACAHGUMAAAUGAAAGGUARC 3',
or

                          (SEQ ID NO: 77)
5' AAAGYAACAHGUCAAUGAAAGGUARC 3'.
```

12. The method of claim 1, wherein the SDF-1 binding nucleic acid molecule of type A comprises the nucleotide sequence according to any one of SEQ ID NO:60 to SEQ ID NO:73, SEQ ID NO:78 to SEQ ID NO:82, SEQ ID NO:84 to SEQ ID NO:87, SEQ ID NO:89 to SEQ ID NO:94, SEQ ID NO:145 or SEQ ID NO:146.

13. The method of claim 1, wherein the molecule comprises a modification, whereby the modification allows modifying characteristics of the nucleic acid molecule in terms of residence time in an animal or a human body.

14. The method of claim 13, wherein the modification is selected from the group consisting of an HES moiety, a PEG moiety, biodegradable modifications thereof and combinations thereof.

15. The method of claim 1, wherein the checkpoint inhibitor is selected from the group consisting of a PD-1 signaling inhibitor, a CTLA-4 antagonist, a TIM-3 antagonist and an LAG3 antagonist.

16. The method of claim 15, wherein the PD-1 signaling inhibitor is a PD-1 inhibitor or a PDL-1 inhibitor.

17. The method of claim 16, wherein if the PD-1 inhibitor is administered, the PD-1 inhibitor is an anti-PD-1 antibody, and wherein if the PDL-1 inhibitor is administered, the PDL-1 inhibitor is an anti-PDL-1 antibody.

* * * * *